(12) United States Patent
Yu et al.

(10) Patent No.: US 11,857,545 B2
(45) Date of Patent: *Jan. 2, 2024

(54) HIGH PENETRATION PRODRUG COMPOSITIONS AND PHARMACEUTICAL COMPOSITION THEREOF FOR TREATMENT OF PULMONARY CONDITIONS

(71) Applicant: TECHFIELDS PHARMA CO., LTD., Jiangsu (CN)

(72) Inventors: Chongxi Yu, Plainfield, IL (US); Lina Xu, Jiangsu (CN)

(73) Assignee: Techfields Pharma Co., Ltd., Suzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/542,486

(22) Filed: Nov. 14, 2014

(65) Prior Publication Data

US 2015/0072961 A1    Mar. 12, 2015

Related U.S. Application Data

(63) Continuation of application No. PCT/CN2013/072693, filed on Mar. 15, 2013.

(30) Foreign Application Priority Data

May 16, 2012    (CN) .......................... 201210151555.7

(51) Int. Cl.
| | |
|---|---|
| *A61K 31/47* | (2006.01) |
| *A61K 47/54* | (2017.01) |
| *A61K 31/4545* | (2006.01) |
| *A61K 31/135* | (2006.01) |
| *A61K 31/43* | (2006.01) |
| *A61K 31/445* | (2006.01) |
| *A61K 31/381* | (2006.01) |
| *A61K 31/625* | (2006.01) |
| *A61K 45/06* | (2006.01) |

(52) U.S. Cl.
CPC ........ *A61K 31/4545* (2013.01); *A61K 31/135* (2013.01); *A61K 31/381* (2013.01); *A61K 31/43* (2013.01); *A61K 31/445* (2013.01); *A61K 31/47* (2013.01); *A61K 31/625* (2013.01); *A61K 45/06* (2013.01); *A61K 47/54* (2017.08)

(58) Field of Classification Search
CPC ................ A61K 31/47; A61K 47/54
See application file for complete search history.

(56) References Cited

U.S. PATENT DOCUMENTS

| | | | |
|---|---|---|---|
| 2,671,805 A | 3/1954 | Krimmel et al. | |
| 2,694,031 A | 11/1954 | Frederiksen et al. | |
| 2,694,061 A | 11/1954 | Frederiksen et al. | |
| 2,694,063 A | 11/1954 | Frederiksen | |
| 3,365,483 A | 1/1968 | Jerzmanowska et al. | |
| 3,420,871 A | 1/1969 | Scherrer et al. | |
| 3,914,811 A | 10/1975 | Francis | |
| 3,956,363 A | 5/1976 | Shen et al. | |
| 3,957,764 A | 5/1976 | Lund | |
| 3,966,923 A | 6/1976 | Serre | |
| 4,006,181 A | 2/1977 | Cousse et al. | |
| 4,012,508 A | 3/1977 | Burton | |
| 4,127,671 A | 11/1978 | Cognacq | |
| 4,150,157 A | 4/1979 | Ferres | |
| 4,180,662 A | 12/1979 | Pfister et al. | |
| 4,206,220 A | 6/1980 | Sloan | |
| 4,215,120 A | 7/1980 | Ferres | |
| 4,244,948 A | 1/1981 | Boghosian et al. | |
| 4,496,574 A | 1/1985 | Muto et al. | |
| 4,640,689 A | 2/1987 | Sibalis | |
| 4,699,920 A | 10/1987 | Skuballa et al. | |
| 4,743,704 A | 5/1988 | Nicolini | |
| 4,746,509 A | 5/1988 | Haggiage et al. | |
| 4,822,773 A | 4/1989 | Alexander et al. | |
| 5,190,953 A | 3/1993 | Munson, Jr. et al. | |
| 5,321,020 A | 6/1994 | Jasys | |

(Continued)

FOREIGN PATENT DOCUMENTS

| | | |
|---|---|---|
| AU | 457864 | 1/1975 |
| CA | 1246446 | 12/1988 |

(Continued)

OTHER PUBLICATIONS

Trivedi et al (Eur J Pharm Sci, 1996; 4:109-116).*
Jarvinen et al (Pharmaceutical Sciences Encyclopedia: Drug Discovery, Development, and Manufacturing, 2010, ed. Shayne C. Gad, pp. 1-64).*
Mahfouz et al (Journal of Pharmacy and Pharmacology, 2001; 53:841-848).*
Walson et al (Clinical Therapeutics, 2006; 28(5):762-769).*
Digenis et al ("Drug latentiation." Concepts in Biochemical Pharmacology. Springer, Berlin, Heidelberg, 1975. 86-112) (Year: 1975).*
Altuntas, T.G., et al., "A Study on the Interaction Between p60c-Src Receptor Tyrosine Kinase and Arylcarboxylic and Arylacetic Acid Derivatives Based on Docking Modes and In Vitro Activity," Biological & Pharmaceutical Bulletin 27(1):61-65 (2004).

(Continued)

*Primary Examiner* — Rayna Rodriguez
(74) *Attorney, Agent, or Firm* — Fox Rothschild LLP

(57) ABSTRACT

The invention provides compositions of novel high penetration compositions (HPC) or high penetration prodrugs (HPP) for treatment of pulmonary conditions (e.g. asthma). The HPCs/HPPs are capable of being converted to parent active drugs or drug metabolites after crossing the biological barrier and thus can render treatments for the conditions that the parent drugs or metabolites can. Additionally, the HPPs are capable of reaching areas that parent drugs may not be able to access or to render a sufficient concentration at the target areas and therefore render novel treatments. The HPCs/HPPs can be administered to a subject through various administration routes, e.g., locally delivered to an action site of a condition with a high concentration or systematically administered to a biological subject and enter the general circulation with a faster rate.

8 Claims, No Drawings

(56) References Cited

U.S. PATENT DOCUMENTS

| | | | |
|---|---|---|---|
| 5,399,562 A | 3/1995 | Becker et al. | |
| 5,570,559 A | 11/1996 | Lewis | |
| 5,629,019 A | 5/1997 | Lee et al. | |
| 5,654,337 A | 8/1997 | Roentsch et al. | |
| 5,760,261 A | 6/1998 | Guttag | |
| 5,861,170 A | 1/1999 | Kissel | |
| 5,885,597 A | 3/1999 | Botknecht et al. | |
| 5,929,086 A | 7/1999 | Watts et al. | |
| 6,011,049 A | 1/2000 | Whitcomb | |
| 6,190,690 B1 | 2/2001 | Park et al. | |
| 6,191,143 B1 | 2/2001 | Watts et al. | |
| 6,346,278 B1 | 2/2002 | Macrides et al. | |
| 6,368,618 B1 | 4/2002 | Jun et al. | |
| 6,416,772 B1 | 7/2002 | Van Engelen et al. | |
| 6,444,234 B1 | 9/2002 | Kirby et al. | |
| 6,451,815 B1 | 9/2002 | Hwang et al. | |
| 6,528,040 B1 | 3/2003 | Pearson et al. | |
| 6,638,528 B1 | 10/2003 | Kanios | |
| 6,773,724 B2 | 8/2004 | Franckowiak et al. | |
| 7,052,715 B2 | 5/2006 | Fishman | |
| 7,256,210 B2 | 8/2007 | Man et al. | |
| 2002/0127198 A1 | 9/2002 | Rothbard et al. | |
| 2003/0087962 A1 | 5/2003 | Demopulos et al. | |
| 2004/0109826 A1* | 6/2004 | Malladi | A61K 31/137 424/45 |
| 2004/0229920 A1 | 11/2004 | Garvey et al. | |
| 2005/0037922 A1 | 2/2005 | Bickers et al. | |
| 2005/0049255 A1 | 3/2005 | Bictash et al. | |
| 2005/0107463 A1 | 5/2005 | Woodward et al. | |
| 2005/0277634 A1 | 12/2005 | Janott et al. | |
| 2006/0003428 A1 | 1/2006 | Tsai | |
| 2006/0222692 A1 | 10/2006 | Lane | |
| 2006/0241017 A1 | 10/2006 | Chandran | |
| 2010/0040548 A1* | 2/2010 | Yu | A61P 31/04 424/9.1 |

FOREIGN PATENT DOCUMENTS

| | | | |
|---|---|---|---|
| CN | 1883481 A * | 12/2006 | |
| DE | 3023206 A1 | 1/1982 | |
| EP | 0152379 A2 | 8/1985 | |
| EP | 0202062 A2 | 11/1986 | |
| EP | 0289262 A2 | 11/1988 | |
| EP | 0469450 A1 | 5/1992 | |
| EP | 026744 B1 | 3/1994 | |
| FR | 5342 M | 9/1967 | |
| FR | 2132447 | 4/1976 | |
| GB | 759603 | 10/1956 | |
| GB | 768347 | 2/1957 | |
| GB | 958186 A | 5/1964 | |
| GB | 984471 A | 2/1965 | |
| GB | 100208 A | 8/1965 | |
| GB | 1165300 | 9/1969 | |
| GB | 1187259 A | 4/1970 | |
| GB | 1470154 | 4/1977 | |
| GB | 2157284 A | 10/1985 | |
| JP | 57-183738 A | 11/1982 | |
| JP | 02254425 A2 | 10/1990 | |
| WO | 93/07902 | 4/1993 | |
| WO | 94/00449 | 1/1994 | |
| WO | 94/10167 | 5/1994 | |
| WO | 1995/24813 | 12/1995 | |
| WO | 1996/028144 | 9/1996 | |
| WO | 1997/42954 A1 | 11/1997 | |
| WO | 1997/44020 A1 | 11/1997 | |
| WO | 1998/040061 | 9/1998 | |
| WO | 1999/038510 | 8/1999 | |
| WO | 2000/047589 A1 | 8/2000 | |
| WO | 2002/000167 A2 | 1/2002 | |
| WO | 2002/068377 A1 | 9/2002 | |
| WO | 2003/022270 A1 | 3/2003 | |
| WO | 2003032912 A3 | 4/2003 | |
| WO | 2003/061713 A1 | 7/2003 | |
| WO | 2004/000300 A1 | 12/2003 | |
| WO | 2004/009538 A1 | 1/2004 | |
| WO | WO 2004/022099 A2 | 3/2004 | |
| WO | 2005030331 A1 | 4/2005 | |
| WO | 2005/097099 A1 | 10/2005 | |
| WO | 2006/128184 A2 | 11/2006 | |
| WO | WO 2007/089745 A2 | 8/2007 | |
| WO | 2008/007171 A1 | 1/2008 | |
| WO | 2008/010025 A1 | 1/2008 | |
| WO | 2008/012602 A1 | 1/2008 | |
| WO | 2008/012603 A1 | 1/2008 | |
| WO | 2008/021605 A1 | 1/2008 | |
| WO | 2008/017903 A1 | 2/2008 | |
| WO | 2008/020270 A1 | 2/2008 | |
| WO | 2008/026776 | 3/2008 | |
| WO | 2008/029199 A1 | 3/2008 | |
| WO | 2008/029200 A1 | 3/2008 | |
| WO | 2008/041054 A1 | 4/2008 | |
| WO | 2008/041059 A1 | 4/2008 | |
| WO | 2008/044095 A1 | 4/2008 | |
| WO | 2008/072032 A1 | 6/2008 | |
| WO | 2008/093173 A1 | 8/2008 | |
| WO | 2008/149181 A1 | 12/2008 | |
| WO | WO-2009122187 A2 * | 10/2009 | A61K 31/00 |
| WO | 2010/065936 A1 | 6/2010 | |
| WO | 2010/142241 A1 | 12/2010 | |

OTHER PUBLICATIONS

Andrews, J. M., "Determination of Minimum Inhibitory Concentrations," Journal of Antimicrobial Chemotherapy 48, suppl. S1: 5-16 (2001).

Arora, P., et al., "Design Development, Physiochemical, and In Vitro and In Vivo Evaluation of Transdermal Patches Containing Diclofenac Diethylammonium Salt," J. Pham. Sci. 91:2076-2089 (2002).

Bagyalakshmi, J., et al., "Pharmacodynamics of Ampicillin Sodium Transdermal Patches in an In Vitro Infection Model," Indian Journal of Pharmaceutical Sciences 68(4):540-541 (2006).

Barcia, E., et al., "Influence of Medium and Temperature on the Hydrolysis Kenetics of Propacetamol Hydrochloride: Determination Using Derivative Spectrophotometry," Chem. Pharm. Bull. 53(3):277-280 (2005).

Barnden, R. L., et al., "Some Preparative Uses of Benzylpenicillinic Ethoxyformic Anhydride," J. Chem. Soc. pp. 3733-3739 (1953).

Battaglino, R., et al., "Fluoxetine Treatment Increases Trabecular Bone Formation in Mice (Fluoxetine Affects Bone Mass)," J. Cell Biochem. 100(6):1387-1394 (2007).

Berge, S.M., et al., "Pharmaceutical Salts," J. Pharm. Sci. 66(1):1-19 (1977).

Brown, K., et al., "Nonsteroidal Antiinflammatory Agents. 1.2,4-Diphenylthiazole-5-acetic Acid and Related Compounds," J. Med. Chem. 17(11):1177-1181 (1975).

Cannon, J. G., "Analog Design," Burger's Medicinal Chemistry and Drug Discovery 5th Ed. 1:783-802 (1995).

Chanal, J. L., et al., "Study on the Distribution and Elimination of Dimethylaminoethyl Acetylsalicylate in the Rat. Effect of the Carbon-14 Labeling Position," Bollettino Chimico Farmaceutico 119(6):331-338 (1980).

Choi, I., et al., "9-Cis Retinoid Acid Promotes Lymphangiogenesis and Enhances Lymphatic Vessel Regeneration: Therapeutic Implications of 9-Cis Retinoic Acid for Secondary Lymphedema," Circulation 125(7):872-882 (2012).

D'Amour, F. E., et al., "A Method for Determining Loss of Pain Sensation," J. Pharmacol. Exp. Ther. 72:74-79 (1941).

Dalpiaz, A., et al., "Vitamin C and 6-Amino-Vitamin C Conjugates of Diclofenac: Synthesis and Evaluation," International Journal of Pharmaceutics 291(1-2):171-181 (2005).

Database Caplus [Online] Chemical Abstracts Service, Columbus, OH, US; "Esters of .Omega.-Aminoaliphatic Acids and p-Acetamidophenol," retrieved from STN database accession No. 1969:3537.

Database Caplus [Online] Chemical Abstracts Service, Columbus, OH, US; "Effect of Penicillinase on Certain Salts and Esters of Penicillin," retrieved from STN database accession No. 61:33936 (2001).

(56) References Cited

OTHER PUBLICATIONS

Dawson, M. I., et al., "The Retinoid X Receptors and Their Ligands," Biochim. Biophys. Acta 1821(1):21-56 (2012).
Drachman, D.B., et al., "Cycloxygenase 2 Inhibition Protects Motor Neurons and Prolongs Survival in a Transgenic Mouse Model of ALS," Annals of Neurology 52:771-778 (2002).
Erlanson-Albertsson, C., et al., "Enterostatin—A Peptide Regulating Fat Intake," Obes. Res. 5(4):360-372 (1997).
Euler et al., Hoppe-Seyler's Zeitschrift fuer Physiologische Chemie 288:250-251 (1951).
Farkas, E. R., et al., "Synthesis of Penicillin Sulfoxides and Their Esters," Magyar Kemiai Folyoirat 84(6):257-260 (1978).
Gamache, D.A., et al., "Nepafenac, A Unique Nonsteroidal Prodrug with Potential Utility in the Treatment of Trauma-Induced Ocular Inflammation: I. Asssessment of Anti-Inflammatory Efficacy," Inflammation 24(4):357-370 (2000).
Gidoh, M., et al., "Studies on the Derivatives Showing Local Anesthetic Actions of Several Acidic Antiinflammatory Drugs, Aiming at the Possibility of Treatment of Leprous Neuritis," Jap. J. Leprosy 52:156-164 (1983).
Ginaldi, L., et al., "Osteoporosis, Inflammation and Ageing," Immunity & Ageing 2:14 (2005).
Giraldez et al., "Kinetics of DAN-523. Modification of an Antibiotic from the Group of Semisynthetic Penicillins of Selective Excretion through Milk," Archivos de Farmacologia y Toxicologia 2(3):311-314 (1976).
Godfrey, A. J., et al., "Penetration of Beta-Lactams Through Pseudomonas Aeruginosa Porin Channels," Antimicrobial Agents & Chemotherapy 31(8):1216-1221 (1987).
Gossel, T. A., "Aspirin's Role in Reducing Cardiac Mortality," U.S. Pharmacist pp. 34-41 (1988).
Halen, P. K., et al., "Synthesis and Pharmacological Evaluation of Some Dual-Acting Amino-Alcohol Ester Derivatives of Flurbiprofen and 2-[1,1'-Biphenyl-4-yl]Acetic Acid: A Potential Approach to Reduce Local Gastrointestinal Toxicity," Chemistry & Biodiversity 3(11):1238-1248 (2006).
Halen, P. K., et al., "Combining Anticholinergic and Anti-Inflammatory Activities into a Single Moiety: A Novel Approach to Reduce Gastrointestinal Toxictiy of Ibuprofen and Ketoprofen," Chem. Biol. Drug Des. 70:450-455 (2007).
Hatanaka, T., et al., "Ion Pair Skin Transport of a Zwitterionic Drug, Cephalexin," Journal of Controlled Release 66(1):63-71 (2000).
Hengesh, E. J., Principles of Medicinal Chemistry, 4th Ed., p. 591, Williams & Wilkins, 1995.
Hennekens, C. H., et al., "Final Report on the Aspirin Component of the Ongoing Physicians' Health Study," N. Eng. J. Med. 321:129-135 (1989).
Ho, et al., "The Percutaneous Penetration of Prostaglandin E1 and Its Alkyl Esters," Journal of Controlled Release 58:349 (1999).
Hovgaard, L., et al., "Drug Delivery Studies in Caco-2 Monolayers. Synthesis, Hydrolysis, and Transport of O-Cyclopropane Carboxylic Acid Ester Prodrugs of Various B-Blocking Agents," Pharm. Res. 12(3):387-392 (1995).
Hovgaard, L., et al., "Permeation Studies on O-Cyclopropanoyl Ester Prodrugs of B-Blockers in Caco-2 Cell Monolayers," Proceed. Intern: Symp. Control. Rel. Bioact. Mater. 20:238-239 (1993).
Ilankumaran, P., et al., "Prop-2-ynyl as a Protective Group for Carboxylic Acids: A Mild Method for the Highly Selective Deprotection of Prop-2-ynyl Esters Using Tetrathiomolybdate," Chem. Commun. 1957-1958 (1996).
In t' Veld, B.A., et al., "Nonsteroidal Antiinflammatory Drugs and the Risk of Alzheimer's Disease," New England Journal of Medicine 345(21):1515-1521 (2001).
Jansen, A. B. A., et al., "Some Novel Penicillin Derivatives," J. Chem Soc. 2127-2132 (1965).
Johnson, D. A., "Carboxy Derivatives of Benzylpenicillin," J. Am. Chem. Soc. 75:3636-3637 (1953).
Jung, Y. J., et al., "Colon-Specific Prodrugs of 5-Aminosalicylic Acid: Synthesis and In Vitro/In Vivo Properties of Acidic Amino Acid Derivatives of 5-Aminosalicylic Acid," J. Pharm. Sci. 90:1767-1775 (2001).
Kisel, V.M., et al., "Condensed Isoquinolines. Synthesis of 5,10-Dihydro[1,2,4]Triazolo[1,5-b]Isoquinolines and Related Spiranes," Chemistry of Heterocyclic Compounds 38(10):1253-1262 (2002).
Knychalska-Karwan, Z., et al., "The Use of Edan in Stomatodynia," J. Stomatol. 38:10 (1985).
Kobayashi, M., et al., "A Model System of Convenient Fluorescent Labeling of Sugar Chain in Taka-Amylase A," Bioscience, Biotechnology & Biochemistry 61(11):1836-1839 (1997).
Kovach, I. M., et al., "Amino Acid Esters of Phenols as Prodrugs: Synthesis and Stability of Glycine, beta-Aspartic Acid, and alpha-Aspartic Acid Esters of p-Acetamidophenol," J. Pharm. Sci. 70(8):881-885 (1981).
Kumar, A., et al., "Comparative Study of Cephalexin Hydrochloride and Cephalexin Monohydrate in the Treatment of Skin and Soft Tissue Infections," Antimicrobial Agents and Chemotherapy 32(6):882-885 (1988).
Lazaro, A., et al., "Pharmacokinetic Evaluation and Mammary Excretion of Tamethicillin in the Healthy Goat," Am J Vet Res 40(8):1173-1176 (1979).
Luo, H,et al., "Synthesis and Characterization of Quaternary Ammonium-Linked Glucuronide Metabolites of Drugs with an Aliphatic Tertiary Amine Group," J. Pharm. Sci. 81(11):1079-1083 (1992).
Mandell, G. L., et al., Ch. 46: Antimicrobial Agents, Goodman Gilman's The Pharmacological Basis of Therapeutics. 8th ed., McGraw-Hill, INC. 1991, vol. II, pp. 1065-1097.
Mao, J. T., et al., "A Pilot Study of All-trans-Retinoic Acid for the Treatment of Human Emphysema," Am. J. Respir. Crit. Care Med. 165:718-723 (2002).
Marshall, H., et al., "Retinoids and Hox Genes," FASEB J. 10:969-978 (1996).
McGeer, P. L., et al., "The Inflammatory Response System of Brain Implications for the Therapy of Alzheimer and Other Neurodegenerative Diseases," Brain Res. Rev. 21:195-218 (1995).
Meng-er, H., et al., "Use of All-Trans Retinoic Acid in the Treatment of Acute Promyelocytic Leukemia," Blood 72(2):567-572 (1988).
Milosovich, S., et al., "Testosteronyl-4-Dimethylaminobutyrate-HCI: A Prodrug with Improved Skin Penetration Rate," J. Pharm. Sci. 82(2):227-228 (1993).
Moore, T., et al., "The Production of Experimental Vitamin A Deficiency in Rats and Mice," Lab. Animals 5:239-250 (1971).
Nebioglu, D., et al., "Synthesis and In Vitro Anti-Inflammatory Activities of Some New Diaryl Amine Derivatives as Prodrug of Diclofenac," Journal of Faculty of Pharmacy of Gazi University 10(1):69-81 (1993).
Nielsen, N.M., et al., "Evaluation of Glycolamide Esters and Various Other Esters of Aspirin as True Aspirin Prodrugs," Journal of Medicinal Chemistry 32(3):727-734 (1989).
Non_steroidal_antiinflammatory_dr,2011, http://en.wikipedia.org/wiki/Non-steroidal_anti-inflammatory_drug.
Ohlenschlaeger, K., et al., "Scleroderma Treated with the Diethylamine-Ethylester Hydriodide Salt of Penicillin G.," Dermatologica 134:129-134 (1967).
Pan, D.S., et al., "Inhibitory Effect of Progesterone on Inflammatory Factors after Experimental Traumatic Brain Injury," Biomed. Environ. Sci. 20(5):432-438 (2007).
PDR Generics, 1996, second edition, Medical Economics, Montvale, NJ, p. 242-243.
Perioli, L., et al., "Potential Prodrugs of Non-Steroidal Anti-Inflammatory Agents for Targeted Drug Delivery to the CNS," European Journal of Medicinal Chemistry 39(8):715-727 (2004).
Ponte, C., et al., "Does Acetaminophen Interfere in the Antibiotic Treatment of Acute Otitis Media Caused by a Penicillin-Resistant Pneumococcus Strain? A Gerbil Model," Pediatric Res. 54(6):913-918 (2003).
Raether, W., et al., "Comparison of Two Different Techniques in Primary Mycological Screening: Standard Serial Dilution Tests and Microtitration Test," Mykosen 27(1):14-28 (1984).
Raisz, L., "Pathogenesis of Osteoporosis: Concepts, Conflicts, and Prospects," J. Clin. Invest. 115(12):3318-3325 (2005).

(56) References Cited

OTHER PUBLICATIONS

Romundstad, L., et al., "Adding Propacetamol to Ketorolac Increase the Tolerance to Painful Pressure," Eur. J. Pain 10(3):177-183 (2006).
Roof, R.L., et al., "Gender Differences in Acute CNS Trauma and Stroke: Neuroprotective Effects of Estrogen and Progesterone," J. Neurotrauma 17(5):367-388 (2000).
Rosenberg, E. W., et al., "Effect of Topical Applications of Heavy Suspensions of Killed Malassezia Ovalis on Rabbit Skin," Mycopathologia, 72:147-154 (1980).
Salimbeni, A., et al., "New Esters of N-Arylanthranilic Acids," Farmaco Edizione Scientifica 30(4):276-286 (1975).
Santos, C., et al., "Cyclization-Activated Prodrugs. Synthesis, Reactivity and Toxicity of Dipeptide Esters of Paracetamol," Bioorg. Med. Chem. Letters 15:1695-1598 (2005).
Sanz, M. A., "Treatment of Acute Promyelocytic Leukemia," Hematology 147-155 (2006).
Scott, I. L., "Keystone Symposia: Inflammation and Cancer, Breckenridge, CO, USA, Feb. 27-Mar. 3, 2005," Technical Reports 10(13)1-17.
Shanbhag, V. R., et al., "Ester and Amide Prodrugs of Ibuprogen and Naproxen: Synthesis, Anti-Inflammatory Activity, and Gastrointestinal Toxicity," J. Pharm. Sci. 81(2):149-154 (1992).
Sheridan, R. P., "The Most Common Chemical Replacements in Drug-Like Compounds," J. Chem. Inf. Comput. Sci. 42:103-108 (2002).
Shimshoni, J. A., et al., "Stereoselective Formation and Metabolism of 4-Hydroxy-Retinoic Acid Enantiomers by Cytochrome P450 Enzymes," J. Biol. Chem. 287(50):42223-42232 (2012).
Soine, T. O., et al., "Antispasmodics. I. Phenyl Esters of Beta-Dialkylaminopropionic Acids," J. Am. Pharm. Assoc. 41:236-238 (1952).
Sorhede, M., et al., "Enterostatin: A Gut-Brain Peptide Regulating Fat Intake in Rat," J. Physiol. 87(4):273-275 (1993).
SpinalCordinjury,2011, http://www.mayoclinic.com/health/spinal-cord-injury/DS00460/DSECTION=treatments-and-drugs.
St. Rose, S. G., et al., "Effect of penethamate hydriodide treatment on bacteriological cure, somatic cell count and milk production of cows and quarters with chronic subclinical *Streptococcus uberis* or *Streptococcus dysgalactiae* infection," J. Dairy Res. 70:387-394 (2003).
Tanaka, R., et al., "Structure-Activity Relationships of Penem Antibiotics: Crystallographic Structures and Implications for Their Antimicrobial Activities," Bioorganic & Medicinal Chemistry 5(7):1389-1399 (1997).
Thun, M.J., et al., "Aspirin Use and Reduced Risk of Fatal Colon Cancer," N. Eng. J. Med., 325(23):1593-1596 (1991).
Toyooka, T., et al., "Fluoroescent Chiral Derivatization Reagents for Carboxylic Acid Enantiomers in High-Performance Liquid Chromatography," Caplus an 1992:523750 (1992).
Tozkoparan, B., et al., "6-Benzylidenethiazolo[3,2-b]-1,24-Triazole-5(6H)-Ones Sybstituted with Ibprofen: Synthesis, Characterization and Evaluation of Anti-Inflammatory Activity," Eur. J. Med. Chem. 35(7-8):743-750 (2000).
United States Patent and Trademark Office, International Search Report and Written Opinion dated Jun. 27, 2013 for PCT/CN2013/072693.
Urbanska, H., et al., "Synthesis and Pharmacological Properties of Aminoalkyl Esters Derived from Nicotinic Acid," Acta Polonicae Pharmaceutica 36(6):657-665 (1979).
Van Beek, M. E. A. B., et al., "Spermatogenesis in Retinol-Deficient Rats Maintained on Retinoic Acid," J. Reprod. Fert. 94:327-336 (1992).

Venuti, M. C., et al., "Synthesis and Biological Evaluation of Omega-(N,N,N-Trialkylammonium)alkyl Esters and Thioesters of Carboxylic Acid Nonsteroidal Antiinflammatory Agents," Pharmaceutical Research 6(10):867-873 (1989).
Weingarten, C., "Randomized, Comparative Study of Oral Cefadroxil and Cephalexin in Lower Respiratory Infections in Adults," J. Antimicrob. Chemother. 10(8uppl. B):109-113 (1982).
Wiwattanawongsa, K., et al., "Experimental and Computational Studies of Epithelial Transport of Mefenamic Acid Ester Prodrugs," Pharmaceutical Research 22(5):721-727 (2005).
Woods, H. F., et al., "Inhibition By Salicylate of Gluconeogenesis in the Isolated Perfused Rat Liver," Clin. Exp. Pharmacol. Physiol. 1(6):535-540 (1974).
Wright, D.W., et al., "ProTECT: A Randomized Clinical Trial of Progesterone for Acute Traumatic Brain Injury," Ann. Emerg. Med. 49(4):391-402 (2007).
Xiao, G., et al., "Improved Outcomes from the Administration of Progesterone for Patients with Acute Severe ttraumatic bbrain iinjury: A Randomized Controlled Trial," Crit. Care 12:R61 (2008).
Yadav, M.R., et al., "Synthesis and Pharmacological Evaluation of Some Dual-Acting Aminoalcohol Ester Derivatives of Flurbiprofen and 2-[1,1'-Biphenyl-4-yl] Acetic Acid: A Potential Approach to Reduce Local Gastrointestinal Toxicity," Chem. & Biodiversity 3(11):1238-1248 (2006).
Yang, S., et al., "Specificity of RGS10A as a Key Component in the RANKL Signaling Mechanism for Osteoclast Differentiation," J. Cell Sci. 120:3362-3371 (2007).
Ziv, G., et al., "Concentrations of Methicillin in Blood, Normal Milk and Mastitic Milk of Cows After Intramuscular Injection of Methicillin and Tamethicillin," J. Vet. Pharmacol. Therap. 6(1):41-48 (1983).
Zovko, M., et al., "Macromolecular Prodrugs. IX. Synthesis of Polymer-Fenoprofen Conjugates," International Journal of Pharmaceutics 228(1-2):129-138 (2001).
Lewis et al., "Cetirizine and loratadine-based antihistamines with 5-lipoxygenase inhibitory activity," *Bioorganic & Medicinal Chemistry Letters*, 14(22): 5591-5594 (2004).
Majumdar et al., "Topical delivery of N-alkyl-N-alkyloxycarbonylaminomethyl (NANAOCAM) prodrugs of theophylline (ThH)," *International Journal of Pharmaceutics*, 332(1-2): 64-71 (2007).
Mythri et al., "Glutamoyl diester of the dietary polyphenol curcumin offers improved protection against peroxynitrite-mediated nitrosative stress and damage of brain mitochondria in vitro: implications for Parkinson's disease," *Molecular and Cellular Biochemistry*, 347(1-2): 135-143 (2011).
Nickel et al., "Fenetylline: New results on pharmacology, metabolism and kinetics," *Drug and Alcohol Dependence*, 17(2-3): 235-257 (1986).
European Patent Office, Extended European Search Report for EP 13791142.6, dated Feb. 25, 2016 (20 pages).
Nelson, H. S., "Prospects for Antihistamines in the Treatment of Asthma"; American Academy of Allergy, Asthma and Immunology (2003); vol. 112:4; pp. S96-S100.
Examination Report received in related European Application No. 13791142.6 dated Mar. 16, 2021, 4 pgs.
Cingi, C. et al., "Efficacy of Leukotriene Antagonists as Concomitant Therapy in Allergic Rhinitis"; The Laryngoscope (2010); vol. 120:; pp. 1718-1723.
"Analgesic Asthma: Shortness of Breath on Aspirin," Pharmazeutische Zeitung, Avoxa—Mediengruppe Deutscher Apotheker GmbH (2011); https://www.pharmazeutische-zeitung.de/ausgabe-162011/atemnot%C2%ADauf-aspirin/.

\* cited by examiner

HIGH PENETRATION PRODRUG COMPOSITIONS AND PHARMACEUTICAL COMPOSITION THEREOF FOR TREATMENT OF PULMONARY CONDITIONS

CROSS-REFERENCE TO RELATED APPLICATIONS

The present application is a continuation of International Patent Application No. PCT/CN2013/072693, filed Mar. 15, 2013, which claims priority to Chinese Patent Application No. 20121015155.7, filed May 16, 2012, which is incorporated herein by reference in its entirety, as if fully set forth herein.

FIELD OF THE INVENTION

This invention relates to the field of pharmaceutical compositions capable of penetrating one or more biological barriers and methods of using the pharmaceutical compositions for preventing and/or treating pulmonary conditions (e.g. asthma, lower, and upper respiratory tract infections) in humans and animals. The invention also relates to methods of using the pharmaceutical compositions for screening new drug candidates.

BACKGROUND OF THE INVENTION

Pulmonary conditions may be caused by allergy, inflammation, bacterial infections, or a combination thereof. For example, asthma is a chronic inflammatory condition of the respiratory tract (airway) characterized by airflow obstruction and bronchospasm. Asthma can be classified as a variable and partially reversible obstruction to air flow involving an overdeveloped mucus gland, airway thickening due to scarring and inflammation, and bronchoconstriction. Bronchoconstriction is caused by edema and swelling which may be triggered by an immune response to allergens. Bacterial infections of the upper respiratory tract infection can also worsen asthmatic symptoms.

The airway of an asthmatic or a subject that is experiencing a chronic pulmonary condition (e.g. emphysema and chronic bronchitis) may be thickened due to scaring and inflammation. Therefore, a need exists in the art for novel compositions that are capable of efficient and effective delivery to the action site of a pulmonary condition (e.g., asthma, lower, and upper respiratory tract infections) of a subject to prevent, reduce or treat conditions as well as minimize adverse side effects.

DETAILED DESCRIPTION OF THE INVENTION

I. Structures of High Penetration Prodrug (HPP) or High Penetration Composition (HPC)

One aspect of the invention is directed to a high penetration prodrug (HPP) or a high penetration composition (HPC). The term "high penetration prodrug" or "HPP" or "high penetration composition" or "HPC" as used herein refers to a composition comprising a functional unit covalently linked to a transportational unit through a linker.

Functional Unit

A functional unit of an HPP or HPC which comprises a moiety of a parent drug has the properties of: 1) the delivery of the parent drug or the HPP/HPC into a biological subject and/or the transportation of the parent drug across one or more biological barriers are/is desired, 2) the HPP/HPC is capable of penetrating or crossing one or more biological barriers, and 3) the HPP/HPC is capable of being cleaved so as to turn the moiety of a parent drug into the parent drug or a metabolite of the parent drug.

In certain embodiments, a functional unit may be hydrophilic, lipophilic, or amphiphilic (hydrophilic and lipophilic). The lipophilic moiety of the functional unit may be inherent or achieved by converting one or more hydrophilic moieties of the functional unit to lipophilic moieties. For example, a lipophilic moiety of a functional unit is produced by converting one or more hydrophilic groups of the functional unit to lipophilic groups via organic synthesis. Examples of hydrophilic groups include, without limitation, carboxylic, hydroxyl, thiol, amine, phosphate/phosphonate, guanidine and carbonyl groups. Lipophilic moieties produced via the modification of these hydrophilic groups include, without limitation, ethers, thioethers, esters, thioesters, carbonates, carbamates, amides, phosphates and oximes. In certain embodiments, a functional unit is converted to a more lipophilic moiety through acetylation or acylation(alkanoylation). In certain embodiments, a functional unit is converted to a more lipophilic moiety via esterification.

In certain embodiments, a parent drug of an HPP or HPC is a drug that can be used by itself or in combination with other drug(s) to treat pulmonary conditions (e.g. asthma, lower, and upper respiratory tract infections, chronic bronchitis, chronic obstructive pulmonary disease, emphysema, cystic fibrosis, pneumonia, sarcoidosis, and pulmonary fibrosis) or a related compound thereof. A related compound of a parent drug is a compound comprising the structure of the parent drug, a metabolite of the parent drug, or an agent that can be metabolized into the parent drug or a metabolite of the parent drug after an HPP or HPC penetrates one or more biological barriers. A related compound of a parent drug further includes a compound that is an analog or mimic of the parent drug or a metabolite of the parent drug, or an agent that can be metabolized into an analog or mimic of the parent drug or a metabolite of the parent drug, after an HPP or HPC penetrates one or more biological barriers.

The moiety of a parent drug or the related compound thereof can be further converted to a lipophilic moiety as described supra. The main classes of drugs that can be used to treat pulmonary conditions (e.g. asthma, lower, and upper respiratory tract infections, chronic bronchitis, chronic obstructive pulmonary disease, emphysema, cystic fibrosis, pneumonia, sarcoidosis, and pulmonary fibrosis) include, for example, antihistamines, β2-adrenergic receptor agonists, 5-lipoxygenase-activating protein (FLAP) inhibitors, 5-lipoxygenase inhibitors, leukotriene receptor antagonists, anti-inflammatory drugs, cough suppressants, decongestants, and antibiotics.

Examples of 5-lipoxygenase-activating protein (FLAP) inhibitors include, without limitation, MK-886 [3-(1-(4-Chlorobenzyl)-3-t-butylthio-5-isopropylindol-2-yl)-2,2-dimethylpropanoic acid], MK-0591 [3-(1-(4-chlorobenzyl-3-(t-butylthio)-5-(quinolin-2-ylmethoxy)indol-2-yl))-2,2-dimethyl propanoic acid], 2-cyclopentyl-2-[4-(quinolin-2-ylmethoxy)phenyl]acetic acid, and 3-[[1-(4-chlorobenzyl)-4-methyl-6-(5-phenylpyridin-2-yl)methoxy]-4,5-dihydro-1H-thiopyrano[2,3,4-c,d]indol-2-yl]-2,2-dimethylpropanoic acid.

Examples of 5-lipoxygenase inhibitors include without limitation, zileuton [(RS)—N-[1-(1-benzothien-2-yl)ethyl]-N-hydroxyurea], theophylline [1,3-dimethyl-7H-purine-2,6- dione], 2,6-dimethyl-4-[2-(4-fluorophenyl)ethenyl]phenol, 2,6-dimethyl-4-[2-(3-pyridyl)ethenyl]phenol, and 2,6-dimethyl-4-[2-(2-thienyl)ethenyl]phenol.

Examples of leukotriene receptor antagonists include, without limitation, montelukast {R-(E)-1-[[[-1-[3-[2-(7-chloro2-quinolinyl)ethenyl]phenyl]-3-[2-(1-hydroxy-1-methylethyl)phenyl]propyl]thio]methyl]cyclopropaneacetic acid}, 7-[3-(4-acetyl-3-hydroxy-2-propylphenoxy)-2-hydroxypropoxy]-4-oxo-8-propyl-4H-1-benzopyran-2-carboxylic acid, (E)-3-[[[3-[2-(7-chloro-2-quinolinyl)ethenyl]phenyl][[3-dimethylamino]-3-oxopropyl]thio]methyl]thio] propanoic acid sodium salt, 2(S)-hydroxyl-3(R)-carboxyethylthio)-3-[2-(8-phenyloctyl)phenyl]propanoic acid, 4-[4-[3-(4-acetyl-3-hydroxy-2-propylphenoxy)propylsulfonyl]phenyl]-4-oxo-butanoic acid, and 3-(3-(2-(7-chloro-2-quinolinyl)ethenyl)phenyl)((3-dimethylamino-3-oxopropyl)thio)methyl)thiopropanoic acid.

Examples of antihistamines include, without limitation, fexofenadine ((RS)-2-[4-[1-Hydroxy-4-[4-(hydroxy-diphenyl-methyl)-1-piperidyl]butyl]phenyl]-2-methyl-propanoic acid), clemastine ((2R)-2-{2-[(1R)-1-(4-chlorophenyl)-1-phenylethoxy]ethyl}-1-methylpyrrolidine), diphenhydramine (2-(diphenylmethoxy)-N,N-dimethylethanamine), doxylamine[(RS)—N,N-dimethyl-2-(1-phenyl-1-pyridine-2-yl-ethoxy)-ethanamine], desloratadine[8-chloro-6,11-dihydro-11-(4-piperdinylidene)-5H-benzo[5,6]cyclohepta[1,2-b]pyridine], Brompheniramine (3-(4-bromophenyl)-N,N-dimethyl-3-pyridin-2-yl-propan-1-amine), chlorophenamine [3-(4-chlorophenyl)-N,N-dimethyl-3-pyridin-2-yl-propan-1-amine, pheniramine, fluorpheniramine, dexchlorpheniramine (Polaramine), deschlorpheniramine, diphenliramine, iodopheniramine, Cromoglicic acid (5,5'-(2-hydroxypropane-1,3-diyl)bis(oxy)bis(4-oxo-4H-chromene-2-carboxylic acid), Loratadine [Ethyl 4-(8-chloro-5,6-dihydro-11H-benzo[5,6]cyclohepta[1,2-b]pyridin-11-ylidine)-1-piperidinecarboxylate, acrivastine [(E)-3-{6-[(E)-1-(4-methylphenyl)-3-pyrrolidine-1-yl-prop-1-enyl]pyridin-2-yl}prop-2-enoic acid], ebastine [4-(4-benzhydryloxy-1-piperidyl)-1-(4-tert-butylphenyl)butan-1-one], carebastine, promethazine [(RS)—N,N-dimethyl-1-(10H-phenothiazin-10-yl)propan-2-amine], and olopatadine [{(11Z)-11-[3-(dimethylamino)-propylidene]-6,11-dihydrodibenzo[b,e]oxepin-2-yl}acetic acid].

Examples of β2-adrenergic receptor agonists include, without limitation, albuterol [(RS)-4-[2-(tert-butylamino)-1-hydroxyethyl]-2-(hydroxymethyl)phenol], levosalbuterol [4-[(1R)-2-(tert-butylamino)-1-hydroxyethyl]-2-(hydroxymethyl)phenol], terbutaline [(RS)-5-[2-(tert-butylamino)-1-hydroxyethyl]benzene-1,3-diol], pirbuterol [(RS)-6-[2-(tert-butylamino)-1-hydroxyethyl]-2-(hydroxymethyl)pyridin-3-ol], procaterol [(±)-(1R,2S)-rel-8-Hydroxy-5-[1-hydroxy-2-(isopropylamino)butyl]-quinolin-2(1H)-one], metaproterenol [(RS)-5-[1-hydroxy-2-(isopropylamino)ethyl]benzene-1,3-diol], fenoterol [(RR, SS)-5-(1-hydroxy-2-{[2-(4-hydroxyphenyl)-1-methylethyl]amino}ethyl)benzene-1,3-diol], bitolterol mesylate [(RS)-[4-(1-Hydroxy-2-tert-butylamino-ethyl)-2-(4-methylbenzoyl)oxy-phenyl]4-methylbenzoate], ritodrine [4-((1R,2S)-1-hydroxy-2-{[2-(4-hydroxyphenyl)ethyl]amino}propyl)phenol], salmeterol [(RS)-2-(hydroxymethyl)-4-{1-hydroxy-2-[6-(4-phenylbutoxy)hexylamino]ethyl}phenol], formoterol [(RS,SR)—N-[2-hydroxy-5-[1-hydroxy-2-[1-(4-methoxyphenyl)propan-2-ylamino]ethyl]phenyl]formamide], bambuterol [(RS)-5-[2-(tert-butylamino)-1-hydroxyethyl]benzene-1,3-diyl bis (dimethylcarbamate)], clenbuterol [(RS)-1-(4-amino-3,5-dichlorophenyl)-2-(tert-butylamino)ethanol], and indacaterol [(R)-5-[2-[(5,6-Diethyl-2,3-dihydro-1H-inden-2-yl)amino]-1-hydroxyethyl]-8-hydroxyquinolin-2(1H)-one].

Examples of anti-inflammatory drugs include, without limitation, non-steroid anti-inflammatory agents ("NSAIAs," e.g. aspirin, ibuprofen, diflunisal, and diclofenac).

Examples of cough suppressants include, without limitation, dextromethorphan ((+)-3-methoxy-17-methyl-(9α, 13α,14α)-morphinan), tipepidine (3-(di-2-thienylmethylene)-1-methylpiperidine), cloperastine (1-[2-[(4-chlorophenyl)-phenyl-methoxy]ethyl]piperidine), benproperine (1-[2-(2-benzylphenoxy)-1-methylethyl]piperidine), dioxopromethazine (9,9-dioxopromethazine), promolate (2-morpholinoethyl-2-phenoxy-2-methylpropionate), fominoben (N-2-chloro-6-benzoyl-aminobenzyl-methylaminoacetyl-morpholine), and pentoxyverine (2-[2-(diethylamino)ethoxy]ethyl 1-phenylcyclopentanecarboxylate).

Examples of decongestants include, without limitation, ephedrine [(R, S)-2-(methylamino)-1-phenylpropan-1-ol], levomethamphetamine [(R)—N-methyl-1-phenyl-propan-2-amine], phenylephrine [(R)-3-[-1-hydroxy-2-(methylamino)ethyl]phenol], propylhexedrine [(RS)—N,α-dimethyl-cyclohexylethylamine], pseudoephedrine [(R*,R*)-2-methylamino-1-phenylpropan-1-ol], synephrine [4-[1-hydroxy-2-(methylamino)ethyl]phenol], and tetrahydrozoline [(RS)-2-(1,2,3,4-tetrahydronaphthalen-1-yl)-4,5-dihydro-1H-imidazole].

Examples of antibiotics include, without limitation, beta-lactam antibiotics, sulfonamides and quinolones. Examples of beta-lactam antibiotics include, but are not limited to, penicillin derivatives, cephalosporins, penems, monobactams, carbapenems, beta-lactamase inhibitors and combinations thereof. Examples of penicillin derivatives include, but are not limited to, aminopenicillins (e.g. amoxicillin, ampicillin, and epicillin); carboxypenicillins (e.g. carbenicillin, ticarcillin, and temocillin); ureidopenicillins (e.g. azlocillin, piperacillin and mezlocillin); mecillinam, sulbenicillin, benzathine penicillin, penicillin G (benzylpenicillin), penicillin V (phenoxymethylpenicillin), penicillin O (allylmercaptomethylpenicillinic), procaine penicillin, oxacillin, methicillin, nafcillin, cloxacillin, dicloxacillin, flucloxacillin, pivampicillin, hetacillin, becampicillin, metampicillin, talampicillin, co-amoxiclav (amoxicillin plus clavulanic acid), and piperacillin. Examples of cephalosporins include, but are not limited to, cephalexin, cephalothin, cefazolin, cefaclor, cefuroxime, cefamandole, cefotetan, cefoxitin, ceforanide, ceftriaxone, cefotaxime, cefpodoxime proxetil, ceftazidime, cefepime, cefoperazone, ceftizoxime, cefixime and cefpirome. Examples of penems include, without limitation, faropenem. Examples of monobactams include, without limitation, aztreonam and tigemonam. Examples of carbapenems include, but are not limited to, biapenem, •doripenem, ertapenem, •imipenem, •meropenem, •and panipenem. Examples of beta-lactamase inhibitors include, but are not limited to, tazobactam ([2S-(2alpha, 3beta,5alpha)]-3-Methyl-7-oxo-3-(1H-1,2,3-triazol-1-ylmethyl)-4-thia-1-azabicyclo[3.2.0]heptane-2-carboxylic acid 4,4-dioxide sodium salt), sulbactam (2S,5R)-3,3-dimethyl-7-oxo-4-thia-1-azabicyclo[3.2.0]heptane-2-carboxylic acid 4,4-dioxide sodium), and clavulanic acid ((2R,5R,Z)-3-(2-hydroxyethylidene)-7-oxo-4-oxa-1-azabicyclo[3.2.0]heptane-2-carboxylic acid). Other examples of antibiotics include, without limitation, [(N-benzyloxycarbonylamino)methyl]-phosphonic acid mono-(4-nitrophenyl) ester sodium salt, [(N-benzyloxycarbonylamino)methyl]-phosphonic acid mono-(3-pyridinyl) ester sodium salt, sulfanilamide (4-aminobenzenesulfonamide), sulfasalazine (6-oxo-3-(2-[4-(N-pyridin-2-ylsulfamoyl)phenyl]hydrazono) cyclohexa-1,4-dienecarboxylic acid), 1-cyclopropyl-6-fluoro-4-oxo-7-piperazin-1-yl-quinoline-3-carboxylic acid, and nalidixic acid (1-ethyl-7-methyl-4-oxo-[1,8]naphthyridine-3-carboxylic acid).

Examples of sulfonamides include, without limitation, sulfaisodimidine, sulfanilamide, sulfadiazine, sulfisoxazole, sulfamethoxazole, sulfadimethoxine, sulfamethoxypyridazine, sulfacetamide, sulfadoxine, acetazolamide, bumetanide, chlorthalidone, clopamide, furosemide, hydrochlorothiazide, indapamide, mefruside, metolazone, xipamide, dichlorphenamide, dorzolamide, acetazolamide, ethoxzolamide, sultiame, zonisamide, mafenide, celecoxib, darunavir, probenecid, sulfasalazine, and sumatriptan.

Examples of quinolones include, without limitation, cinoxacin, flumequine, nalidixic acid, oxolinic acid, piromidic acid, pipemidic acid, rosoxacin, ciprofloxacin, enoxacin, fleroxacin, lomefloxacin, nadifloxacin, norfloxacin, ofloxacin, pefloxacin, rufloxacin, balofloxacin, gatifloxacin, grepafloxacin, levofloxacin, moxifloxacin, pazufloxacin, sparfloxacin, temafloxacin, tosufloxacin, clinafloxacin, gemifloxacin, sitafloxacin, trovafloxacin, prulifloxacin, garenoxacin, ecinofloxacin, delafloxacin and nalidixic acid.

Transportational Unit

A transportational unit of an HPP comprises a protonatable amine group that is capable of facilitating the transportation or crossing of the HPP through one or more biological barriers (e.g., >about 20 times, >about 50 times, >about 100 times, >about 300 times, >about 500 times, >about 1,000 times or more faster than the parent drug). In certain embodiments, the protonatable amine group is substantially protonated at a physiological pH. In certain embodiments, the amine group can be reversibly protonated. In certain embodiments, a transportational unit may or may not be cleaved from the functional unit after the penetration of HPP through one or more biological barriers.

In certain embodiments, a functional unit may also contain one or more transportational units, especially for parent drugs that have at least a free amino group. In certain embodiments, when a functional unit contains one or more transportational units, the functional unit is modified such that only one or two amine groups are protobatable. In certain embodiments, a functional unit contains one or two amine groups. These functional units can be modified or can be used as HPCs without further modifications. Examples of compounds that have one or two amine groups include, without limitation, pheniramine, fluorpheniramine, chlorpheniramine, dexchlorpheniramine (Polaramine), deschlorpheniramine, dipheniramine, iodopheniramine, albuterol, levoalbuterol, pirbuterol, procaterol, bitolterol mesylate, ritodrine, salmeterol, formoterol, bambuterol, clenbuterol, and indacaterol.

In certain embodiments, the protonatable amine group is selected from the group consisting of pharmaceutically acceptable substituted and unsubstituted amine groups, Structure W-1, Structure W-2, Structure W-3, Structure W-4, Structure W-5, Structure W-6, Structure W-7, Structure W-8, Structure W-9, Structure W-10, Structure W-11, Structure W-12, Structure W-13, Structure W-14, Structure W-15, Structure W-16, Structure W-17 and Structure W-18:

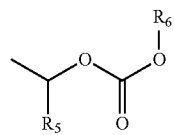

Structure Wa

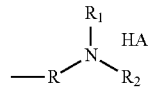

Structure W-1

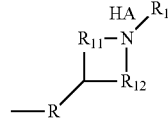

Structure W-2

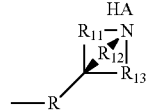

Structure W-3

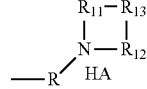

Structure W-4

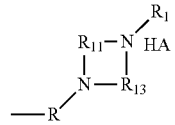

Structure W-5

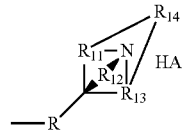

Structure W-6

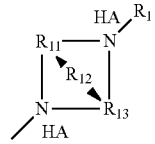

Structure W-7

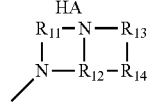

Structure W-8

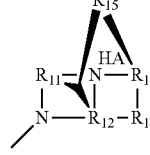

Structure W-9

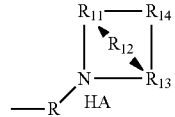

Structure W-10

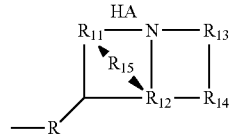

Structure W-11

-continued

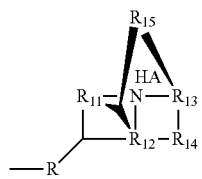
Structure W-12

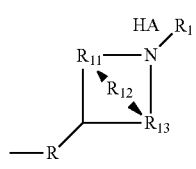
Structure W-13

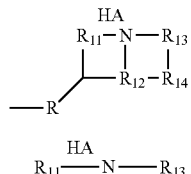
Structure W-14

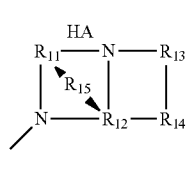
Structure W-15

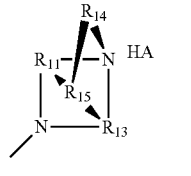
Structure W-16

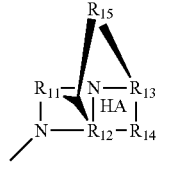
Structure W-17

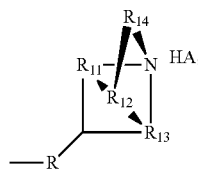
Structure W-18

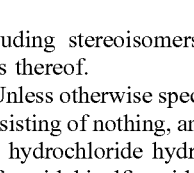

including stereoisomers and pharmaceutically acceptable salts thereof.

Unless otherwise specified, HA is selected from the group consisting of nothing, and pharmaceutically acceptable acid, e.g. hydrochloride hydrobromide, hydroiodide, nitric acid, sulfic acid, bisulfic acid, phosphoric acid, phosphorous acid, phosphonic acid, isonicotinic acid, acetic acid, lactic acid, salicylic acid, citric acid, tartaric acid, pantothenic acid, bitartaric acid, ascorbic acid, succinic acid, maleic acid, gentisinic acid, fumaric acid, gluconic acid, glucaronic acid, saccharic acid, formic acid, benzoic acid, glutamic acid, methanesulfonic acid, ethanesulfonic acid, benzensulfonic acid, p-toluenesulfonic acid and pamoic acid;

R is selected from the group consisting of nothing, $CH_2C(=O)OR_6$, substituted and unsubstituted alkyl, substituted and unsubstituted cycloalkyl, substituted and unsubstituted heterocycloalkyl, substituted and unsubstituted alkoxyl, substituted and unsubstituted perfluoroalkyl, substituted and unsubstituted alkyl halide, substituted and unsubstituted alkenyl, substituted and unsubstituted alkynyl, substituted and unsubstituted aryl, and substituted and unsubstituted heteroaryl, wherein any $CH_2$ in R may be further replaced with O, S, P, $NR_6$, or any other pharmaceutically acceptable groups;

$R_6$ is independently selected from the group consisting of H, F, Cl, Br, $Na^+$, $K^+$, $C(=O)R_5$, 2-oxo-1-imidazolidinyl, phenyl, 5-indanyl, 2,3-dihydro-1H-inden-5-yl, 4-hydroxy-1,5-naphthyridin-3-yl, substituted and unsubstituted alkyl, substituted and unsubstituted cycloalkyl, substituted and unsubstituted heterocycloalkyl, substituted and unsubstituted alkenyl, substituted and unsubstituted alkynyl, substituted and unsubstituted alkyloxyl, substituted and unsubstituted cycloalkyloxyl, substituted and unsubstituted aryl, substituted and unsubstituted heteroaryl, —C(=O)—W, -$L_1$-$L_4$-$L_2$-W, and W;

$R_5$ is independently selected from the group consisting of H, $C(=O)NH_2$, $CH_2CH_2OR_6$, $CH_2CH_2N(CH_3)_2$, $CH_2CH_2N(CH_2CH_3)_2$, Cl, F, Br, I, substituted and unsubstituted alkyl, substituted and unsubstituted cycloalkyl, substituted and unsubstituted heterocycloalkyl, substituted and unsubstituted alkyloxyl, substituted and unsubstituted cycloalkyloxyl, substituted and unsubstituted aryl, substituted and unsubstituted heteroaryl, substituted and unsubstituted alkylcarbonyl, substituted and unsubstituted alkylamino, —C(=O)—W, $L_1$-$L_4$-$L_2$-W, and W;

$L_1$ being selected from the group consisting of nothing, O, S, —O-$L_3$-, —S-$L_3$-, —N($L_3$)-, —N($L_3$)-$CH_2$—O, —N($L_3$)-$CH_2$—N($L_5$)-, —O—$CH_2$—O—, —O—CH($L_3$)-O, and —S—CH($L_3$)-O—;

$L_2$ being selected from the group consisting of nothing, O, S, —O-$L_3$-, —S-$L_3$-, —N($L_3$)-, —N($L_3$)-$CH_2$—O, —N($L_3$)-$CH_2$—N($L_5$)-, —O—$CH_2$—O—, —O—CH($L_3$)-O, —S—CH($L_3$)-O—, —O-$L_3$-, —N-$L_3$-, —S-$L_3$-, —N($L_3$)-$L_5$- and $L_3$;

$L_4$ being selected from the group consisting of nothing, C=O, C=S,

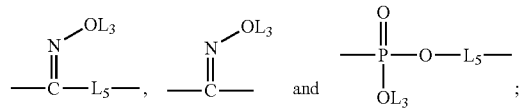

for each $L_1$, $L_2$, and $L_4$, each $L_3$ and $L_5$ being independently selected from the group consisting of nothing, H, $CH_2C(=O)OL_6$, substituted and unsubstituted alkyl, substituted and unsubstituted cycloalkyl, substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, P, $NL_3$, or any other pharmaceutically acceptable groups;

each $L_6$ and each $L_7$ being independently selected from the group consisting of H, OH, Cl, F, Br, I, substituted and unsubstituted alkyl, substituted and unsubstituted cycloalkyl, and substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, N, P(O)OL$_6$, CH=CH, C≡C, CHL$_6$, CL$_6$L$_7$, aryl, heteroaryl, or cyclic groups;

W is selected from the group consisting of H, substituted and unsubstituted alkyl, substituted and unsubstituted cycloalkyl, substituted and unsubstituted heterocycloalkyl, substituted and unsubstituted alkyloxy, substituted and unsubstituted alkenyl, substituted and unsubstituted alkynyl, substituted and unsubstituted aryl, substituted and unsubstituted heteroaryl, the protonatable amine group, pharmaceutically acceptable substituted and unsubstituted amine groups, Structure Wa, Structure W-1, Structure W-2, Structure W-3, Structure W-4, Structure W-5, Structure W-6, Structure W-7, Structure W-8, Structure W-9, Structure W-10, Structure W-11, Structure W-12, Structure W-13, Structure W-14, Structure W-15, Structure W-16, Structure W-17 and Structure W-18;

R$_1$ and R$_2$ are independently selected from the group consisting of H, substituted and unsubstituted alkyl, substituted and unsubstituted cycloalkyl, substituted and unsubstituted heterocycloalkyl, substituted and unsubstituted alkyloxyl, substituted and unsubstituted alkenyl and unsubstituted alkynyl, substituted and unsubstituted aryl and substituted and unsubstituted heteroaryl residues;

R$_{11}$-R$_{15}$ are independently selected from the group consisting of nothing, H, CH$_2$C(=O)OR$_{11}$, substituted and unsubstituted alkyl, substituted and unsubstituted cycloalkyl, substituted and unsubstituted heterocycloalkyl, substituted and unsubstituted alkoxyl, substituted and unsubstituted perfluoroalkyl, substituted and unsubstituted alkyl halide, substituted and unsubstituted alkenyl, substituted and unsubstituted alkynyl, substituted and unsubstituted aryl, and substituted and unsubstituted heteroaryl; and any CH$_2$ groups may be replaced with O, S, or NH.

Linker

In certain embodiments, a linker covalently linking a functional unit and a transportational unit of an HPP comprises a bond that is capable of being cleaved after the HPP penetrates across one or more biological barriers. The cleavable bond comprises, for example, a covalent bond, an ether, thioether, amide, ester, thioester, carbonate, carbamate, phosphate or oxime bond.

HPP Structures

An HPP of a parent drug or a related compound of the parent drug has the following Structure L-1:

Structure L-1

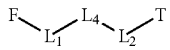

including stereoisomers and pharmaceutically acceptable salts thereof;

F being a functional unit, for example, selected from the group consisting of antihistamines, β2-adrenergic receptor agonists, 5-lipoxygenase-activating protein (FLAP) inhibitors, 5-lipoxygenase inhibitors, leukotriene receptor antagonists, anti-inflammatory drugs, cough suppressants, decongestants and antibiotics;

T being a transportational unit, for example, selected from the group consisting of protonatable amine groups, pharmaceutically acceptable substituted and unsubstituted primary amine groups, pharmaceutically acceptable substituted and unsubstituted secondary amine groups, and pharmaceutically acceptable substituted and unsubstituted tertiary amine groups, Structure W-1, Structure W-2, Structure W-3, Structure W-4, Structure W-5, Structure W-6, Structure W-7, Structure W-8, Structure W-9, Structure W-10, Structure W-11, Structure W-12, Structure W-13, Structure W-14, Structure W-15, Structure W-16, Structure W-17 and Structure W-18 as defined supra;

L$_1$, L$_2$, and L$_4$ are defined the same as supra, in certain embodiments, -L$_1$-L$_4$-L$_2$- is selected from the group consisting of nothing, —O—, —X—, —O—X—, —N—X—, —S—X—, —X$_5$—, —O—X$_5$—, —N—X$_5$—, —S—X$_5$—, —O—X$_7$—, —O—C(=O)—, —NH—C(=O)—, —C(=O)—, —C(=O)—O—, —C(=O)—N—, and C(=O)—X—;

X being selected from the group consisting of nothing, C(=O), OC(=O), CH$_2$, CH, S, NH, NR$_6$, and O;

X$_5$ being selected from the group consisting of nothing, C(=O), C(=S), OC(=O), CH$_2$, CH, S, O and NR$_5$; and X$_7$ is selected from the group consisting of nothing, C(=O), C(=S), OC(=O), CH$_2$, CH, S, O and NR$_5$.

An HPP of a drug that can be used to treat pulmonary conditions (e.g. asthma, lower, and upper respiratory tract infections, chronic bronchitis, chronic obstructive pulmonary disease, emphysema, cystic fibrosis, pneumonia, sarcoidosis, and pulmonary fibrosis) or a related compound thereof comprises, for example, a structure selected from the group consisting of Structure FLAP-1, Structure FLAP-2, Structure FLAP-3, Structure FLAP-4, Structure FLAP-5, Structure FLAP-6, Structure 5-LI-1-, Structure 5-LI-2, Structure 5-LI-3, Structure 5-LI-4, Structure 5-LI-5, Structure 5-LI-6, Structure 5-LI-7, Structure 5-LI-8, Structure LRA-1, Structure LRA-2, Structure LRA-3, Structure LRA-4, Structure LRA-5, Structure LRA-6, Structure ARA-1, Structure ARA-2, Structure ARA-3, Structure ARA-4, Structure ARA-5, Structure ARA-6, Structure ARA-7, Structure ARA-8, Structure ARA-9, Structure ARA-10, Structure ARA-11, Structure ARA-12, Structure ARA-13, Structure ARA-14, Structure AH-1, Structure AH-2, Structure AH-3, Structure AH-4, Structure AH-5, Structure AH-6, Structure AH-7, Structure AH-8, Structure AH-9, Structure AH-10, Structure AH-11, Structure AH-12, Structure AH-13, Structure AH-14, Structure AH-15, Structure AH-16, Structure AH-17, Structure AH-18, Structure AH-19, Structure AH-20, Structure CS-1, Structure CS-2, Structure CS-3, Structure CS-4, Structure CS-5, Structure CS-6, Structure CS-7, Structure CS-8, Structure DEC-1, Structure DEC-2, Structure DEC-3, Structure DEC-4, Structure DEC-5, Structure DEC-6, Structure NSAID-1, Structure NSAID-2, Structure NSAID-3, Structure NSAID-4, Structure NSAID-5, Structure NSAID-6, Structure NSAID-7, Structure NSAID-8, Structure NSAID-9, Structure NSAID-10, Structure NSAID-11, Structure NSAID-12, Structure NSAID-13, and Structure AB-1:

Structure FLAP-1
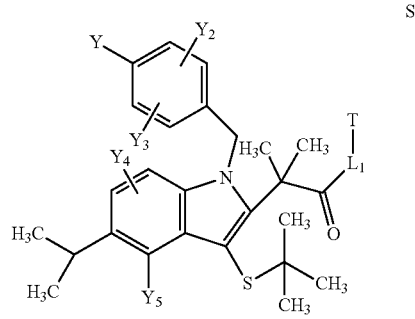
Structure FLAP-2
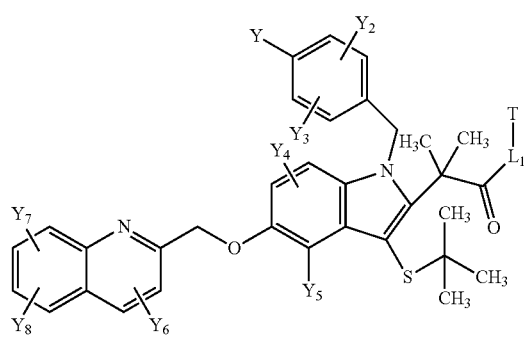
Structure FLAP-3
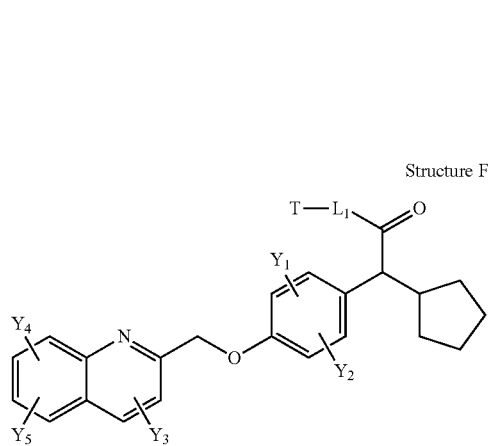
Structure FLAP-4
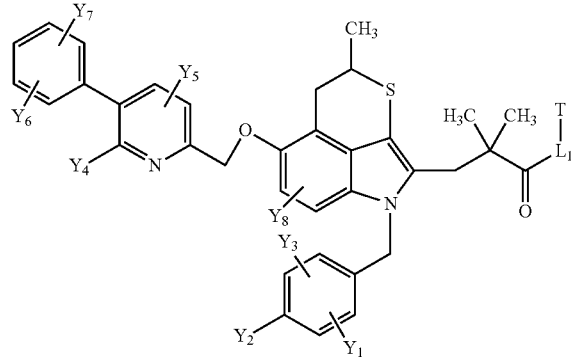
-continued
Structure FLAP-5
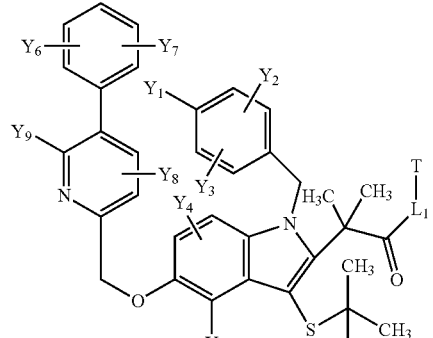
Structure FLAP-6
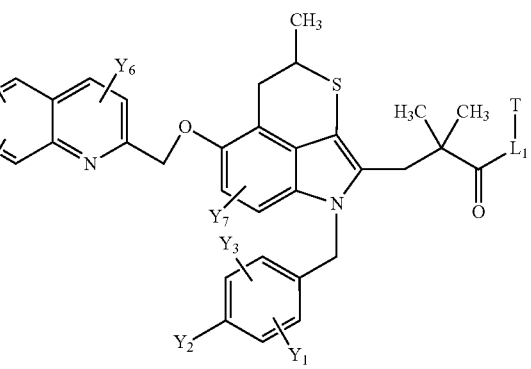
Structure 5-LI-1
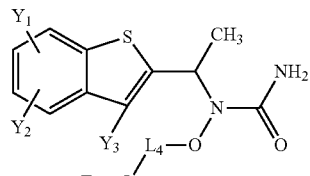
Structure 5-LI-2
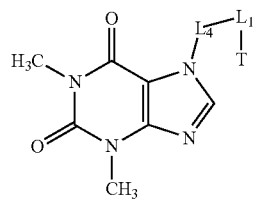
Structure 5-LI-3
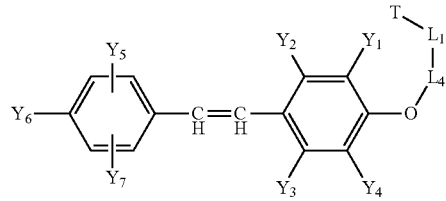
Structure 5-LI-4
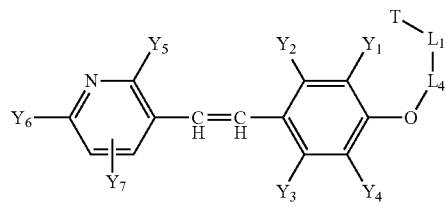

-continued
Structure 5-LI-5
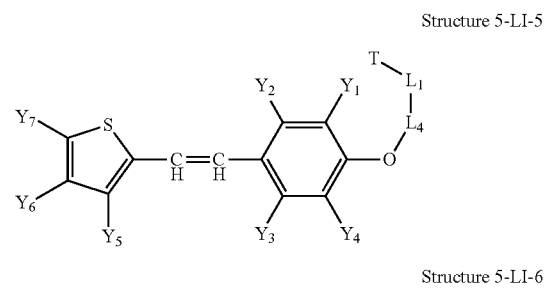
Structure 5-LI-6
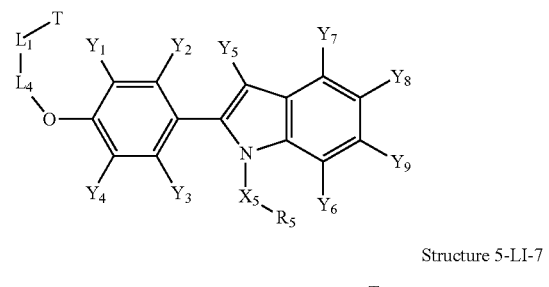
Structure 5-LI-7
Structure 5-LI-8
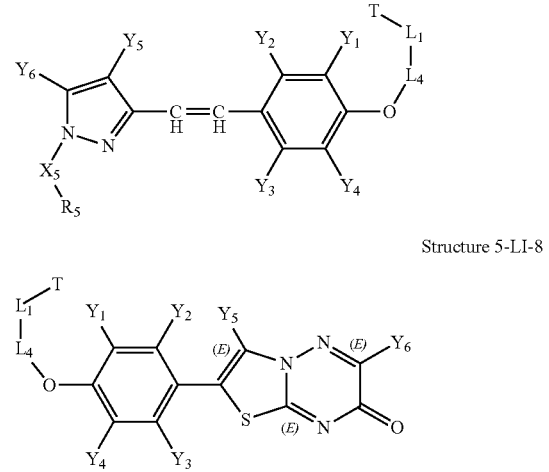
Structure LRA-1
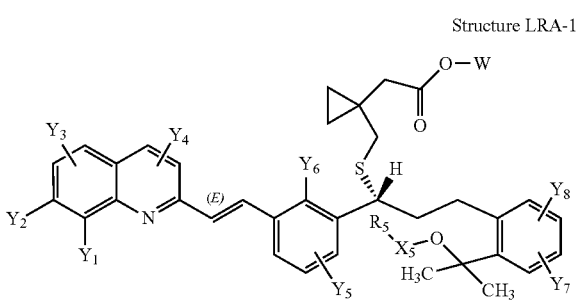
Structure LRA-2
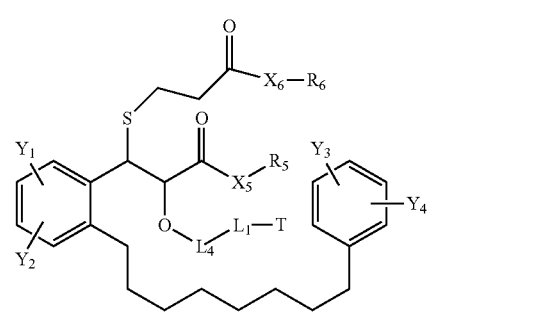
-continued
Structure LRA-3
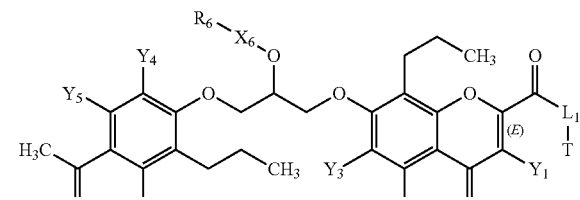
Structure LRA-4
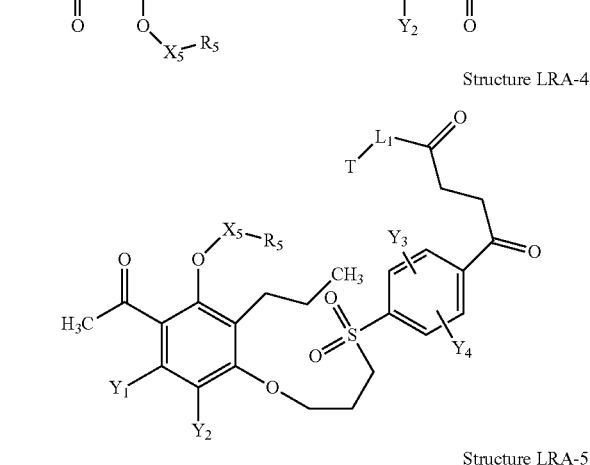
Structure LRA-5
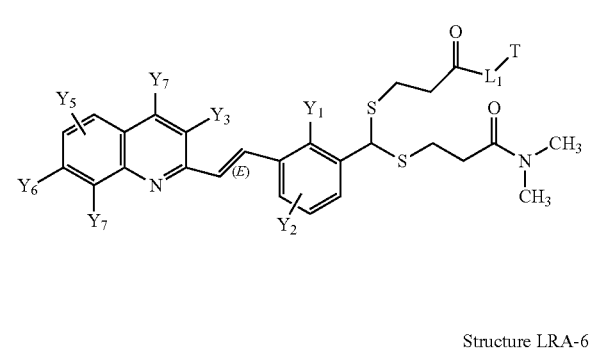
Structure LRA-6
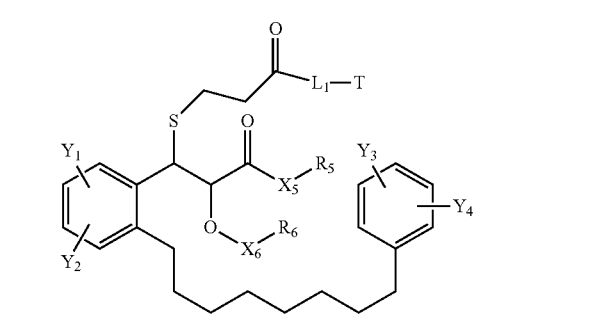
Structure ARA-1
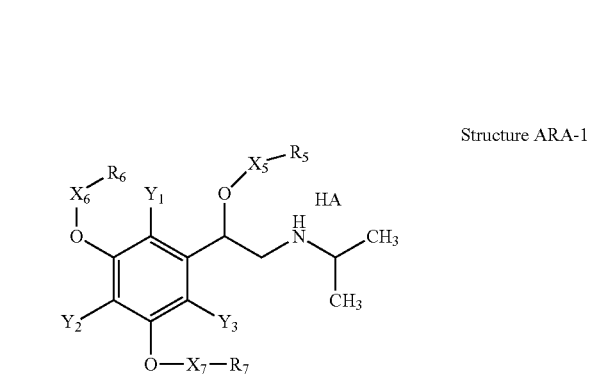

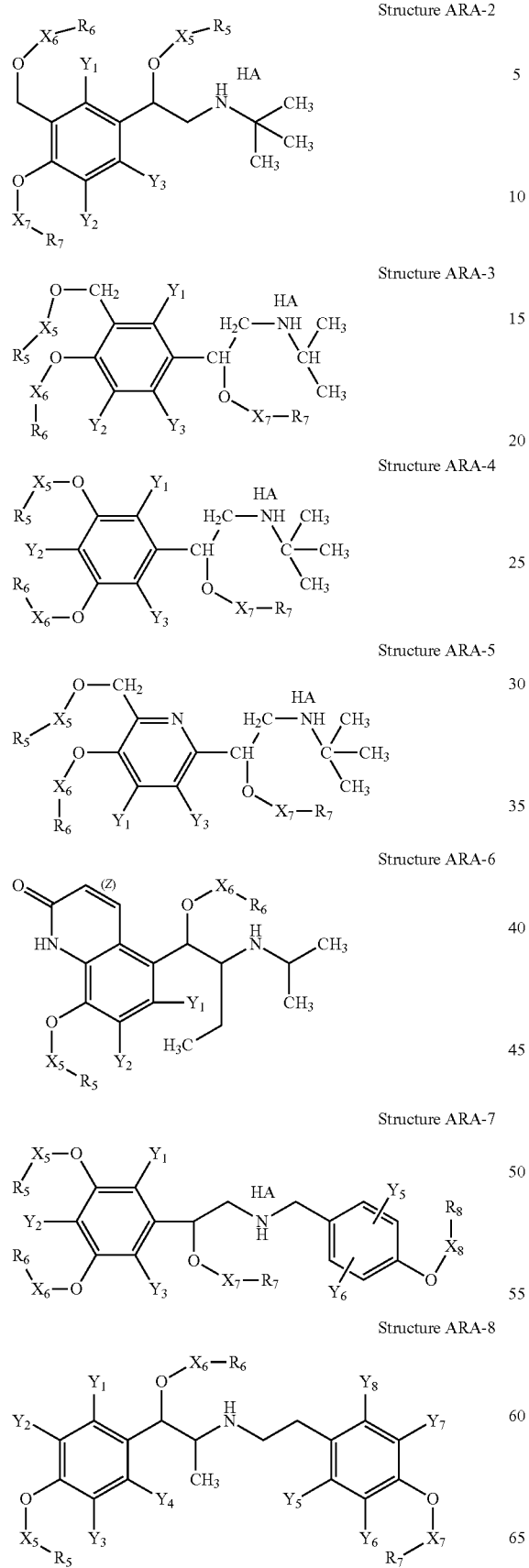
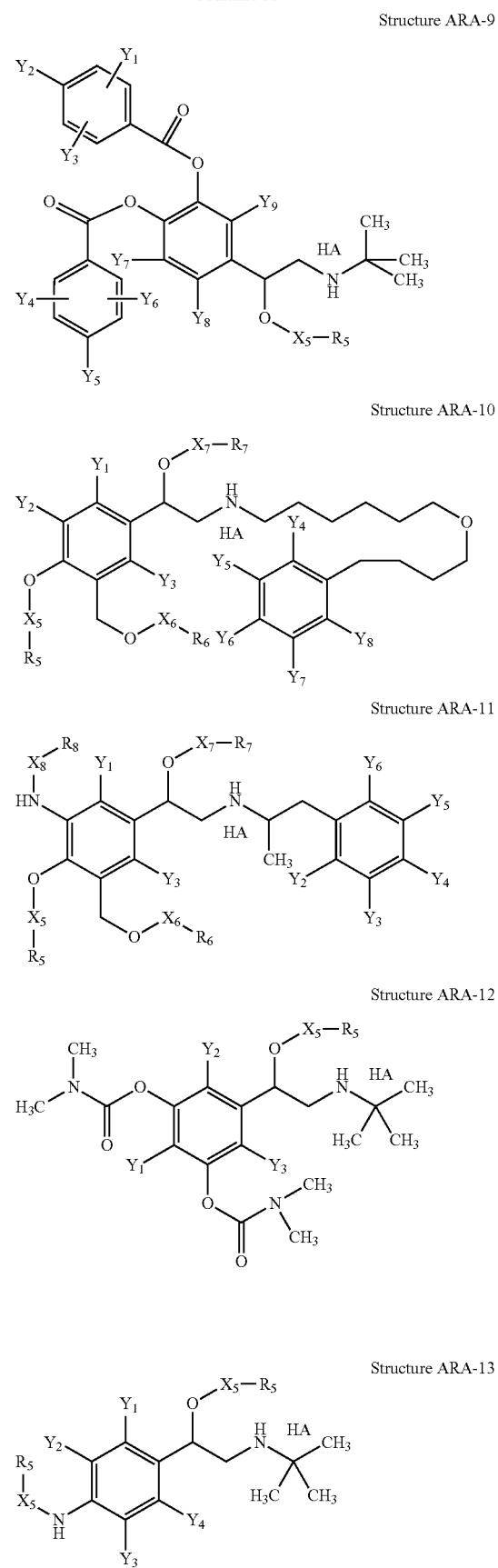

Structure ARA-14
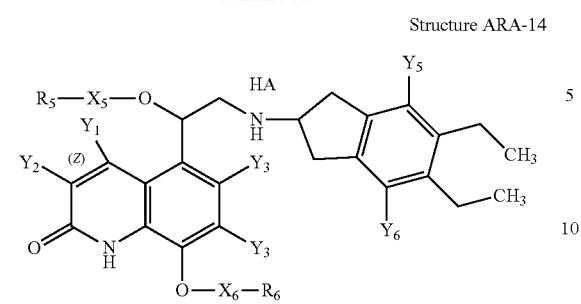
Structure AH-1
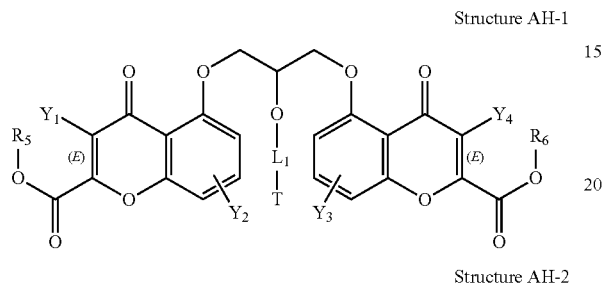
Structure AH-2
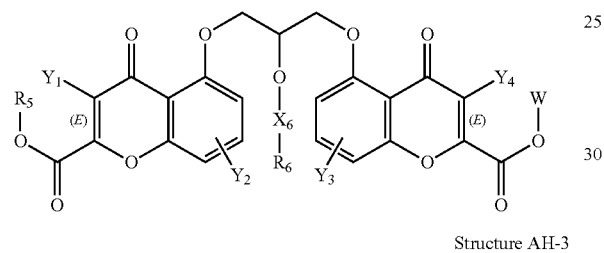
Structure AH-3
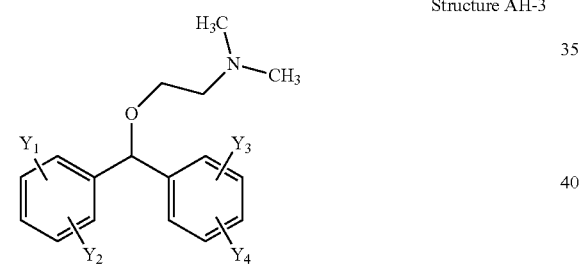
Structure AH-4
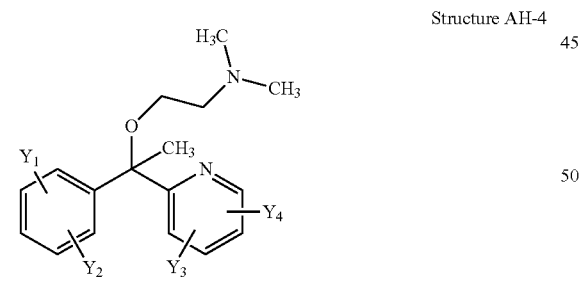
Structure AH-5
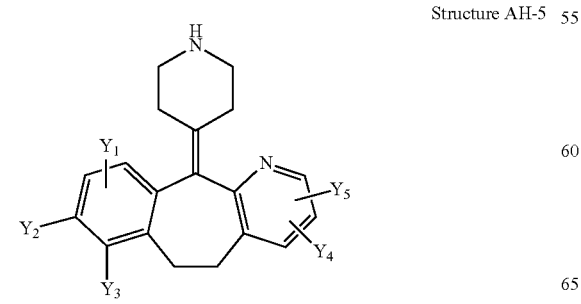
Structure AH-6
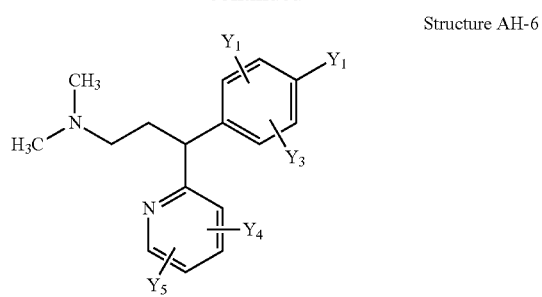
Structure AH-7
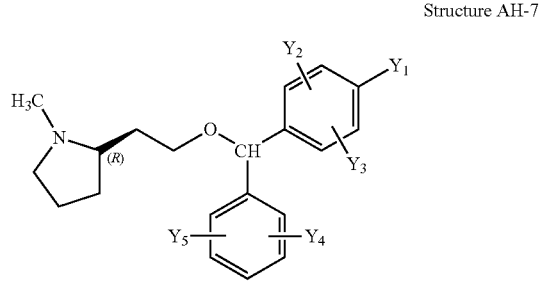
Structure AH-8
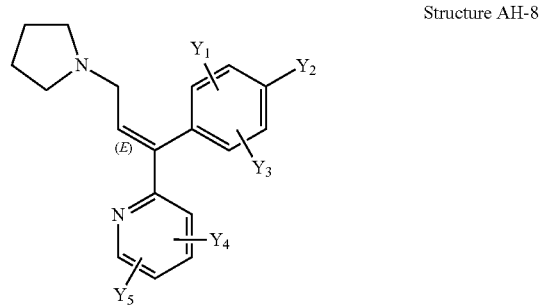
Structure AH-9
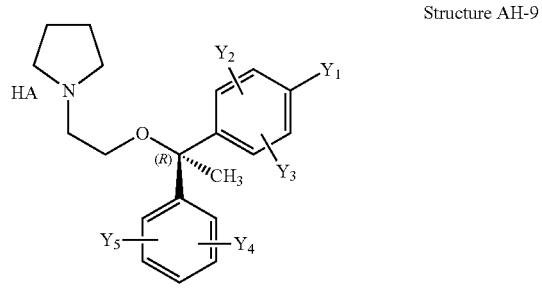
Structure AH-10
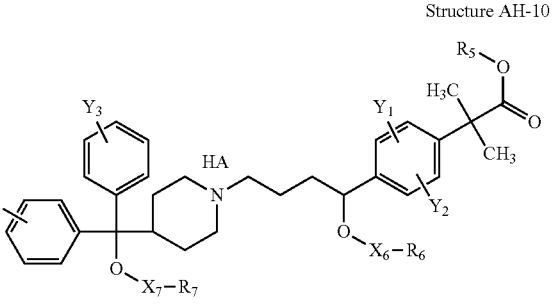

Structure AH-11
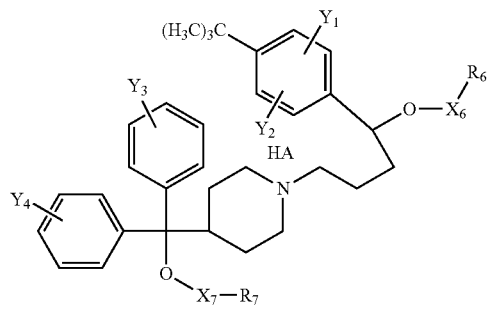
Structure AH-12
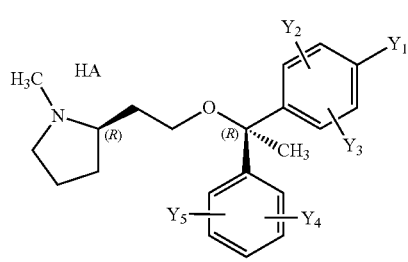
Structure AH-13
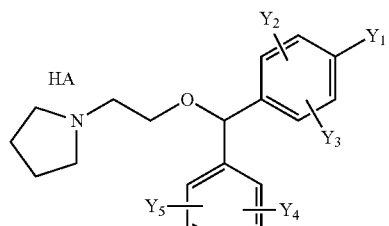
Structure AH-14
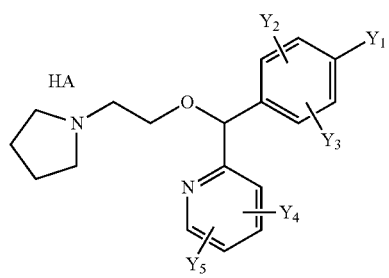
Structure AH-15
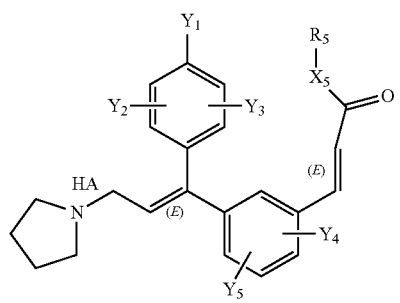
Structure AH-16
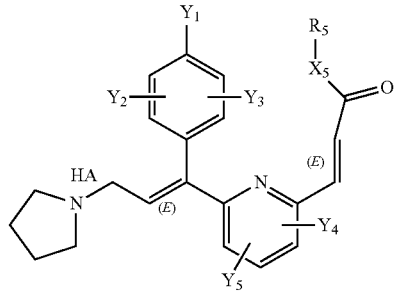
Structure AH-17
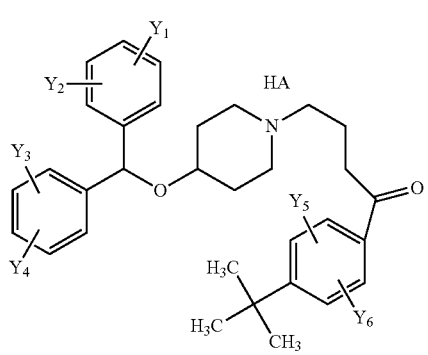
Structure AH-18
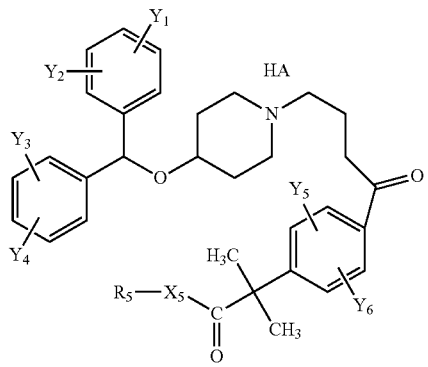
Structure AH-19
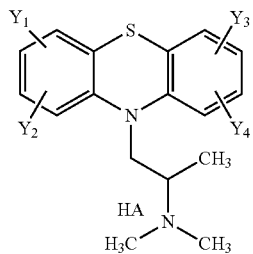
Structure AH-20

-continued
Structure CS-1
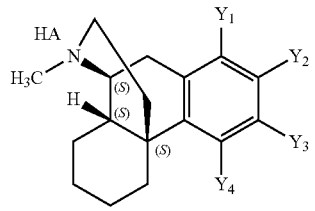
Structure CS-2
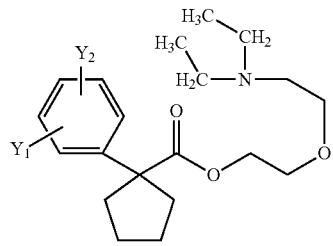
Structure CS-3
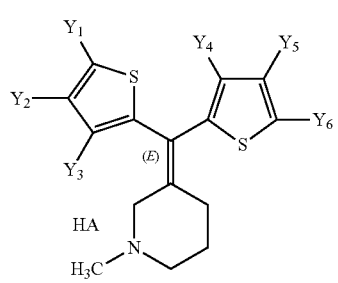
Structure CS-4
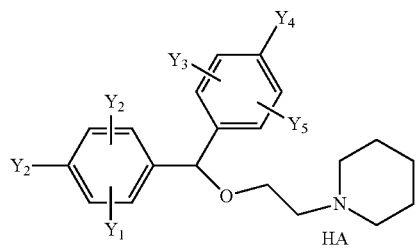
Structure CS-5
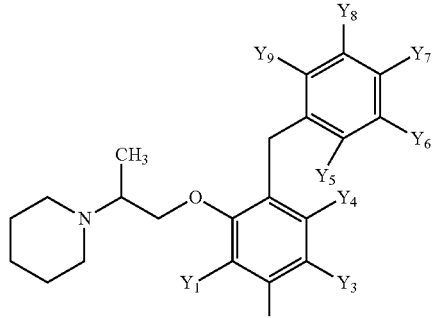
Structure CS-6
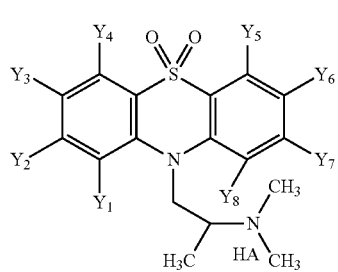
-continued
Structure CS-7
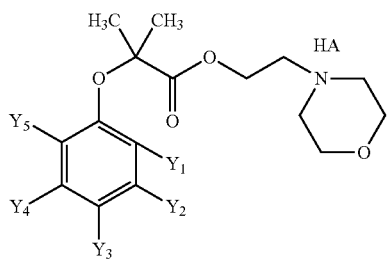
Structure CS-8
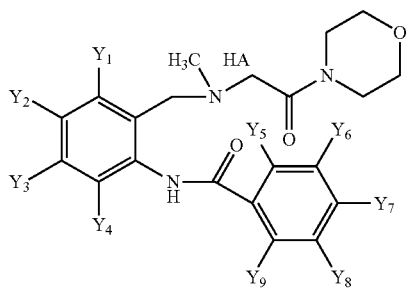
Structure DEC-1
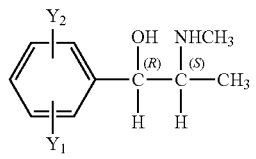
Structure DEC-2
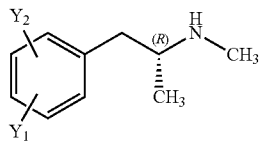
Structure DEC-3
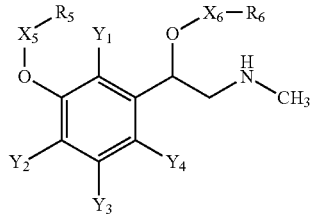
Structure DEC-4
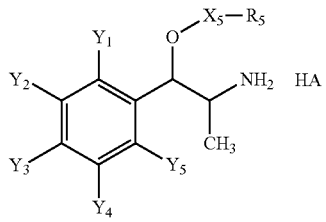
Structure DEC-5
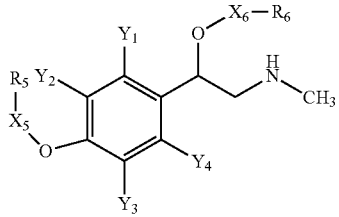

Structure DEC-6
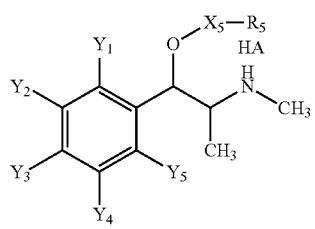
Structure NSAID-1
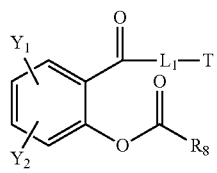
Structure NSAID-2
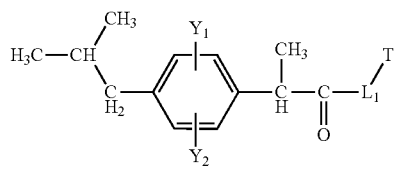
Structure NSAID-3
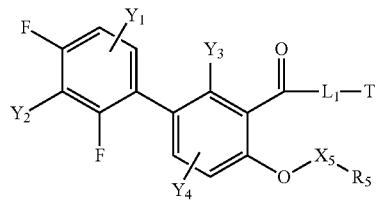
Structure NSAID-4
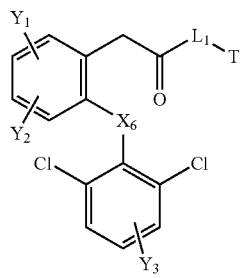
Structure NSAID-5
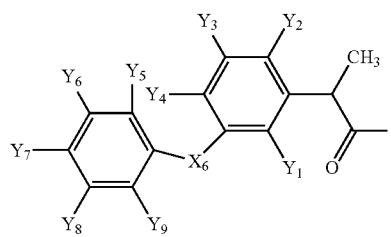
Structure NSAID-6
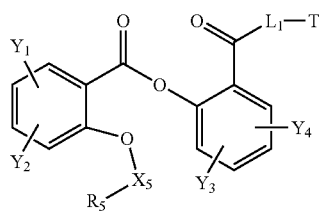
Structure NSAID-7
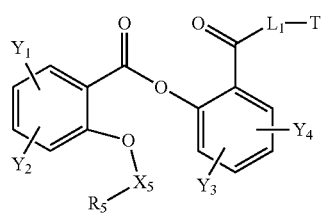
Structure NSAID-8
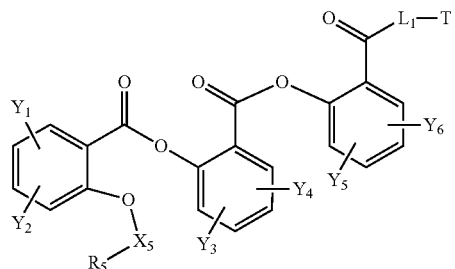
Structure NSAID-9
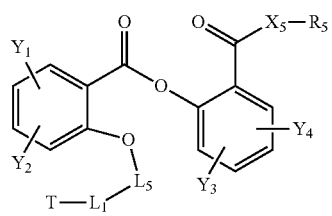
Structure NSAID-10
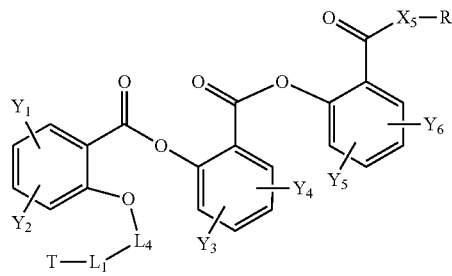
Structure NSAID-11
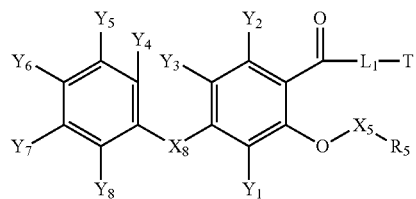
Structure NSAID-12
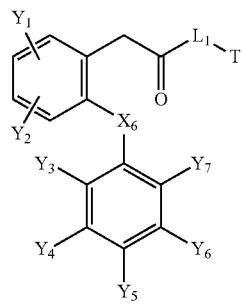

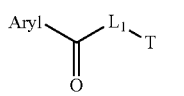
Structure NSAID-13

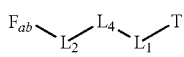
Structure AB-1 including stereoisomers and pharmaceutically acceptable salts thereof;

Aryl- is a functional unit of a HPP of an anti-inflammatory drug or an anti-inflammatory drug-related compound, examples of Aryl- include, without limitation, Aryl-1, Aryl-2, Aryl-3, Aryl-4, Aryl-5, Aryl-6, Aryl-7, Aryl-8, Aryl-9, Aryl-10, Aryl-11, Aryl-12, Aryl-13, Aryl-14, Aryl-15, Aryl-16, Aryl-17, Aryl-18, Aryl-19, Aryl-20, Aryl-21, Aryl-22, Aryl-23, Aryl-24, Aryl-25, Aryl-26, Aryl-27, Aryl-28, Aryl-29, Aryl-30, Aryl-31, Aryl-32, Aryl-33, Aryl-34, Aryl-35, Aryl-36, Aryl-37, Aryl-38, Aryl-39, Aryl-40, Aryl-41, Aryl-42, Aryl-43, Aryl-44, Aryl-45, Aryl-46, Aryl-47, Aryl-48, Aryl-49, Aryl-50, Aryl-51, Aryl-52, Aryl-53, Aryl-54, Aryl-55, Aryl-56, Aryl-57, Aryl-58, Aryl-59, Aryl-60, Aryl-61, Aryl-62, Aryl-63, Aryl-64, Aryl-65, Aryl-66, Aryl-67, Aryl-68, Aryl-69, Aryl-70, and Aryl-71:

Aryl-1
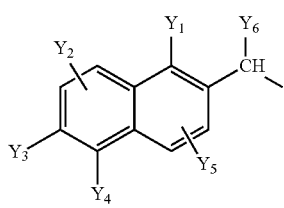

Aryl-2
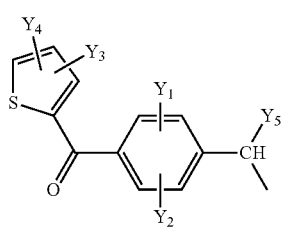

Aryl-3
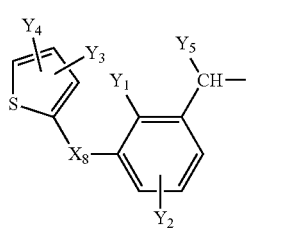

Aryl-4
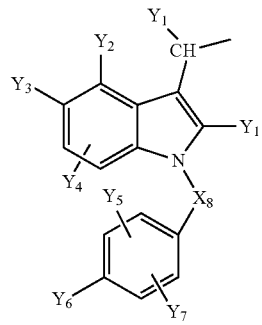

Aryl-5
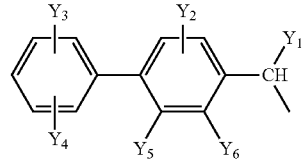

Aryl-6
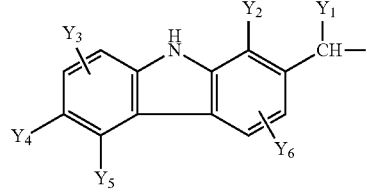

Aryl-7
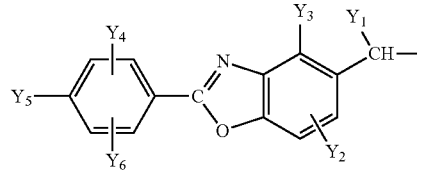

Aryl-8
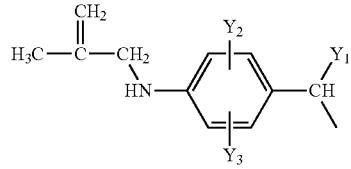

Aryl-9
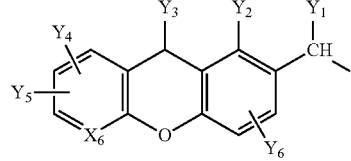

Aryl-10
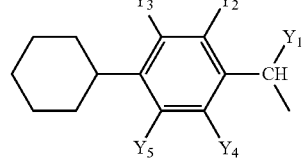

Aryl-11
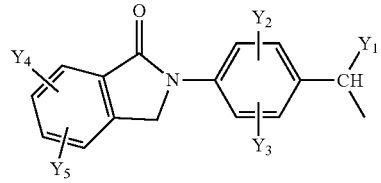

Aryl-12
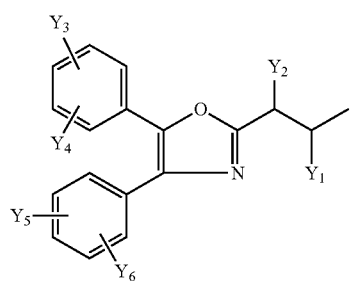
Aryl-13
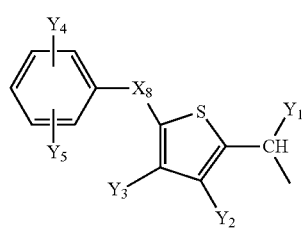
Aryl-14
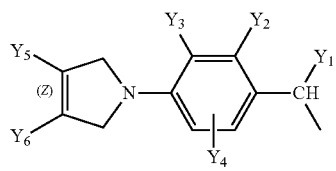
Aryl-15
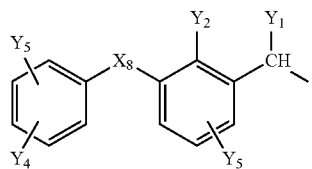
Aryl-16
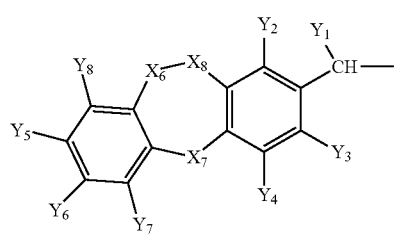
Aryl-17
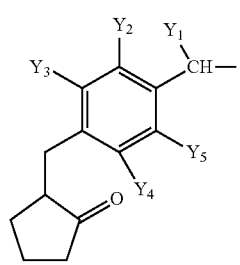
Aryl-18
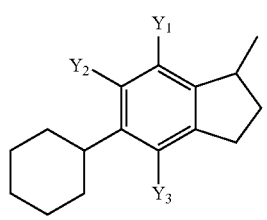
Aryl-19
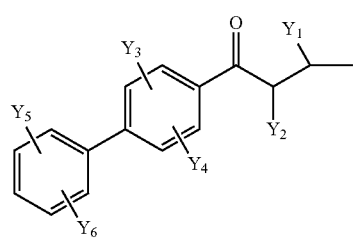
Aryl-20
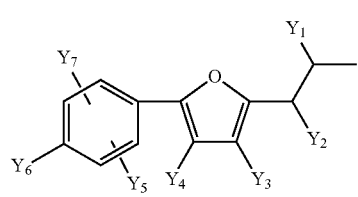
Aryl-21
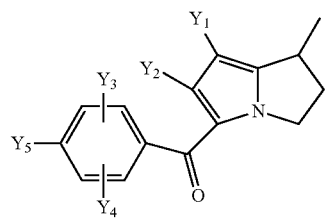
Aryl-22
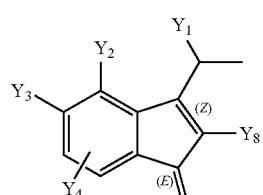
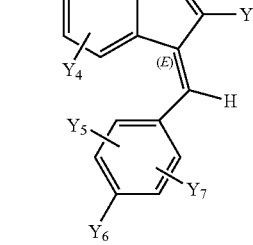
Aryl-23
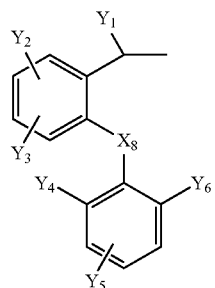
Aryl-24
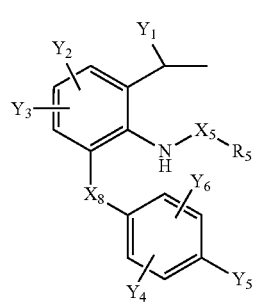

-continued
Aryl-25
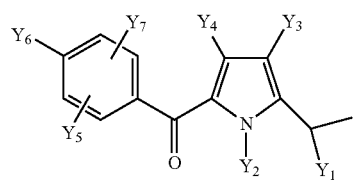
Aryl-26
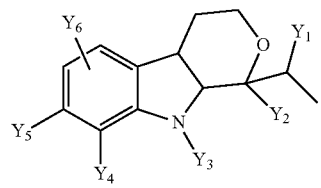
Aryl-27
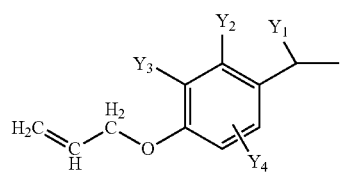
Aryl-28
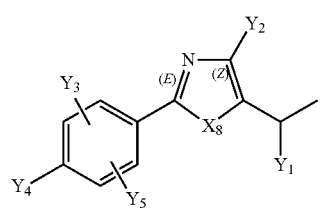
Aryl-29
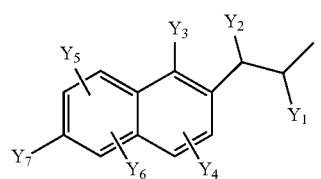
Aryl-30
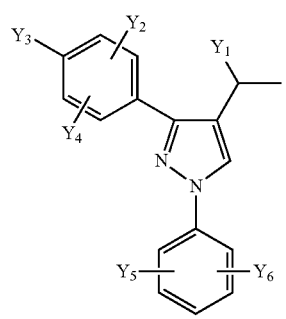
Aryl-31
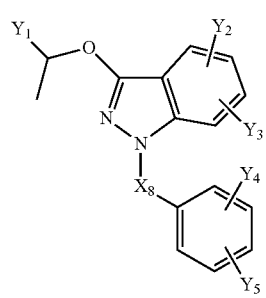
Aryl-32
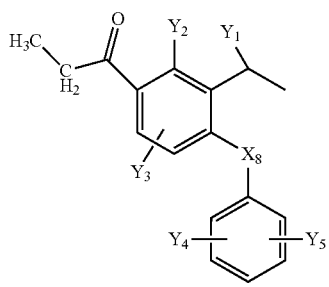
Aryl-33
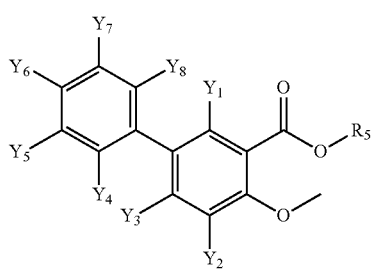
Aryl-34
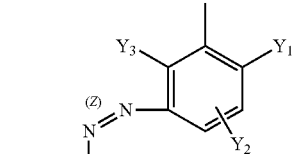
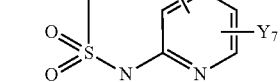
Aryl-35
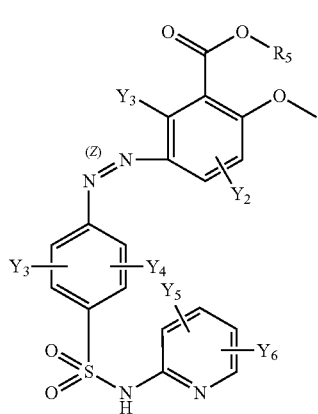

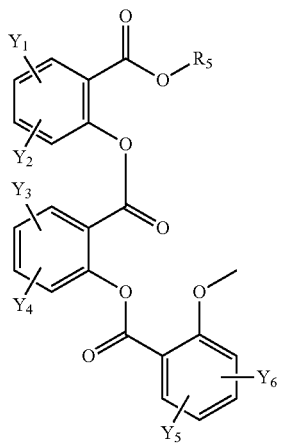
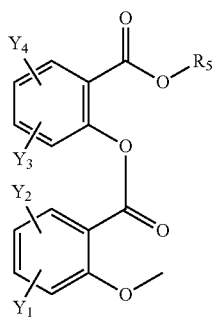
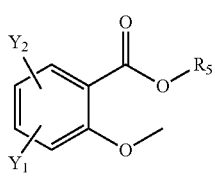
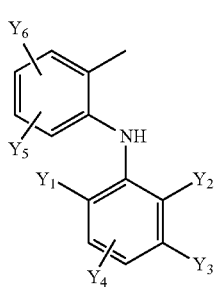
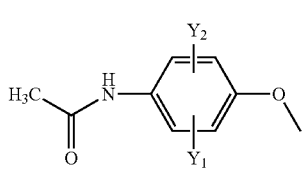
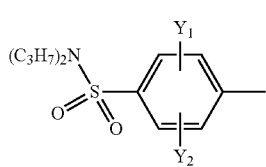
Aryl-36 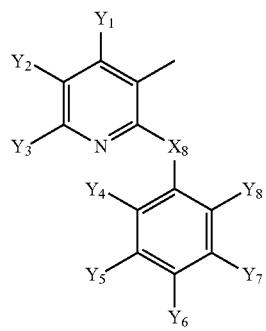
Aryl-37
Aryl-38 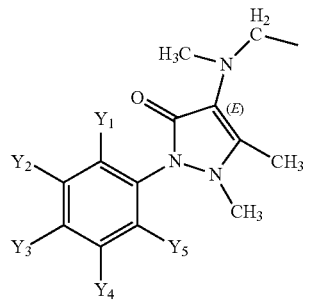
Aryl-39
Aryl-40 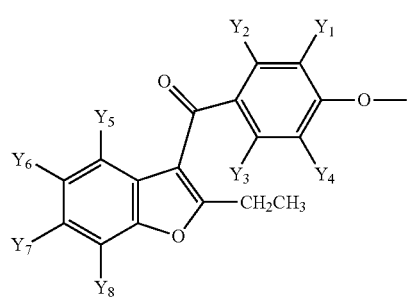
Aryl-41
Aryl-42
Aryl-43 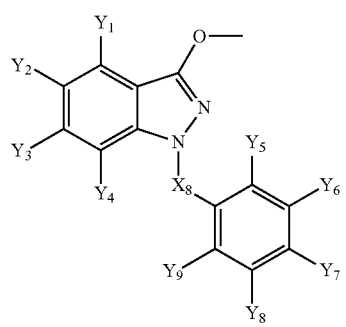
Aryl-44
Aryl-45 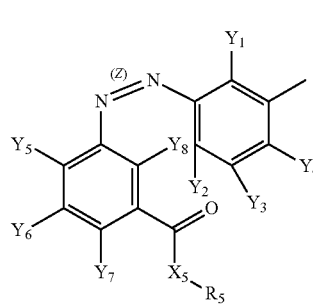
Aryl-46 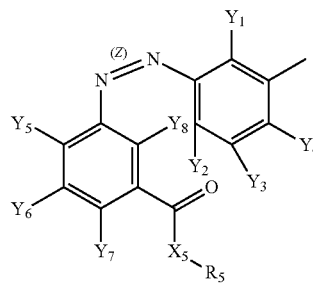

Aryl-47
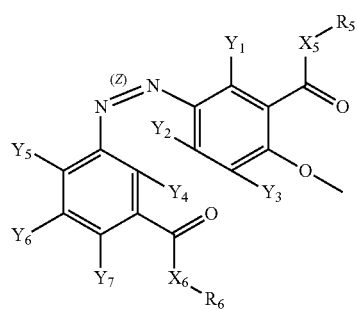
Aryl-48
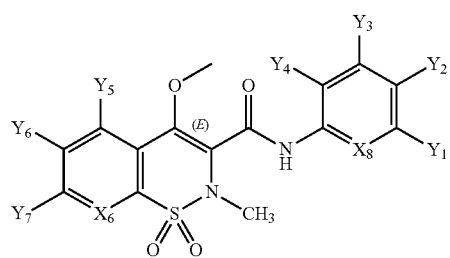
Aryl-49
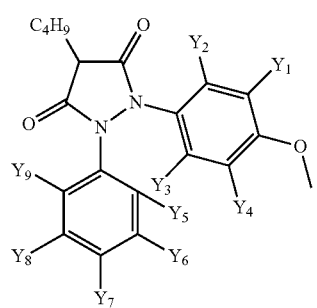
Aryl-50
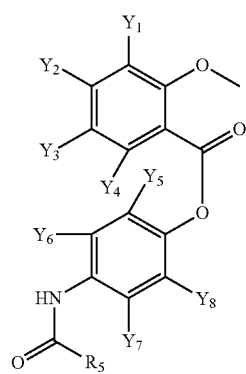
Aryl-51
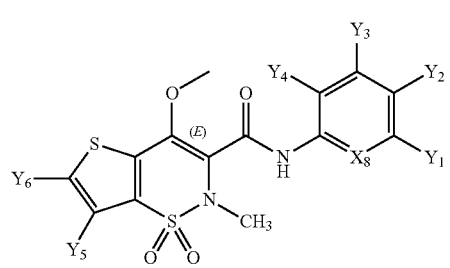
Aryl-52
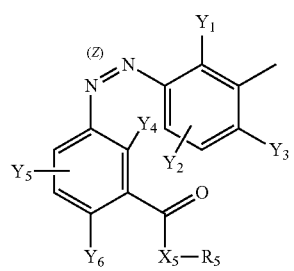
Aryl-53
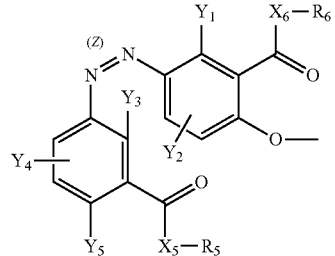
Aryl-54
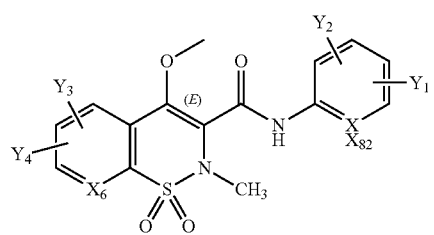
Aryl-55
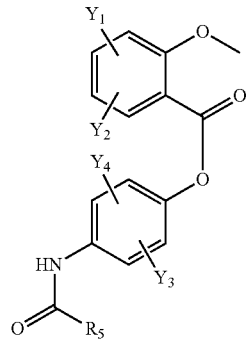
Aryl-56
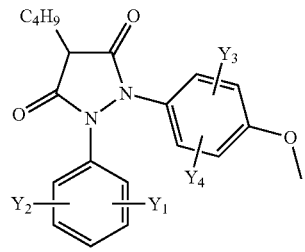
Aryl-57
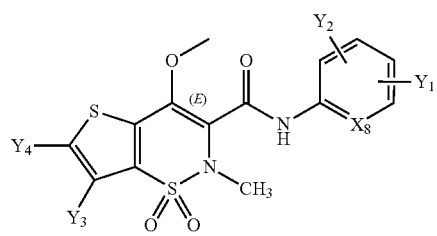

Aryl-58
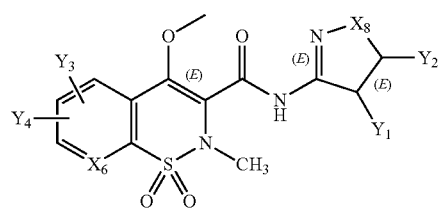
Aryl-59
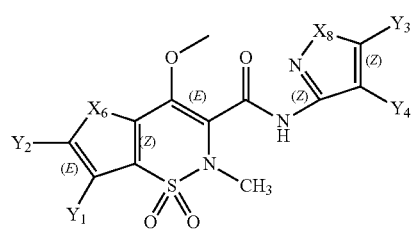
Aryl-60
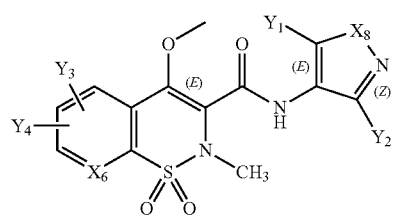
Aryl-61
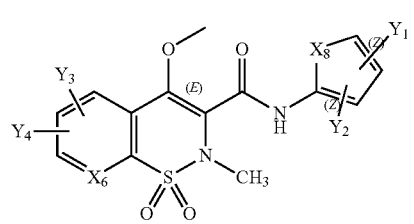
Aryl-62
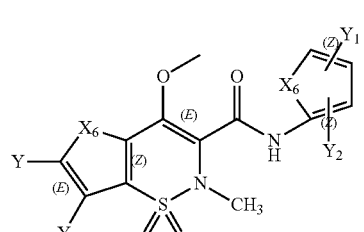
Aryl-63
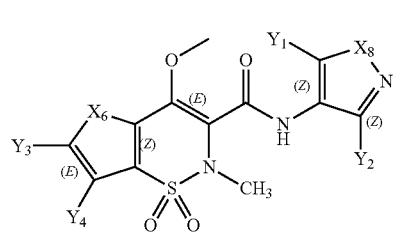
Aryl-64
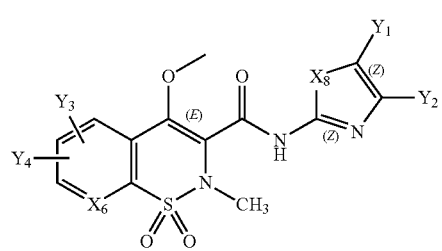
Aryl-65
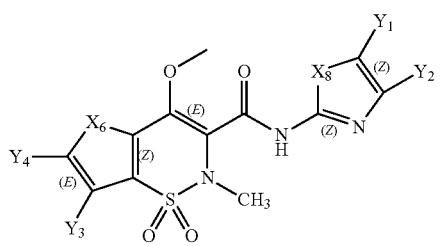
Aryl-66
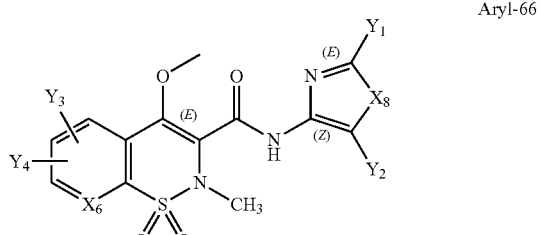
Aryl-67
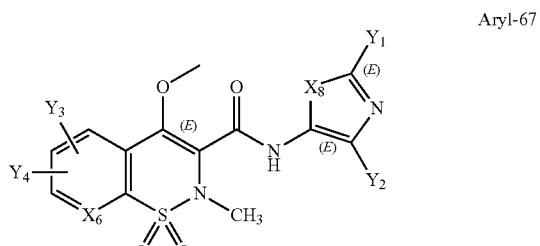
Aryl-68
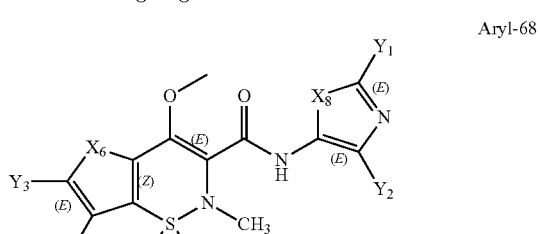
Aryl-69
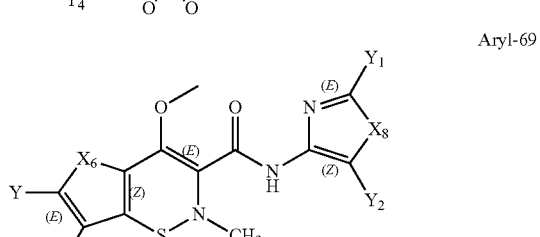
Aryl-70
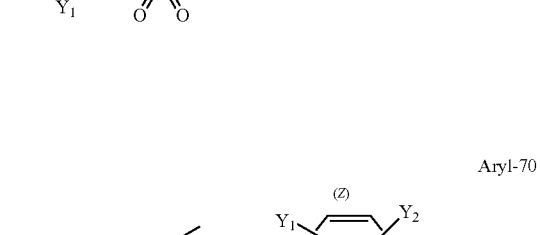
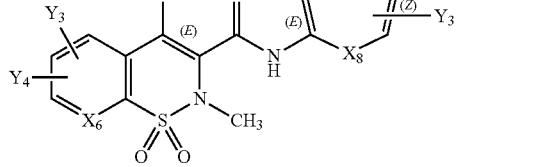

Aryl-71

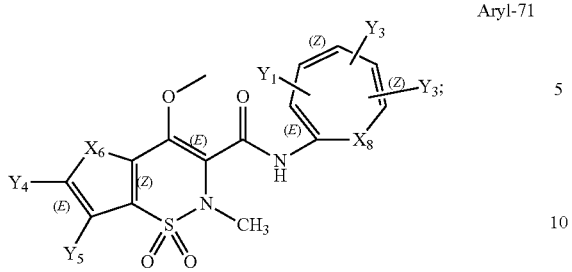

$F_{ab}$ is a functional unit of a HPP of an antimicrobial or antimicrobial-related compound, examples of $F_{ab}$ include, without limitation, Structure FP-1, Structure FP-2, Structure FP-3, Structure FP-4, Structure FP-5, Structure FP-6, Structure FP-7, Structure FP-8, Structure FP-9, Structure FP-10, Structure FP-11, Structure FP-12, Structure FP-13, Structure FP-14, Structure FP-15, Structure FP-16, Structure FP-17, Structure FP-18, Structure FP-19, Structure FP-20, Structure FP-21, Structure FP-22, Structure FP-23, Structure FP-24, Structure FP-25, Structure FP-26, Structure FP-27, Structure FP-28, Structure FP-29, Structure FP-30, Structure FP-31, Structure FP-32, Structure FP-33, Structure FP-34, Structure FP-35, Structure FP-36, Structure FP-37, Structure FP-38, Structure FP-39, Structure FP-40, Structure FP-41, Structure FP-42, Structure FP-43, Structure FP-44, Structure FP-45, Structure FP-46, Structure FP-47, Structure FP-48, Structure FP-49, Structure FP-50, Structure FP-51, Structure FP-52, Structure FP-53, Structure FP-54, Structure FP-55, Structure FP-56, Structure FP-57, Structure FP-58, Structure FP-59, Structure FP-60, Structure FP-61, Structure FP-62, Structure FP-63, Structure FP-64, Structure FP-65, Structure FP-66, Structure FP-67, Structure FP-68, Structure FP-69, Structure FP-70, Structure FP-71, Structure FP-72, Structure FP-73, Structure FP-74, Structure FP-75, Structure FP-76, Structure FP-77, Structure FP-78, Structure FP-79, Structure FP-80, Structure FP-81, Structure FP-82, Structure FP-83, Structure FP-84, Structure FP-85, Structure FP-86, Structure FP-87, Structure FP-88, Structure FI-1, Structure FI-2, Structure FI-3, Structure FI-4, Structure FI-5, Structure FI-6, Structure FI-7, Structure FI-8, Structure FI-9, Structure FI-10, Structure FI-11, Structure FI-12, Structure FI-13, Structure FI-14, Structure FI-15, Structure FI-16, Structure FI-17, Structure FI-18, Structure FI-19, Structure FI-20, Structure FI-21, Structure FI-22, Structure FI-23, Structure FI-24, Structure FI-25, Structure FI-26, Structure FI-27, Structure FI-28, Structure FI-29, Structure FI-30, Structure FI-31, Structure FI-32, Structure FI-33, Structure FS-1, Structure FS-2, Structure FS-3, Structure FS-4, Structure FS-5, Structure FS-6, Structure FS-7, Structure FS-8, Structure FS-9, Structure FS-10, Structure FS-11, Structure FS-12, Structure FS-13, Structure FS-14, Structure FS-15, Structure FS-16, Structure FS-17, Structure FS-18, Structure FS-19, Structure FS-20, Structure FT-1, Structure FT-2, Structure FT-3, Structure FT-4, Structure FT-5, Structure FT-6, Structure FT-7, Structure FT-8, Structure FT-9, Structure FT-10, Structure FT-11, Structure FT-12, Structure FT-13, Structure FT-14, Structure FT-15, Structure FT-16, Structure FT-17, Structure FT-18, Structure FT-19, and Structure FT-20:

Structure FP-1

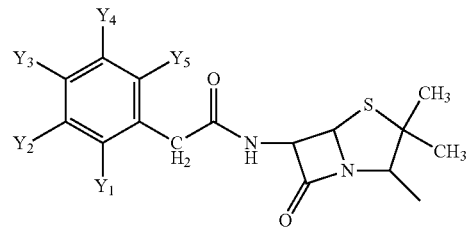

Structure FP-2

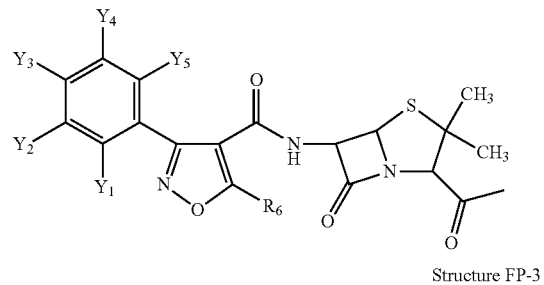

Structure FP-3

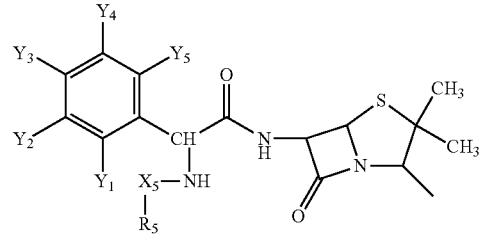

Structure FP-4

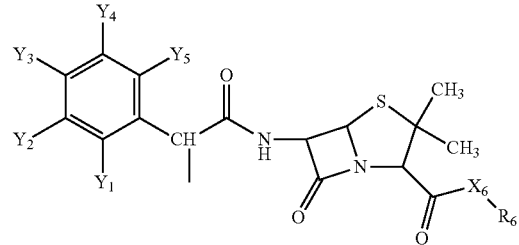

Structure FP-5

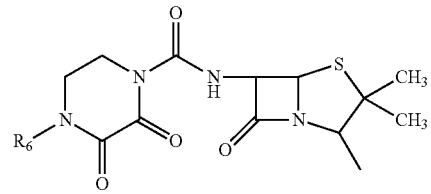

Structure FP-6
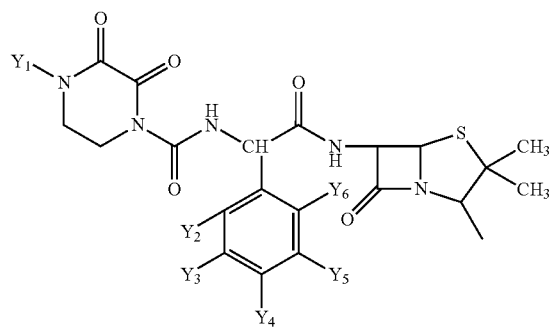
Structure FP-7
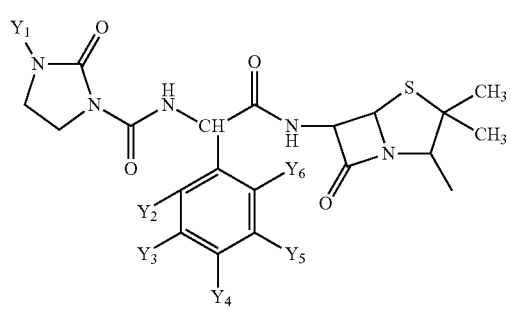
Structure FP-8
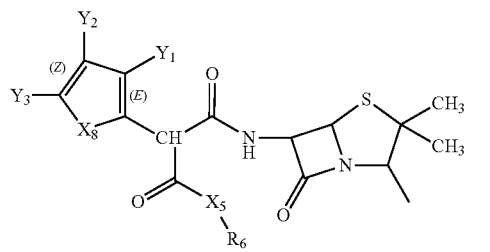
Structure FP-9
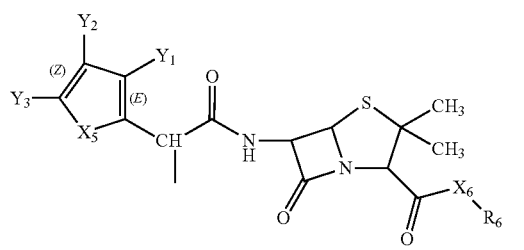
Structure FP-10
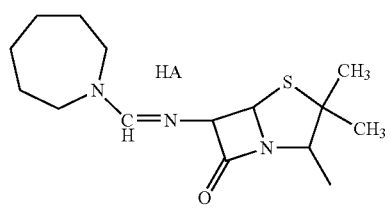
Structure FP-11
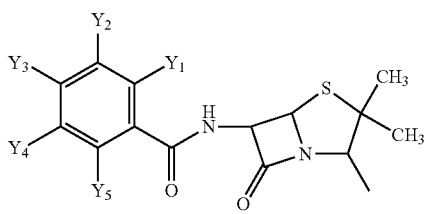
Structure FP-12
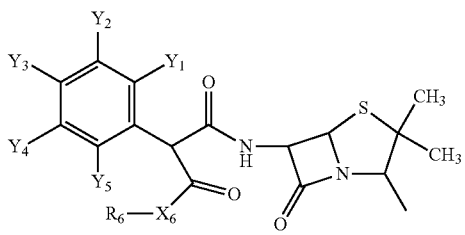
Structure FP-13
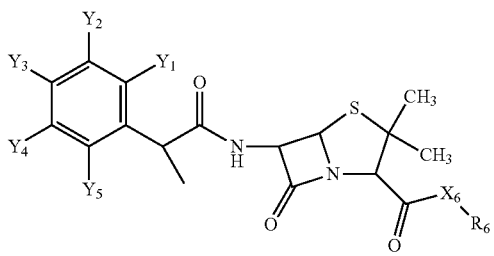
Structure FP-14
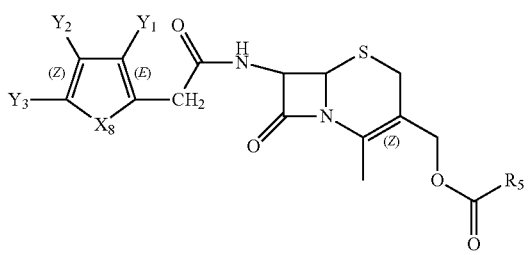
Structure FP-15
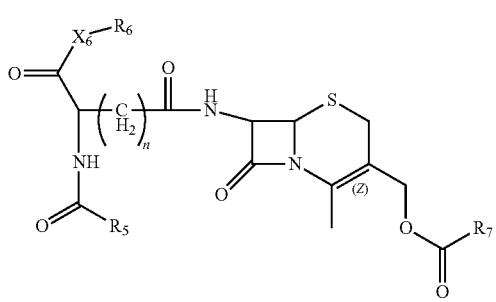

Structure FP-16
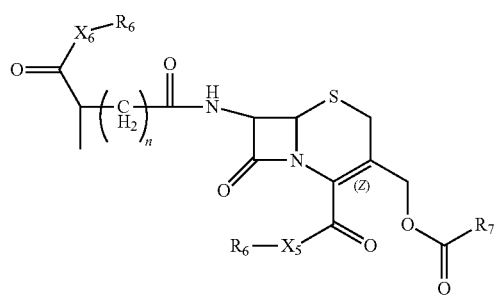
Structure FP-17
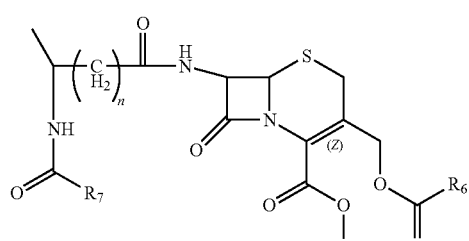
Structure FP-18
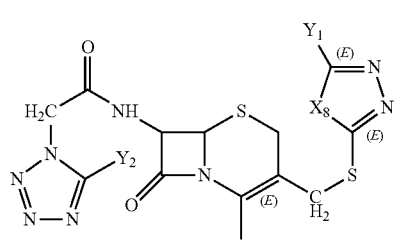
Structure FP-19
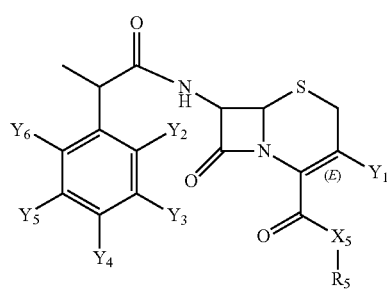
Structure FP-20
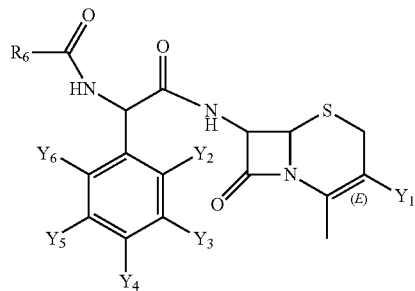
Structure FP-21
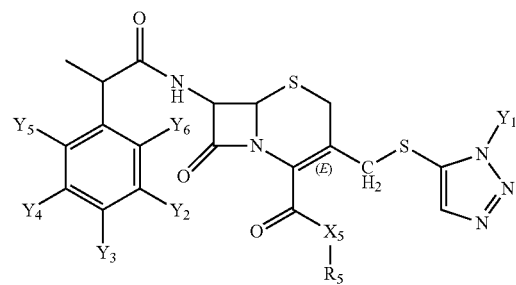
Structure FP-22
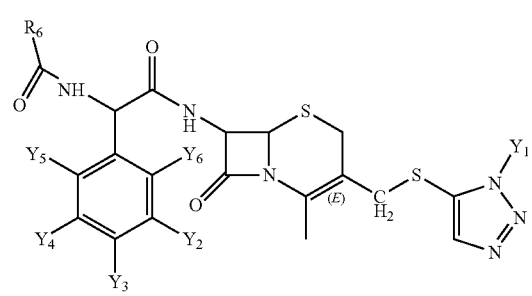
Structure FP-23
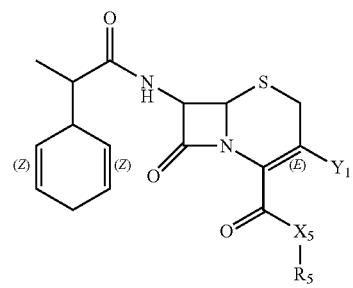
Structure FP-24
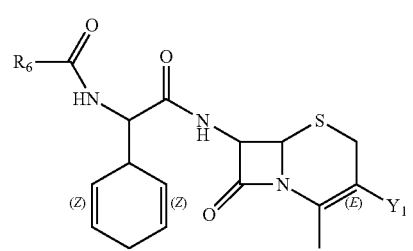
Structure FP-25
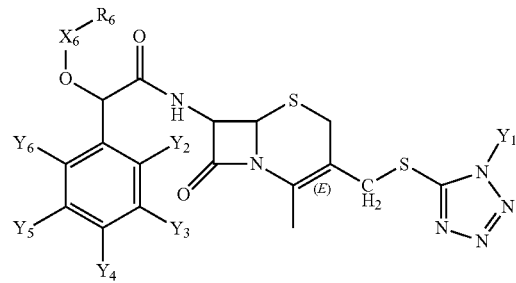

Structure FP-26
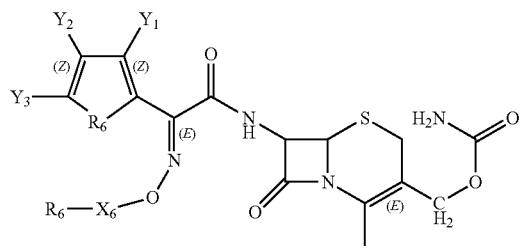
Structure FP-27
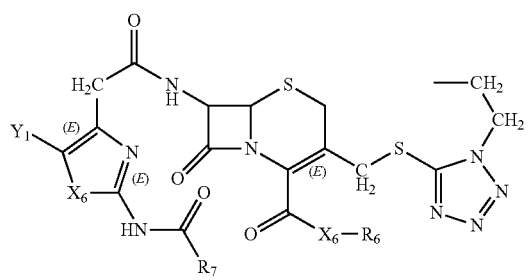
Structure FP-28
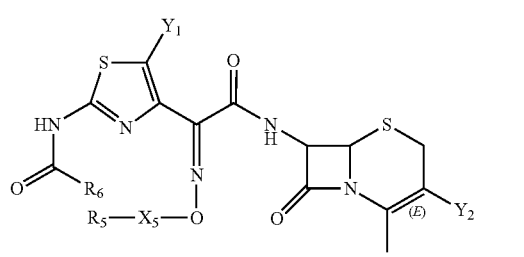
Structure FP-29
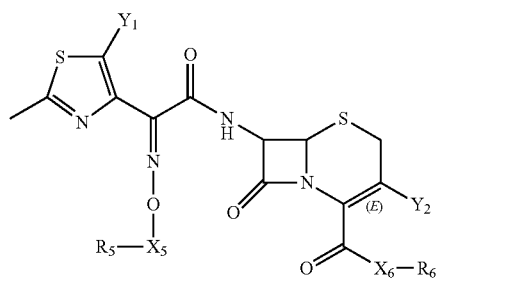
Structure FP-30
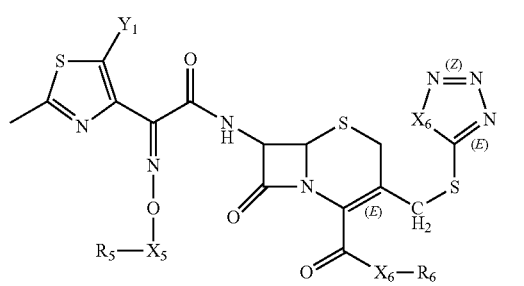
Structure FP-31
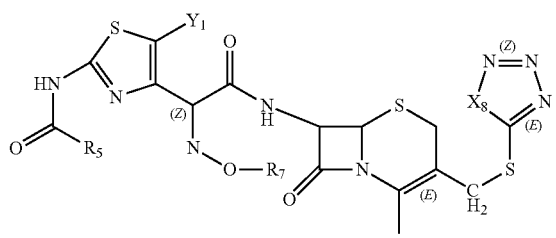
Structure FP-32
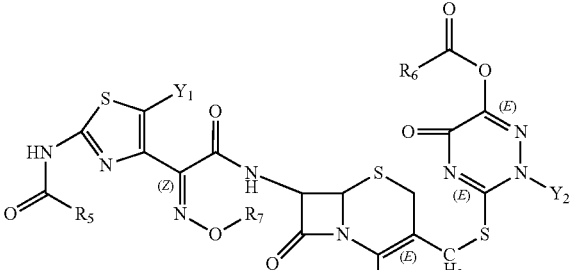
Structure FP-33
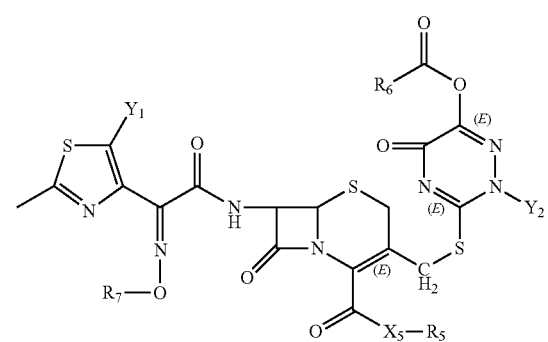
Structure FP-34
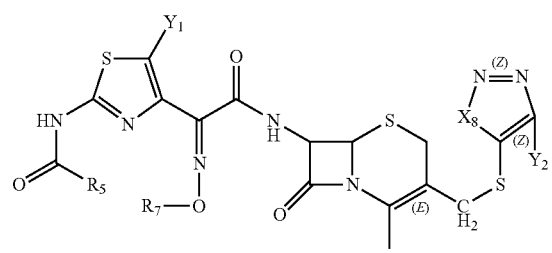
Structure FP-35

Structure FP-36
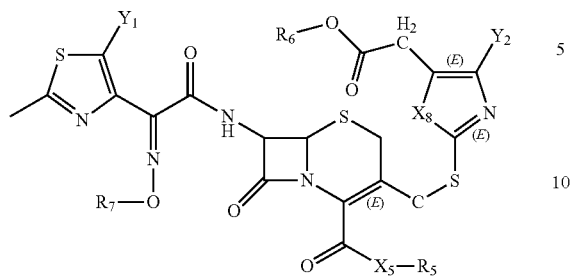
Structure FP-37
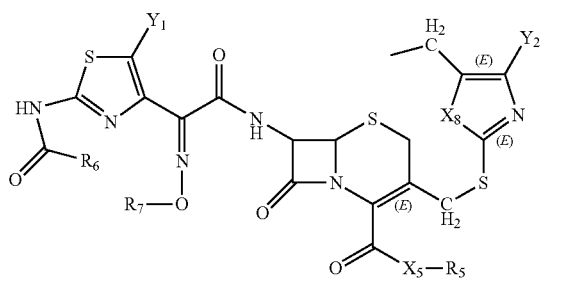
Structure FP-38
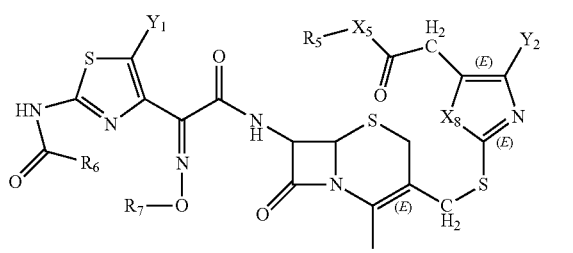
Structure FP-39
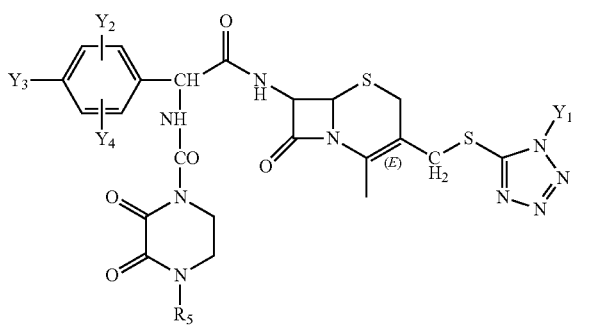
Structure FP-40
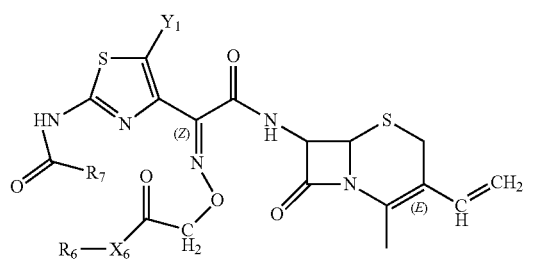
Structure FP-41
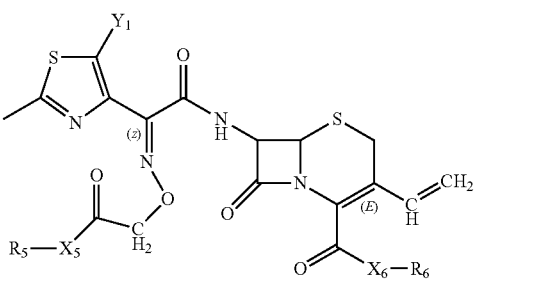
Structure FP-42
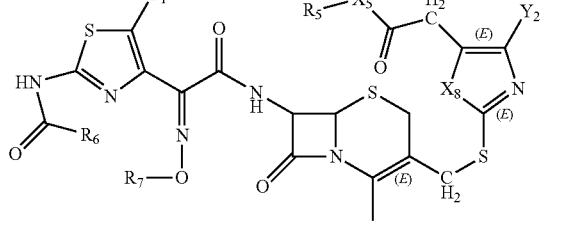
Structure FP-43
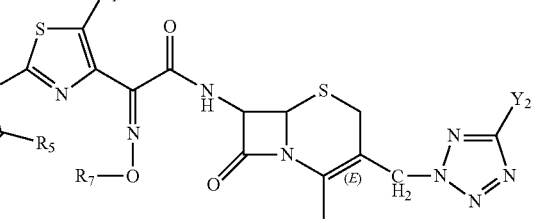
Structure FP-44
Structure FP-45
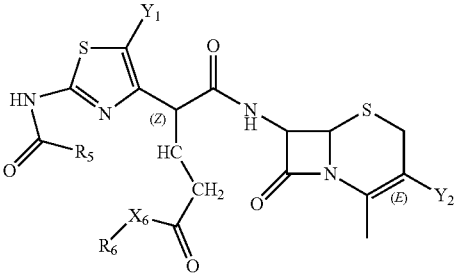

Structure FP-46
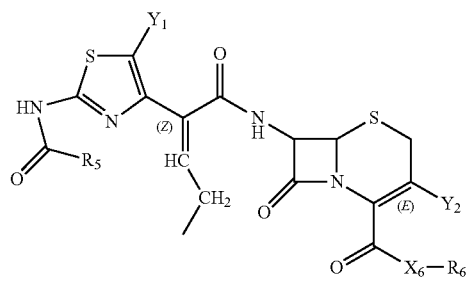
Structure FP-47
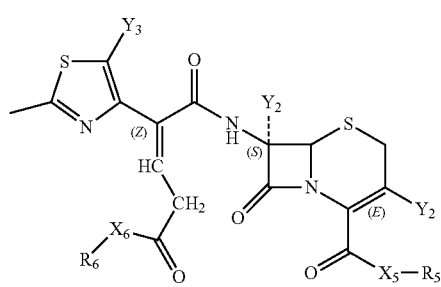
Structure FP-48
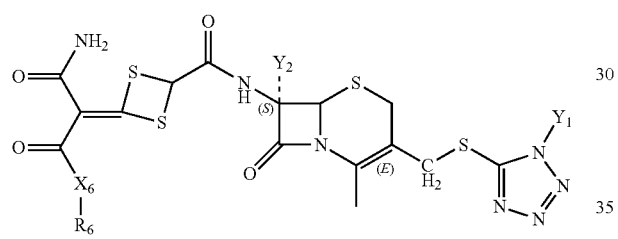
Structure FP-49
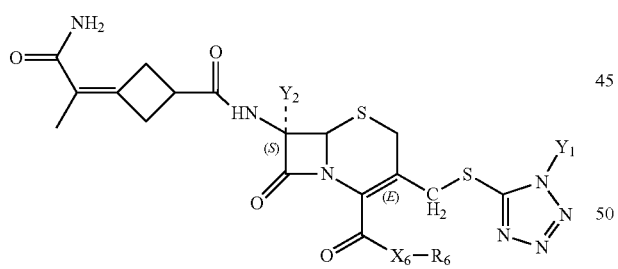
Structure FP-50
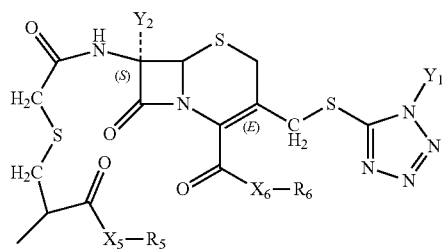
Structure FP-51
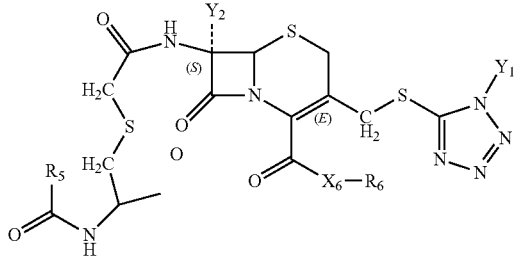
Structure FP-52
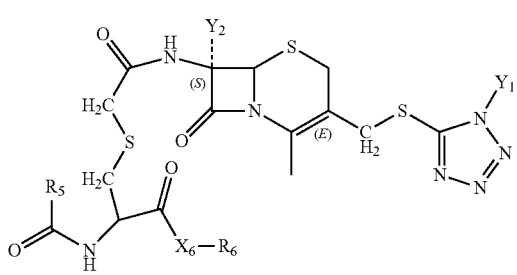
Structure FP-53
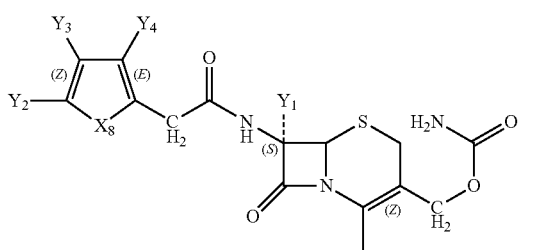
Structure FP-54
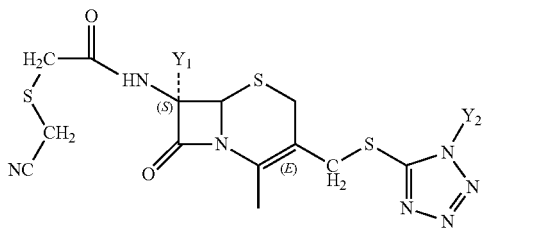
Structure FP-55
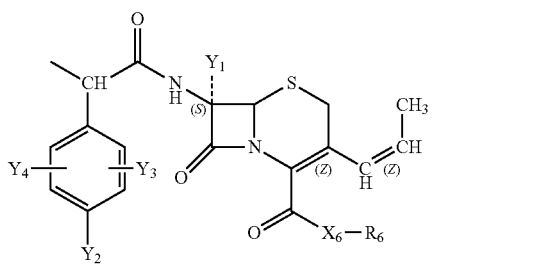
Structure FP-56
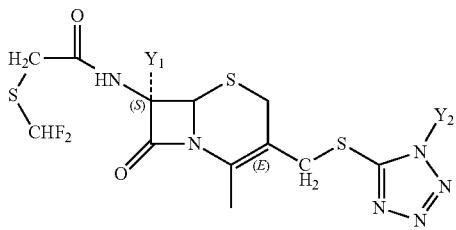

Structure FP-57
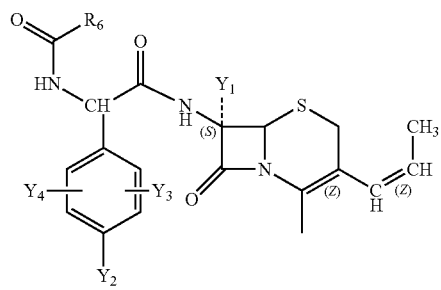
Structure FP-58
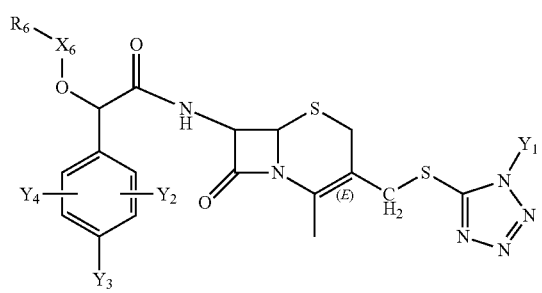
Structure FP-59
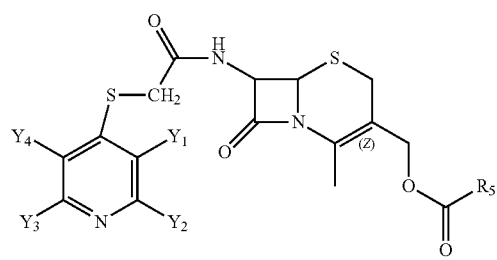
Structure FP-60
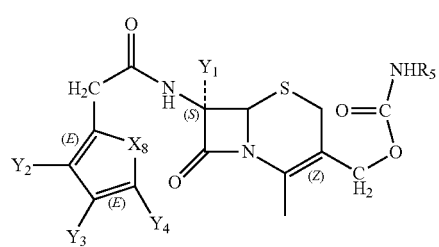
Structure FP-61
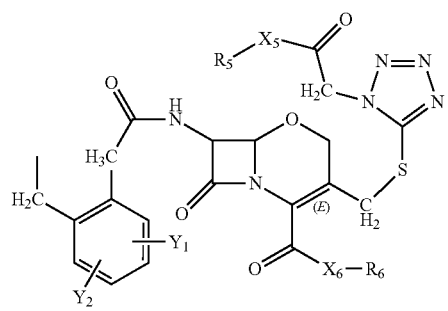
Structure FP-62
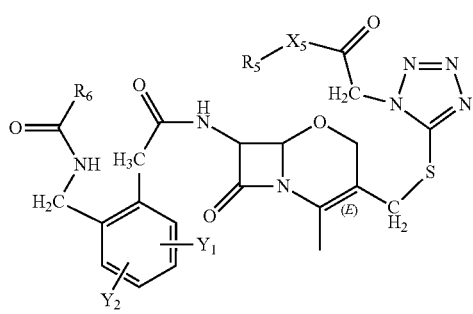
Structure FP-63
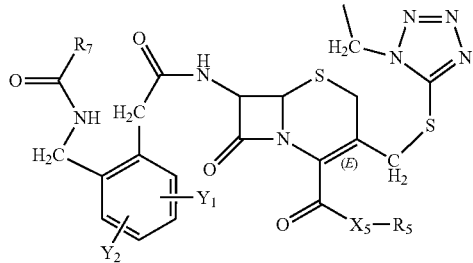
Structure FP-64
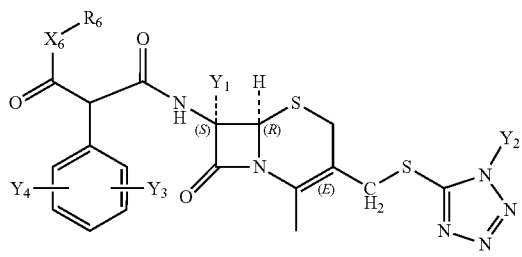
Structure FP-65
Structure FP-66

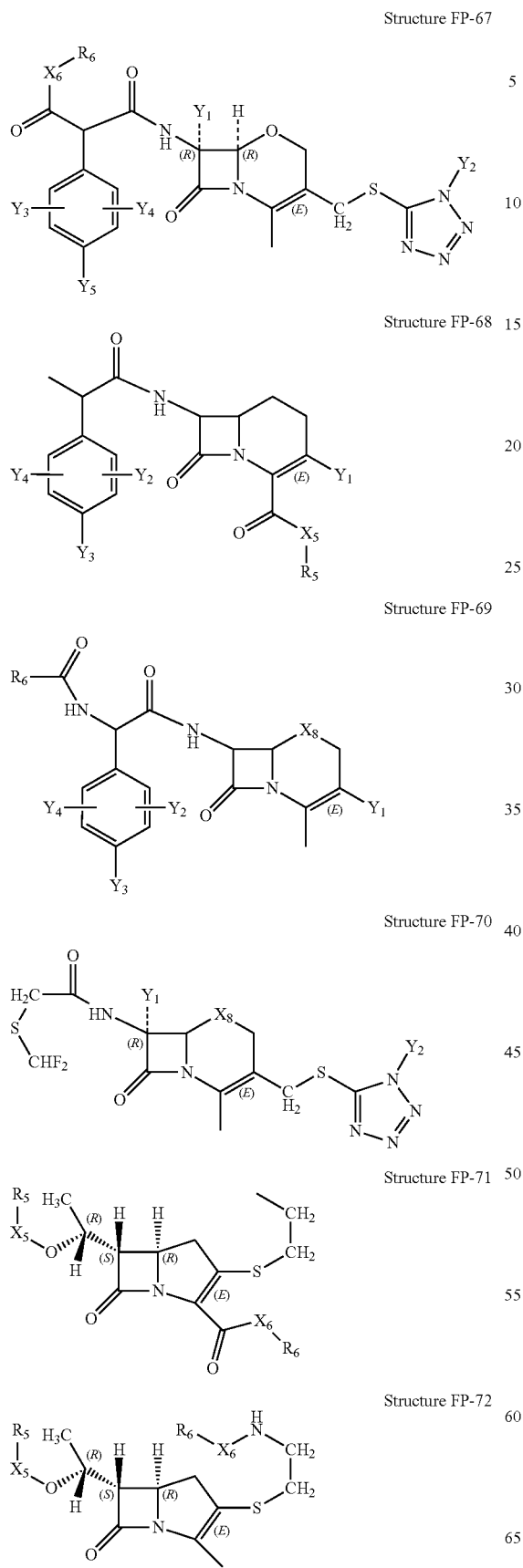
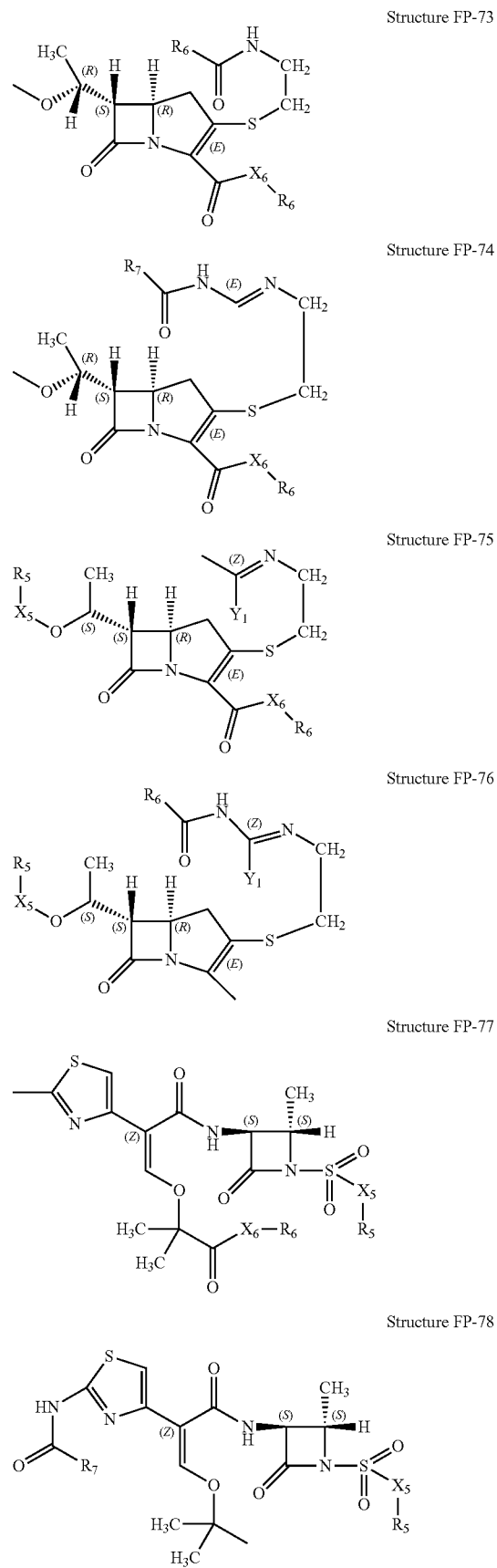

Structure FP-79
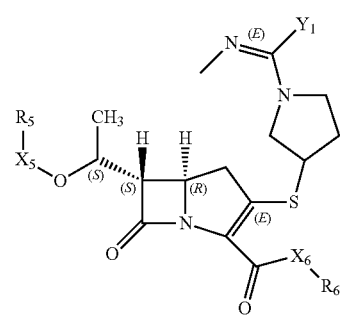
Structure FP-80
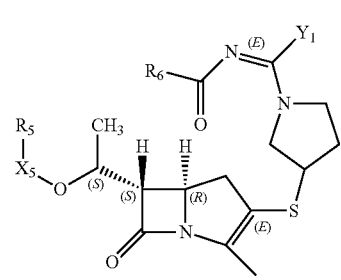
Structure FP-81
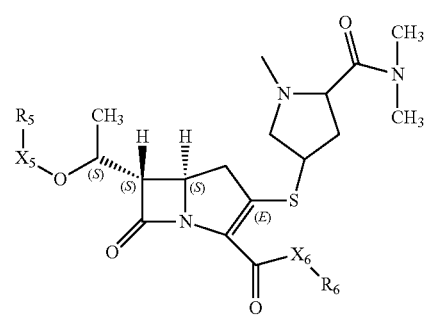
Structure FP-82
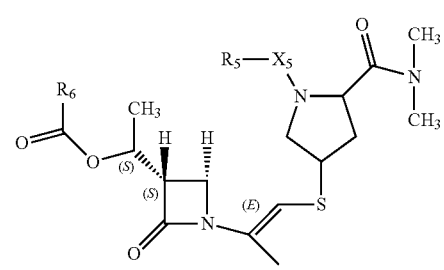
Structure FP-83
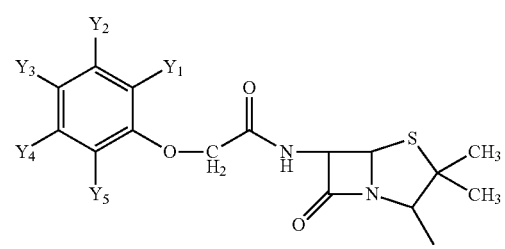
Structure FP-84
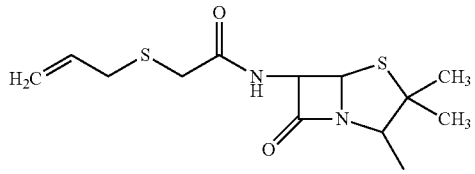
Structure FP-85
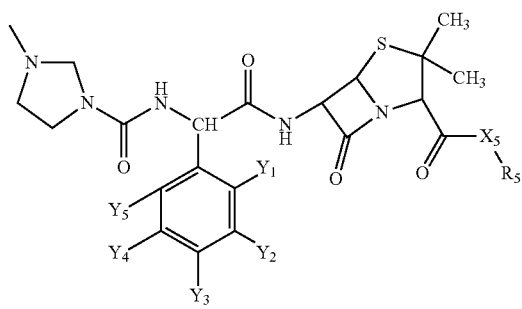
Structure FP-86
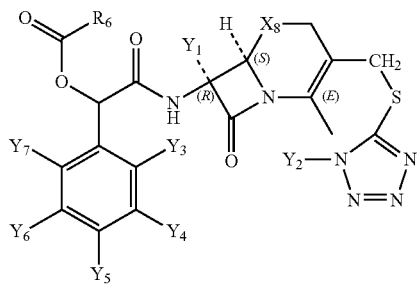
Structure FP-87
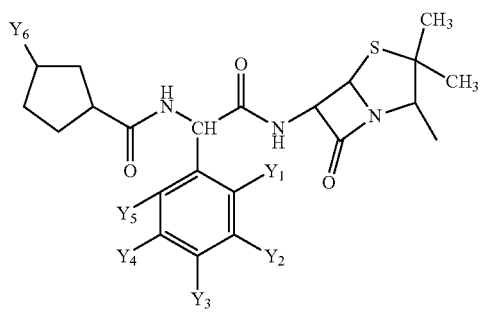
Structure FP-88
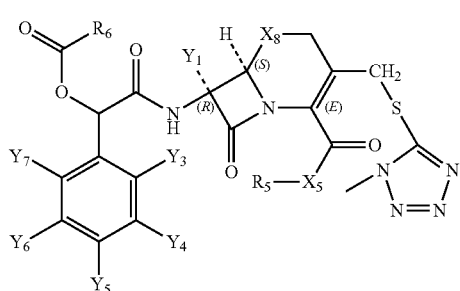
Structure FI-1
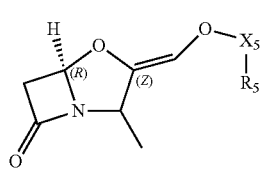

55
-continued
Structure FI-2
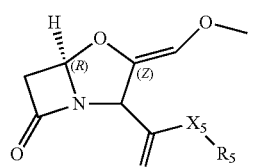
Structure FI-3
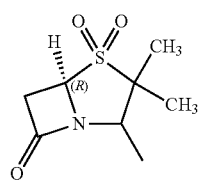
Structure FI-4
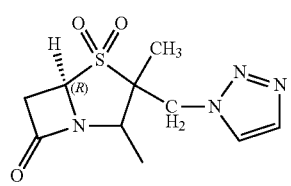
Structure FI-5
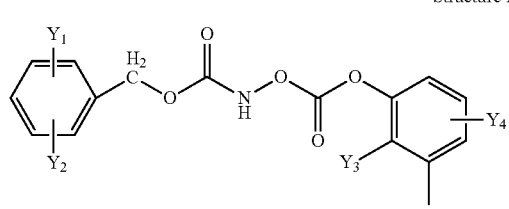
Structure FI-6
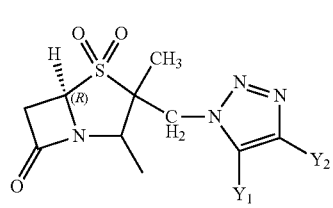
Structure FI-7
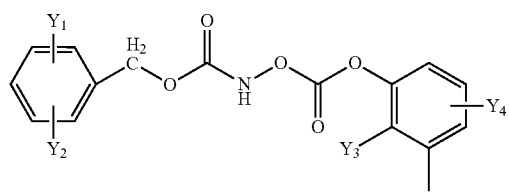
Structure FI-8
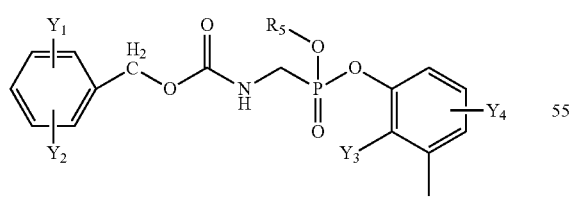
Structure FI-9
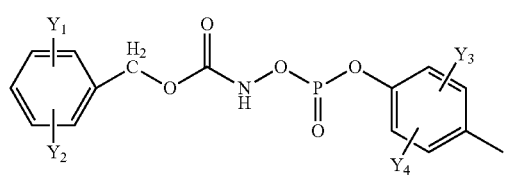
56
-continued
Structure FI-10
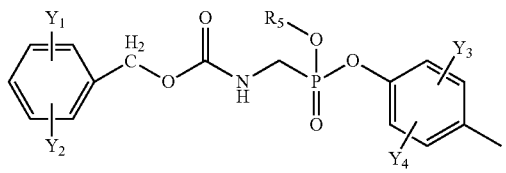
Structure FI-11
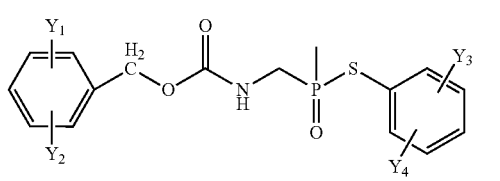
Structure FI-12
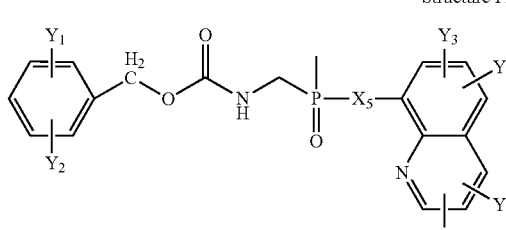
Structure FI-13
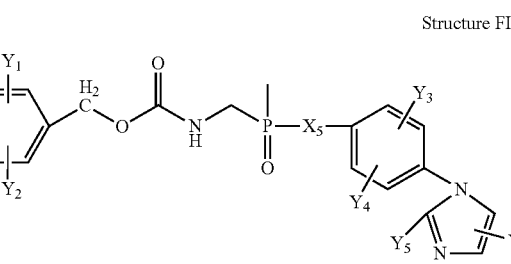
Structure FI-14
Structure FI-14
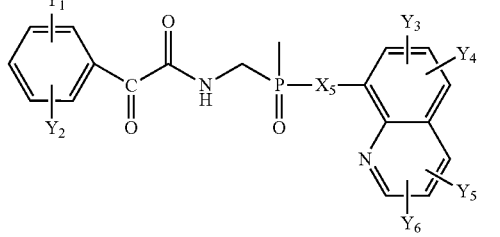
Structure FI-15
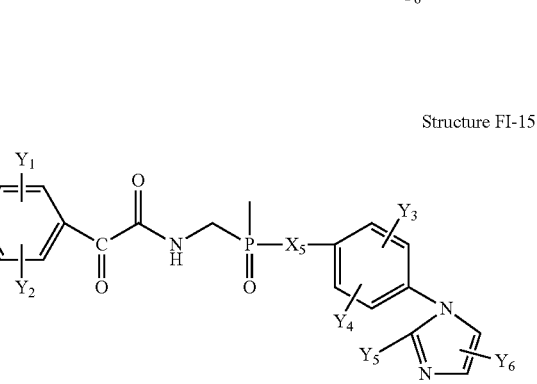

Structure FI-16
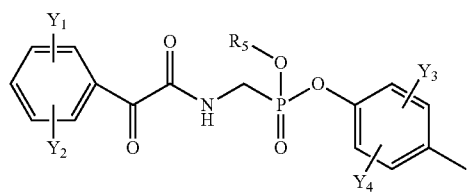
Structure FI-17
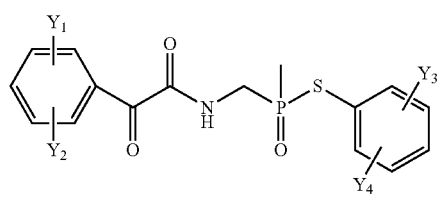
Structure FI-18
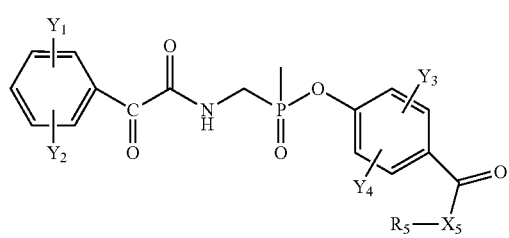
Structure FI-19
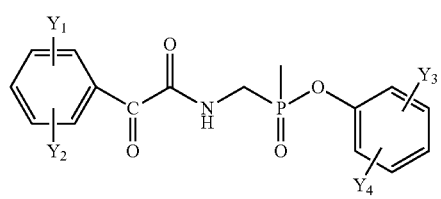
Structure FI-20
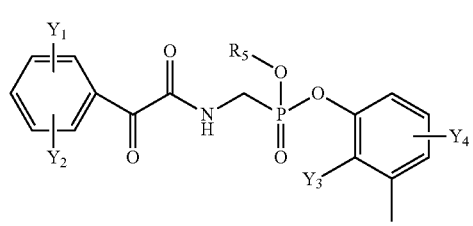
Structure FI-21
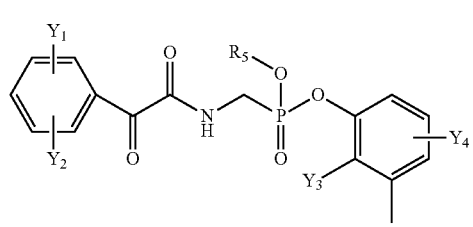
Structure FI-22
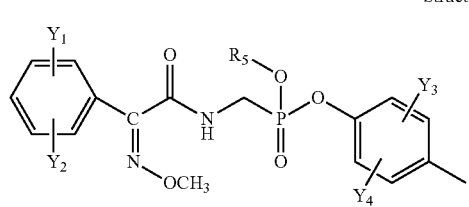
Structure FI-23
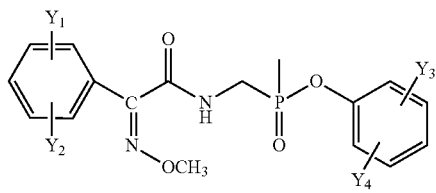
Structure FI-24
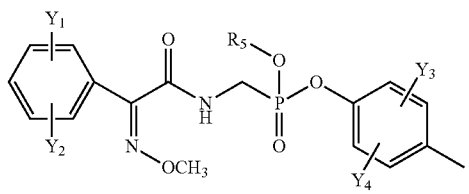
Structure FI-25
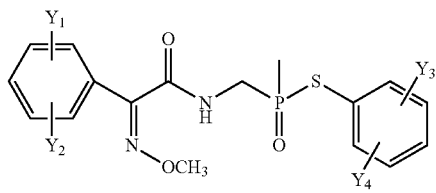
Structure FI-26
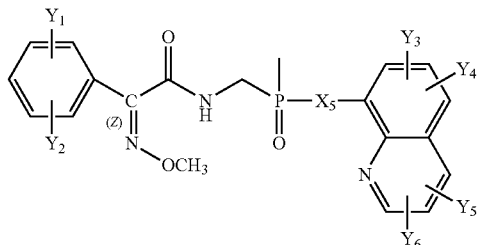
Structure FI-27
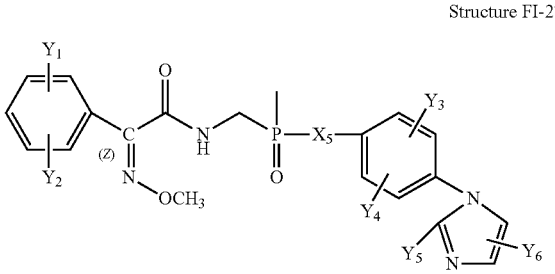
Structure FI-28
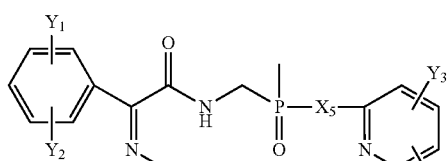
Structure FI-29
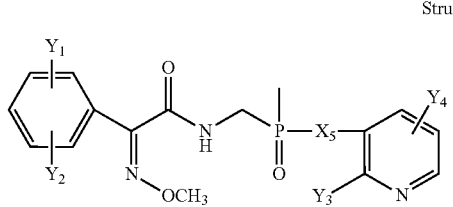

Structure FI-30
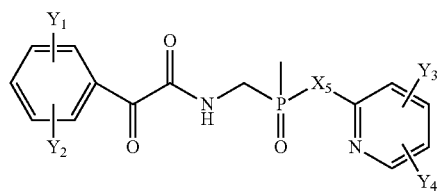
Structure FI-31
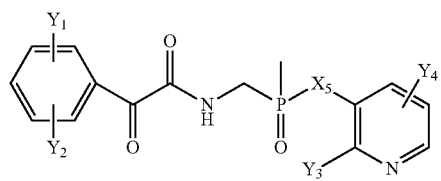
Structure FI-32
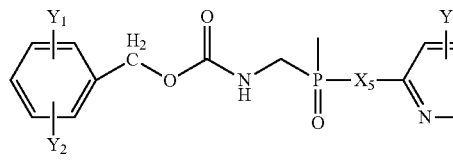
Structure FI-33
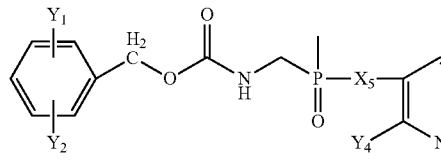
Structure FS-1
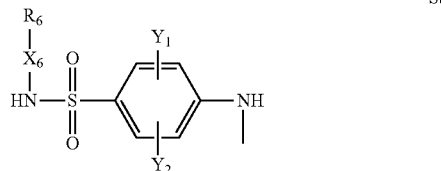
Structure FS-2
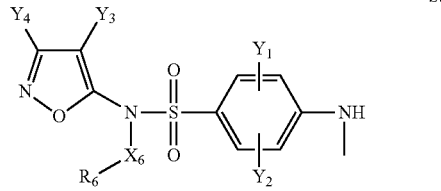
Structure FS-3
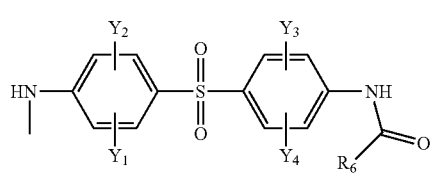
Structure FS-4
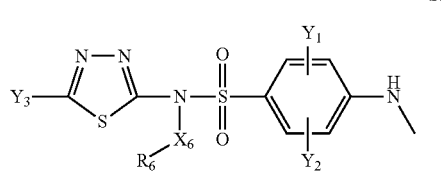
Structure FS-5
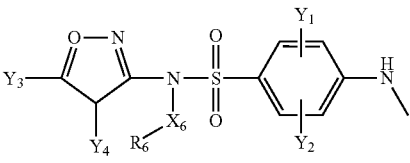
Structure FS-6
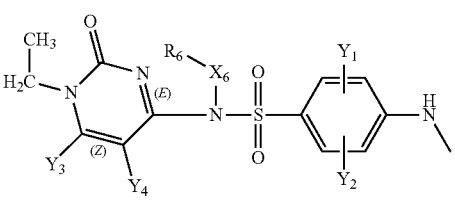
Structure FS-7
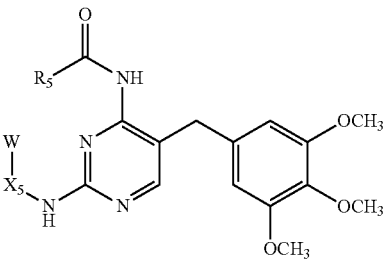
Structure FS-8
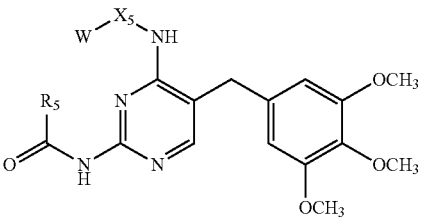
Structure FS-9
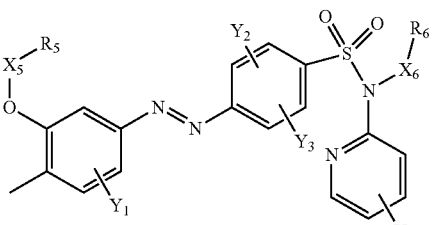
Structure FS-10
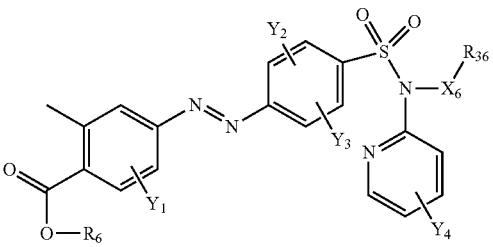

Structure FS-11
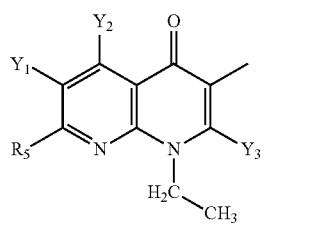
Structure FS-12
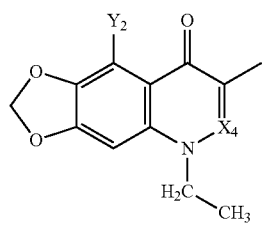
Structure FS-13
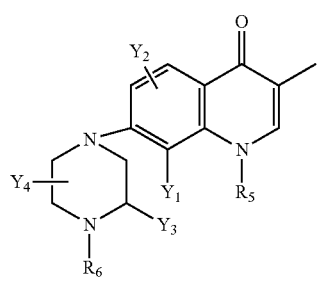
Structure FS-14
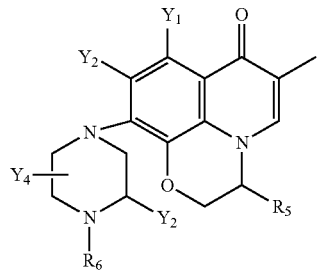
Structure FS-15
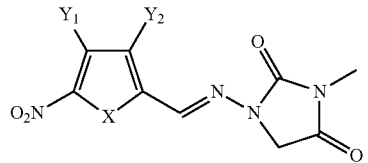
Structure FS-16
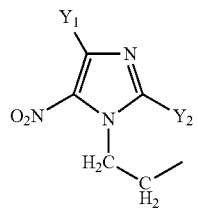
Structure FS-17
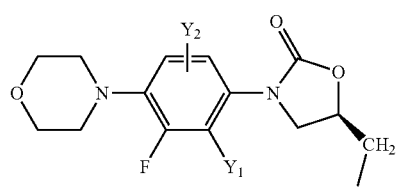
Structure FS-18
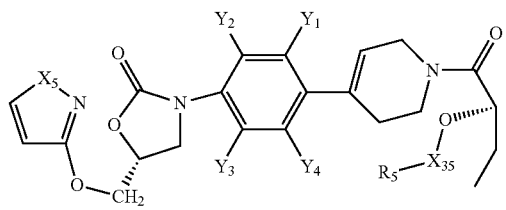
Structure FS-19
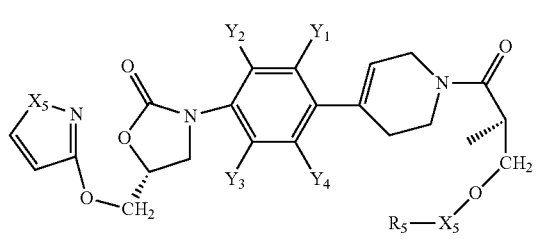
Structure FS-20
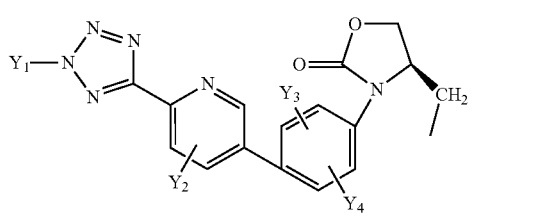
Structure FT-1
Structure FT-2
Structure FT-3
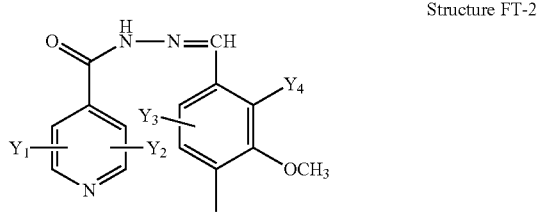
Structure FT-4
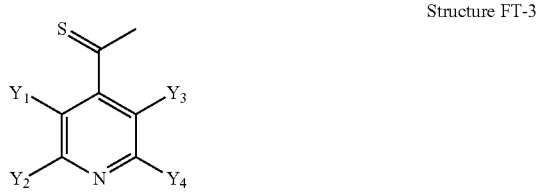
Structure FT-5
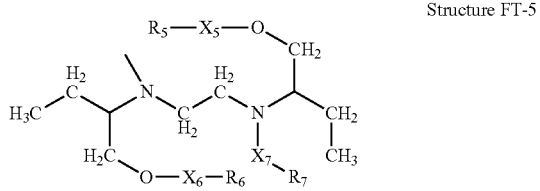

-continued
Structure FT-6
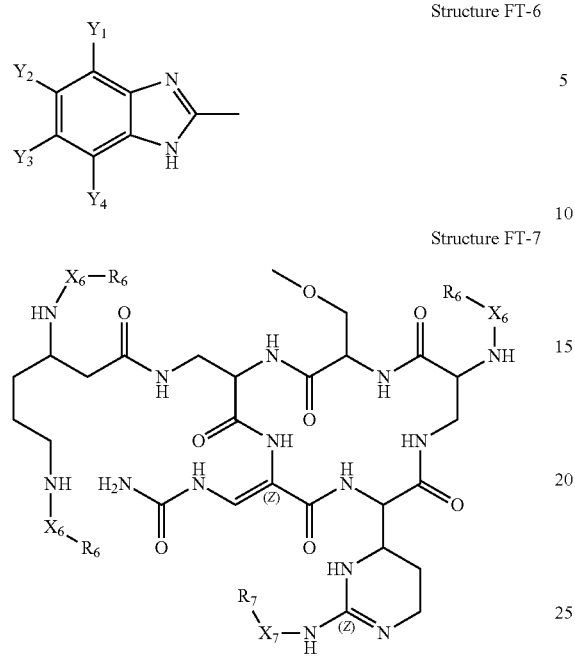
Structure FT-7
Structure FT-8
Structure FT-9
-continued
Structure FT-10
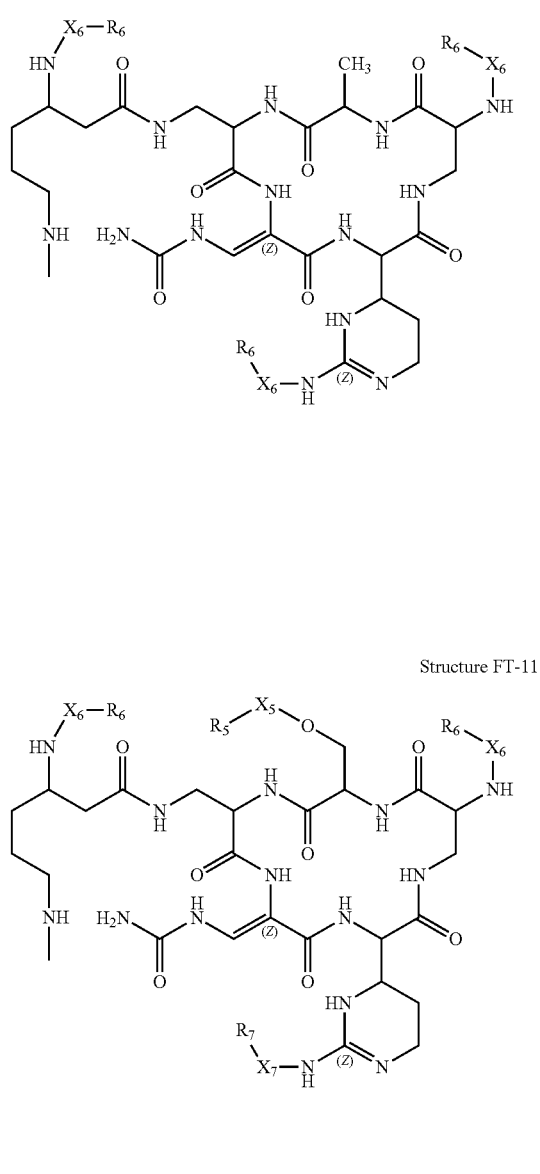
Structure FT-11
Structure FT-12

Structure FT-13

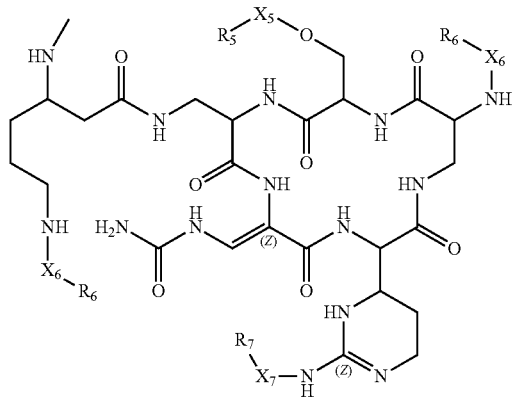

Structure FT-17

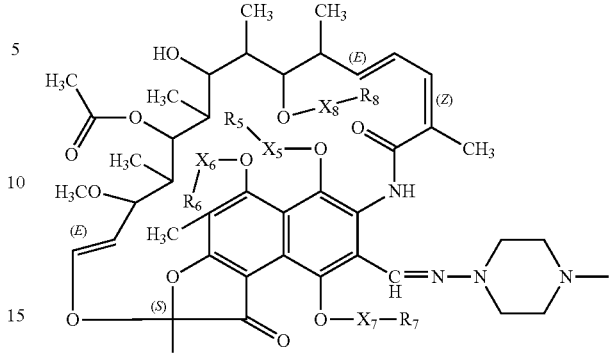

Structure FT-14

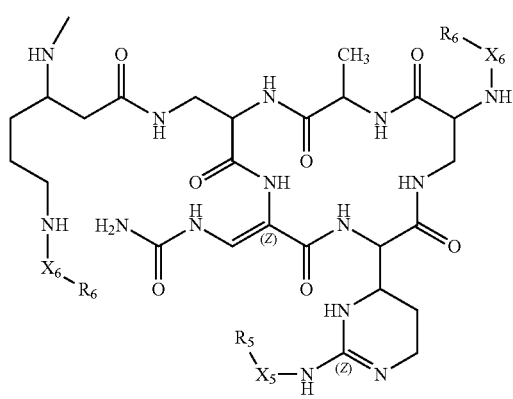

Structure FT-18

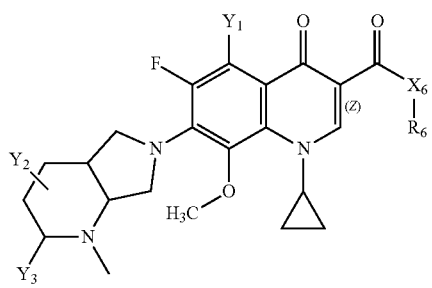

Structure FT-19

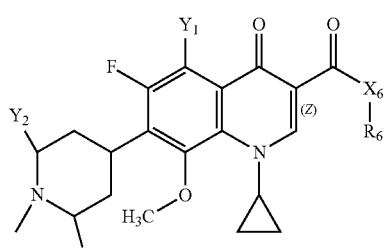

Structure FT-15

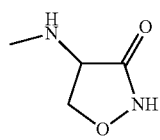

Structure FT-20

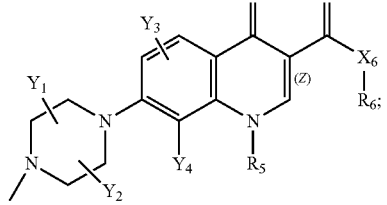

Structure FT-16

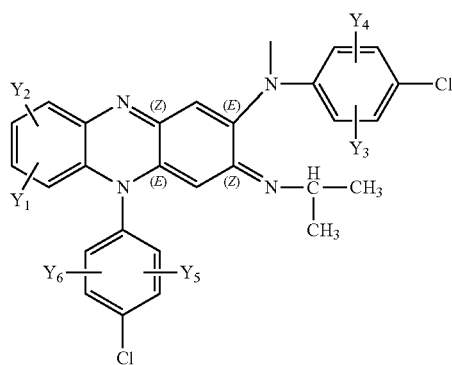

HA, W, T, $L_1$, $L_2$, $L_4$, $R_5$, $R_6$, $X_5$, and $X_7$ being defined the same as supra;

$L_1$ being selected from the group consisting of nothing, O, S, —N($L_3$)-, —N($L_3$)-$CH_2$—O, —N($L_3$)-$CH_2$—N($L_5$)-, —O—$CH_2$—O—, —O—CH($L_3$)-O, and —S—CH($L_3$)-O—;

$L_2$ being selected from the group consisting of nothing, O, S, —N($L_3$)-, —N($L_3$)-$CH_2$—O, —N($L_3$)-$CH_2$—N($L_5$)-, —O—$CH_2$—O—, —O—CH($L_3$)-O, —S—CH($L_3$)-O—, —O-$L_3$-, —N-$L_3$-, —S-$L_3$-, —N($L_3$)-$L_5$- and $L_3$;

L₄ being selected from the group consisting of C=O, C=S,

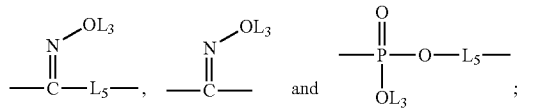

for each L₁, L₂, and L₄, L₃ and L₅ being independently selected from the group consisting of nothing, H, CH₂C(=O)OL₆, substituted and unsubstituted alkyl, substituted and unsubstituted cycloalkyl, substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, P, NL₃, or any other pharmaceutically acceptable groups;

L₆ being independently selected from the group consisting of H, OH, Cl, F, Br, I, substituted and unsubstituted alkyl, substituted and unsubstituted cycloalkyl, and substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, N, P(O)OL₆, CH=CH, C≡C, CHL₆, CL₆L₇, aryl, heteroaryl, or cyclic groups;

L₇ being independently selected from the group consisting of H, OH, Cl, F, Br, I, substituted and unsubstituted alkyl, substituted and unsubstituted cycloalkyl, and substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, N, P(O)OL₆, CH=CH, C≡C, CHL₆, CL₆L₇, aryl, heteroaryl, or cyclic groups; and any CH₂ groups may be replaced with O, S, or NH.

X₆ and X₈ being independently selected from the group consisting of nothing, C(=O), C(=S), OC(=O), OC(=S), CH₂, CH, S, O and NR₅;

Y₁, Y₂, Y₃, Y₄, Y₅, Y₆, Y₇, Y₈, and Y₉ being independently selected from the group consisting of H, OH, OW, OC(=O)W, OC(=O)CH₃, CH₃, C₂H₅, C₃H₇, C₄H₉, R₆, SO₃R₆, CH₂OR₆, CH₂OC(=O)R₆, CH₂C(=O)OR₈, OCH₃, OC₂H₅, OR₆, CH₃SO₂, R₆SO₂, CH₃SO₃, R₆SO₃, NO₂, CN, CF₃, OCF₃, CH₂(CH₂)ₙNR₅R₆, CH₂(CH₂)ₙOR₆, CH(C(=O)NH₂)NHR₆, CH₂C(=O)NH₂, F, Br, I, Cl, CH=CHC(=O)NHCH₂C(=O)OW, CH=CHC(=O)NHCH₂L₁-L₄-L₂-W, NR₈C(=O)R₅, SO₂NR₅R₈, C(=O)R₅, SR₅, R₆OOCCH(NHR₇)(CH₂)ₙC(=O)NH—, R₆OOCCH(NHR₇)(CH₂)ₙSC(=O)NH—, CF₃SCH₂C(=O)NH—, CF₃CH₂C(=O)NH—, CHF₂SCH₂C(=O)NH—, CH₂FSCH₂C(=O)NH—, NH₂C(=O)CHFS—CH₂C(=O)NH—, R₇NHCH(C(=O)OW)CH₂SCH₂C(=O)NH—, R₇NHCH(L₁-L₄-L₂-W)CH₂SCH₂C(=O)NH—, CNCH₂SCH₂C(=O)NH—, CH₃(CH₂)ₙC(=O)NH—, R₇N=CHNR₇CH₂CH₂S—, R₇N=C(NHR₇)NHC(=O)—, R₇N=C(NHR₇)NHC(=O)CH₂, CH₃C(Cl)=CHCH₂SCH₂C(=O)NH—, (CH₃)₂C(OR₆)—, CNCH₂C(=O)NH—, CNCH₂CH₂S—, R₇HN=CH(NR₇)CH₂CH₂S—, CH₂=CHCH₂SCH₂C(=O)NH—, CH₃CH(OH)—, CH₃CH(OR₈)—, CH₃CH(Y₁)—, (CH₃)₂CH—, CH₃CH₂—, CH₃(CH₂)ₙCH=CH(CH₂)ₘC(=O)NH—, substituted and unsubstituted perfluoroalkyl, substituted and unsubstituted alkoxyl, substituted and unsubstituted alkylthio, substituted and unsubstituted alkylamino, substituted and unsubstituted perfluoroalkyl, substituted and unsubstituted alkyl halide and substituted and unsubstituted alkylcarbonyl;

R₇ being independently selected from the group consisting of H, F, Cl, Br, I, CH₃NHC(=O)CH₂CH(NHR₈)C(=O), R₅N=C(NHR₆)NHC(=O)—, C(=O)CH₃, C(=O)R₆, PO(OR₅)OR₆, substituted and unsubstituted alkyl, substituted and unsubstituted cycloalkyl, substituted and unsubstituted heterocycloalkyl, substituted and unsubstituted alkyloxyl, substituted and unsubstituted alkenyl, substituted and unsubstituted alkynyl, substituted and unsubstituted aryl, substituted and unsubstituted heteroaryl, substituted and unsubstituted alkylcarbonyl, substituted and unsubstituted alkylamino, L₁-L₄-L₂-W, and C—(=O)—W;

R₈ being independently selected from the group consisting of H, F, Cl, Br, I, CH₃, C₂H₅, CF₃, CH₂CH₂F, CH₂CH₂Cl, CH₂CH₂Br, CH₂CH₂I, CH₂CHF₂, CH₂CF₃, CH₂F, CH₂Cl, CH₂Br, CH₂I, CH₂NR₆R₇, CH(NHR₇)CH₂C(=O)NH₂, C₃H₇, C₄H₉, C₅H₁₁, R₆, C(=O)R₆, C(=O)NH₂, CH₂C(=O)NH₂, CH₂OC(=O)NH₂, PO(OR₅)OR₆, C(CH₃)₂C(=O)OR₆, CH(CH₃)C(=O)OR₆, CH₂C(=O)OR₆, C(=O)—W, L₁-L₄-L₂-W, W, substituted and unsubstituted perfluoroalkyl, substituted and unsubstituted alkyl, substituted and unsubstituted cycloalkyl, substituted and unsubstituted heterocycloalkyl, substituted and unsubstituted alkoxyl, substituted and unsubstituted alkylamino, substituted and unsubstituted perfluoroalkyl, substituted and unsubstituted alkyl halide and substituted and unsubstituted alkylcarbonyl.

As used herein, the term "pharmaceutically acceptable salt" means those salts of compounds of the invention that are safe for application in a subject. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,11-methylene-bis-(2-hydroxy-3-naphthoate)) salts. Certain compounds of the invention can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts see BERGE ET AL., 66 J. PHARM. SCI. 1-19 (1977), incorporated herein by reference.

As used herein, unless specified otherwise, the term "alkyl" means a branched or unbranched, saturated or unsaturated, monovalent or multivalent hydrocarbon group, including saturated alkyl groups, alkenyl groups and alkynyl groups. Examples of alkyl include, but are not limited to, methyl, ethyl, propyl, isopropyl, butyl, isobutyl, t-butyl, pentyl, hexyl, heptyl, octyl, nonyl, decyl, undecyl, dodecyl, ethenyl, propenyl, butenyl, isobutenyl, pentenyl, hexenyl, heptenyl, octenyl, nonenyl, decenyl, undecenyl, dodecenyl, ethynyl, propynyl, butynyl, isobutynyl, pentynyl, hexynyl, heptynyl, octynyl, nonynyl, decynyl, undecynyl, dodecynyl, methylene, ethylene, propylene, isopropylene, butylene, isobutylene, t-butylene, pentylene, hexylene, heptylene, octylene, nonylene, decylene, undecylene and dodecylene. In certain embodiments, the hydrocarbon group contains 1 to 30 carbons. In certain embodiments, the hydrocarbon group contains 1 to 20 carbons. In certain embodiments, the hydrocarbon group contains 1 to 12 carbons.

As used herein, unless specified otherwise, the term "cycloalkyl" means an alkyl which contains at least one ring and no aromatic rings. Examples of cycloalkyl include, but are not limited to, cyclopropyl, cyclobutyl, cyclopentyl, cyclohexyl, cycloheptyl, cyclooctyl, cyclononyl, cyclodecyl, cycloundecyl and cyclododecyl. In certain embodiments, the hydrocarbon chain contains 1 to 30 carbons. In certain embodiments, the hydrocarbon group contains 1 to 20 carbons. In certain embodiments, the hydrocarbon group contains 1 to 12 carbons.

As used herein, unless specified otherwise, the term "heterocycloalkyl" means a cycloalkyl wherein at least one ring atom is a non-carbon atom. Examples of the non-carbon ring atom include, but are not limited to, S, O and N.

As used herein, unless specified otherwise, the term "alkoxyl" means an alkyl, cycloalkyl or heterocycloalkyl, which contains one or more oxygen atoms. Examples of alkoxyl include, but are not limited to, $-CH_2-OH$, $-OCH_3$, $-O-R_e$, $-R_e-OH$, $-R_{e1}-O-R_{e2}-$, wherein $R_e$, $R_{e1}$ and $R_{e2}$ can be the same or different alkyl, cycloalkyl or heterocycloalkyl.

As used herein, unless specified otherwise, the term "alkyl halide" means an alkyl, cycloalkyl or heterocycloalkyl, which contains one or more halogen atoms, wherein the halogen atoms can be the same or different. The term "halogen" means fluorine, chlorine, bromine or iodine. Examples of alkyl halide include, but are not limited to, $-R_e-F$, $-R_e-Cl$, $-R_e-Br$, $-R_e-I$, $-R_e(F)-$, $-R_e(Cl)-$, $-R_e(Br)-$ and $-R_e(I)-$, wherein $R_e$ is an alkyl, cycloalkyl or heterocycloalkyl.

As used herein, unless specified otherwise, the term "alkylthio" means an alkyl, cycloalkyl or heterocycloalkyl, which contains one or more sulfur atoms. Examples of alkylthio include, but are not limited to, $-CH_2-SH$, $-SCH_3$, $-S-R_e$, $-R_e-SH$, $-R_{e1}-S-R_{e2}-$, wherein $R_e$, $R_{e1}$ and $R_{e2}$ are the same or different alkyl, cycloalkyl or heterocycloalkyl.

As used herein, unless specified otherwise, the term "alkylamino" means an alkyl, cycloalkyl or heterocycloalkyl, which contains one or more nitrogen atoms. Examples of alkylamino include, but are not limited to, $-CH_2-NH$, $-NCH_3$, $-N(R_{e1})-R_{e2}$, $-N-R_e$, $-R_e-NH_2$, $-R_{e1}-N-R_{e2}$ and $-R_e-N(R_{e1})-R_{e2}$ wherein $R_e$, $R_{e1}$ and $R_{e2}$ are the same or different alkyl, cycloalkyl or heterocycloalkyl.

As used herein, unless specified otherwise, the term "alkylcarbonyl" means an alkyl, cycloalkyl or heterocycloalkyl, which contains one or more carbonyl groups. Examples of alkylcarbonyl group include, but are not limited to, aldehyde group ($-R_e-C(O)-H$), ketone group ($-R_e-C(O)-R_{e1}$), carboxylic acid group ($R_e-C(=O)OH$), ester group ($-R_e-C(=O)O-R_{e1}$), carboxamide, ($-R_e-C(=O)O-N(R_{e1})R_{e2}$), enone group ($-R_e-C(O)-C(R_{e1})=C(R_{e2})R_{e3}$), acyl halide group ($-R_e-C(O)-X_h$) and acid anhydride group ($-R_e-C(O)-O-C(O)-R_{e1}$), wherein $R_e$, $R_{e1}$, $R_{e2}$ and $R_{e3}$ are the same or different alkyl, cycloalkyl, or heterocycloalkyl; and $X_h$ is a halogen.

As used herein, unless specified otherwise, the term "perfluoroalkyl" means an alkyl, cycloalkyl or heterocycloalkyl, which contains one or more fluoro group, including, without limitation, perfluoromethyl, perfluoroethyl, perfluoropropyl.

As used herein, unless specified otherwise, the term "aryl" means a chemical structure comprising one or more aromatic rings. In certain embodiments, the ring atoms are all carbon. In certain embodiments, one or more ring atoms are non-carbon, e.g. oxygen, nitrogen, or sulfur ("heteroaryl"). Examples of aryl include, without limitation, phenyl, benzyl, naphthalenyl, anthracenyl, pyridyl, quinoyl, isoquinoyl, pyrazinyl, quinoxalinyl, acridinyl, pyrimidinyl, quinazolinyl, pyridazinyl, cinnolinyl, imidazolyl, benzimidazolyl, purinyl, indolyl, furanyl, benzofuranyl, isobenzofuranyl, pyrrolyl, indolyl, isoindolyl, thiophenyl, benzothiophenyl, pyrazolyl, indazolyl, oxazolyl, benzoxazolyl, isoxazolyl, benzisoxazolyl, thiaxolyl, quanidino and benzothiazolyl.

II. Pharmaceutical Compositions Comprising HPPs

Another aspect of the invention relates to a pharmaceutical composition comprising at least one HPP of a parent drug that can be used to treat pulmonary conditions (e.g. asthma, lower, and upper respiratory tract infections, chronic bronchitis, chronic obstructive pulmonary disease, emphysema, cystic fibrosis, pneumonia, sarcoidosis, and pulmonary fibrosis) or a related compound thereof, and a pharmaceutically acceptable carrier.

A pharmaceutical composition may comprise more than one HPP of different parent drugs. The different parent drugs can belong to the same or different categories of drugs that are used to treat pulmonary conditions (e.g. asthma, lower, and upper respiratory tract infections, chronic bronchitis, chronic obstructive pulmonary disease, emphysema, cystic fibrosis, pneumonia, sarcoidosis, and pulmonary fibrosis). For example, a pharmaceutical composition may comprise HPPs of parent drugs or related compounds thereof, the parent drugs being selected from the group consisting of antihistamines, β2-adrenergic receptor agonists, anti-inflammatory drugs, cough suppressants, decongestants, antibiotics, and any combinations thereof.

A pharmaceutical composition may comprise HPPs of parent drugs of the same class of drugs that can be used to treat pulmonary conditions. For example, a pharmaceutical composition may comprise HPPs of more than one antihistamines, β2-adrenergic receptor agonists, anti-inflammatory drugs, cough suppressants, decongestants, and/or antibiotics.

A pharmaceutical composition may comprise more than one high penetration prodrug, the first parent drug selected from the group consisting of antihistamines, β2-adrenergic receptor agonists, anti-inflammatory drugs, cough suppressants, decongestants, antibiotics, and any combination thereof. The pharmaceutical composition may further comprise at least a second parent drug selected from the group consisting of antihistamines, β2-adrenergic receptor agonists, 5-lipoxygenase-activating protein (FLAP) inhibitors, 5-lipoxygenase inhibitors, leukotriene receptor antagonists, anti-inflammatory drugs, cough suppressants, decongestants, antibiotics, and any combination thereof. The second parent drug may also be selected from the group consisting of dextromethorphan, pentoxyverine, clemastine, diphenhydramine, doxylamine, desloratadine, chlorophenamine, ephedrine, and levomethamphetamin.

A pharmaceutical composition may further comprise drugs that can penetrate biological barriers efficiently (e.g. penetrating skin at a rate>0.01 mg/cm²/h). Examples of such drugs include, without limitation, dextromethorphan, pentoxyverine, clemastine, diphenhydramine, doxylamine, desloratadine, chlorophenamine, ephedrine, and levomethamphetamine A pharmaceutical composition may further comprise one or more cGMP-specific phosphodiesterase type 5 (PDE5) inhibitors, sildenafil, vardenafil, tadalafil, acetildenafil, avanafil, lodenafil, mirodenafil, udenafil, and derivatives and salts thereof. Examples of cGMP-specific phosphodiesterase type 5 (PDE5) inhibitors and derivatives and salts thereof include, without limitation, Structure PDE5-I-1, Structure PDE5-I-2, Structure PDE5-I-3, Structure PDE5-I-4, Structure PDE5-I-5, Structure PDE5-I-6, Structure PDE5-I-7, and Structure PDE5-I-8 shown below. More specifically, Structure PDE5-I-1 is a salt of sildenafil, Structure PDE5-I-2 is a salt of vardenafil, Structure PDE5-I-3 is a salt of tadalafil, Structure PDE5-I-4 is a salt of acetildenafil, Structure PDE5-I-5 is a derivative of avanafil, Structure PDE5-I-6 is lodenafil, Structure PDE5-I-7 is a salt of mirodenafil, and Structure PDE5-I-8 is a salt of udenafil.

Structure PDE5-I-3

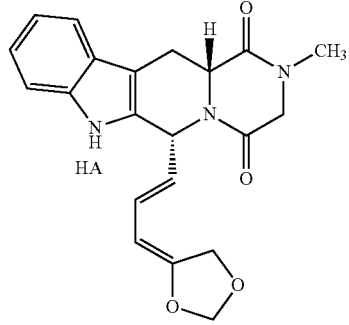

Structure PDE5-I-4

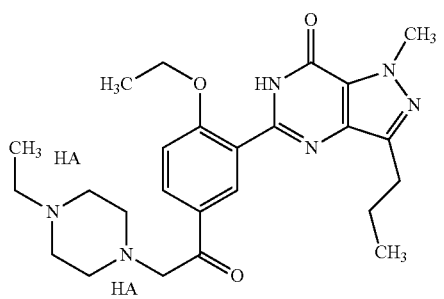

Structure PDE5-I-5

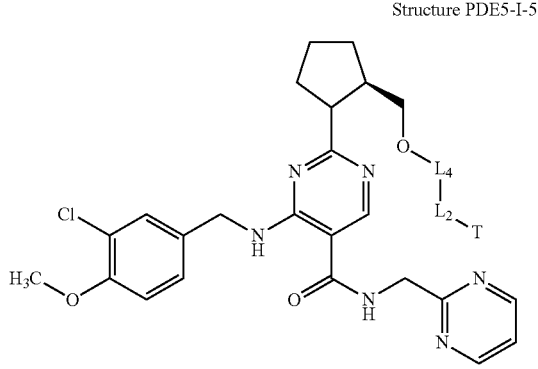

Structure PDE5-I-1

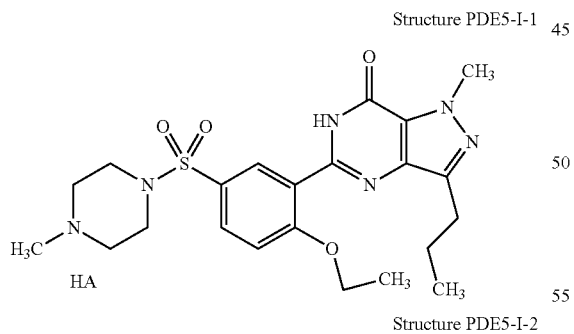

Structure PDE5-I-2

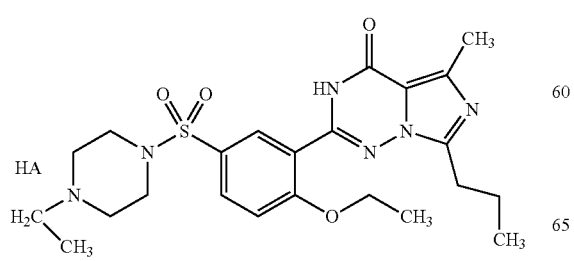

Structure PDE5-I-6

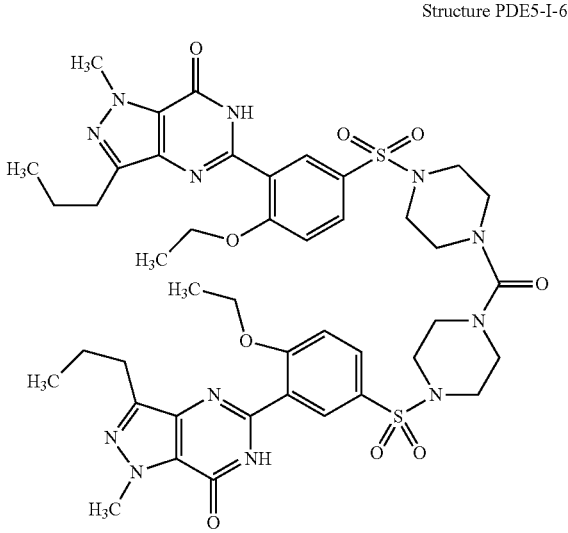

-continued

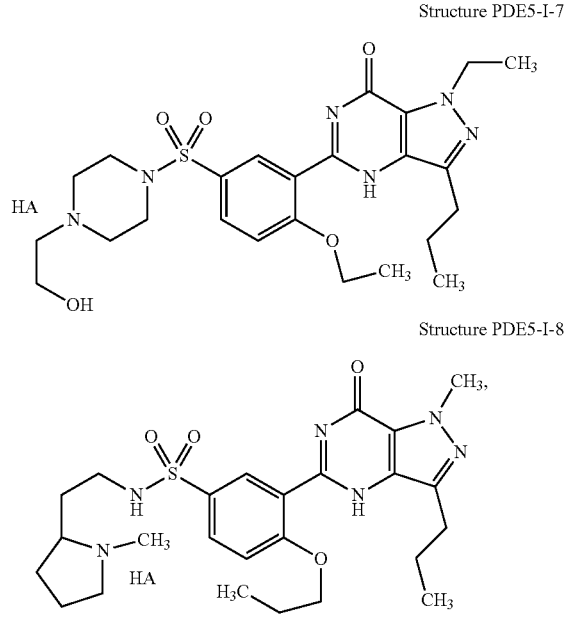

Structure PDE5-I-7

Structure PDE5-I-8

HA, T, $L_2$, and $L_4$ being defined the same as supra.

A pharmaceutical composition may further comprise water.

A pharmaceutical composition may further comprise an alcohols (e.g., ethanol, glycerol, isopropanol, octanol, etc.).

In certain embodiments, a pharmaceutical composition comprises HPPs of parent drugs or related compounds thereof, the parent drugs being penicillin V and/or other antibiotics, for example, a compound comprising a structure of Structure AB-1; aspirin and/or other anti-inflammatory drugs, for example, a compound comprising a structure selected from the group consisting of Structure NSAID-1, Structure NSAID-2, Structure NSAID-3, Structure NSAID-4, Structure NSAID-5, Structure NSAID-6, Structure NSAID-7, NSAID-8, Structure NSAID-9, Structure NSAID-10, Structure NSAID-11, Structure NSAID-12, and Structure NSAID-13; zileuton and/or other 5-lipoxygenase inhibitors, for example, a compound comprising a structure selected from the group consisting of Structure 5-LI-1, Structure 5-LI-2, Structure 5-LI-3, Structure 5-LI-4, Structure 5-LI-5, and Structure 5-LI-6; metaproterenol and/or other leukotriene receptor antagonists, for example, a compound comprising a structure selected from the group consisting of Structure LRA-1, Structure LRA-2, Structure LRA-3, Structure LRA-4, Structure LRA-5, and Structure LRA-6; and fexofenadine and/or other antihistamines, for example, a compound comprising a structure selected from the group consisting of Structure AH-1, Structure AH-2, Structure AH-3, Structure AH-4, Structure AH-5, Structure AH-6, Structure AH-7, Structure AH-8, Structure AH-9, Structure AH-10, Structure AH-11, Structure AH-12, Structure AH-13, Structure AH-14, Structure AH-15, Structure AH-16, Structure AH-17, Structure AH-18, Structure AH-19, and Structure AH-20; MK-886 [3-(1-(4-Chlorobenzyl)-3-t-butylthio-5-isopropylindol-2-yl)-2,2-dimethylpropanoic acid] and/or other 5-lipoxygenase-activating protein (FLAP) inhibitors, for example, a compound comprising a structure selected from the group consisting of Structure FLAP-1, Structure FLAP-2, Structure FLAP-3, Structure FLAP-4, Structure FLAP-5, and Structure FLAP-6; albuterol and/or other β2-adrenergic receptor agonists, for example, a compound comprising a structure selected from the group consisting of Structure ARA-1, Structure ARA-2, Structure ARA-3, Structure ARA-4, Structure ARA-5, Structure ARA-6, Structure ARA-7, Structure ARA-8, Structure ARA-9, Structure ARA-10, Structure ARA-11, Structure ARA-12, Structure ARA-13, and Structure ARA-14; dextromethorphan and/or other cough suppressants, for example, a compound comprising a structure selected from the group consisting of Structure CS-1, Structure CS-2, Structure CS-3, Structure CS-4, Structure CS-5, Structure CS-6, Structure CS-7, Structure CS-8; and/or ephedrine and/or other decongestants, for example, a compound comprising a structure selected from the group consisting of Structure DEC-1, Structure DEC-2, Structure DEC-3, Structure DEC-4, Structure DEC-5, and Structure DEC-6; and/or sildenafil and/or other cGMP-specific phosphodiesterase type 5 (PDE5) inhibitors, for example, a compound comprising a structure selected from the group consisting of Structure PDE5-I-1, Structure PDE5-I-2, Structure PDE5-I-3, Structure PDE5-I-4, Structure PDE5-I-5, Structure PDE5-I-6, Structure PDE5-I-7, and Structure PDE5-I-8.

In certain embodiments, a pharmaceutical composition comprises 6-phenoxyacetacetamidopenicillanic acid 2-diethylaminoethyl ester hydrochloride (a HPP of penicillin V), diethylaminoethyl acetylsalicylate hydrochloride (a HPP of aspirin), (RS)—N-[1-(1-benzothien-2-yl)ethyl]-N-(2-diethylaminoacetyloxyl)urea hydrochloride (a HPP of zileuton), (RS)-5-[1-acetyloxy-2-(isopropylamino)ethyl]benzene-1,3-diol diacetate hydrochloride (a HPP of metaproterenol), and isopropyl(±)-4-[1-hydroxy-4-[4-(hydroxydiphenylmethyl)-1-piperidinyl]-butyl]-α,α-dimethyl benzeneacetate hydrochloride (a HPP of fexofenadine).

In certain embodiments, a pharmaceutical composition comprises HPPs of parent drugs or related compounds thereof, the parent drugs being aspirin, and zileuton.

In certain embodiments, a pharmaceutical composition comprises diethylaminoethyl acetylsalicylate hydrochloride, and (RS)—N-[1-(1-benzothien-2-yl)ethyl]-N-(2-diethylaminoacetyloxyl)urea hydrochloride.

In certain embodiments, a pharmaceutical composition comprises HPPs of parent drugs or related compounds thereof, the parent drugs being cefoxitin, aspirin, montelukast and, metaproterenol, and fexofenadine.

In certain embodiments, a pharmaceutical composition comprises clemastine and HPPs of parent drugs or related compounds thereof, the parent drugs being cefoxitin, aspirin, montelukast, metaproterenol, and fexofenadine.

In certain embodiments, a pharmaceutical composition comprises HPPs of parent drugs or related compounds thereof, the parent drugs being acrivastine, cefoxitin, aspirin, montelukast, and albuterol.

In certain embodiments, a pharmaceutical composition comprises 3-[[(aminocarbonyl)oxy]methyl]-7-methoxy-8-oxo-7-[(2-thienylacetyl)amino]-5-thia-1-azabicyclo[4.2.0]oct-2-ene-2-carboxylic acid 2-diethylaminoethyl ester hydrochloride (HPP of cefoxitin), diethylaminoethyl acetylsalicylate hydrochloride, diethylaminoethyl [R-(E)]-1-[[[1-[3-[2-(7-chloro-2-quinolinyl)ethenyl]phenyl]-3-[2-(1-hydroxy-1-methylethyl)phenyl]propyl]thio]methyl] cyclopropaneacetate hydrochloride, (RS)-5-[2-(tert-butylamino)-1-hydroxyethyl]benzene-1,3-diol diacetate hydrochloride (HPP of terbutaline), and isopropyl (E)-3-{6-[(E)-1-(4-methylphenyl)-3-pyrrolidine-1-yl-prop-1-enyl]pyridin-2-yl}prop-2-enoate (HPP of acrivastine).

In certain embodiments, a pharmaceutical composition comprises HPPs of parent drugs or related compounds thereof, the parent drugs being cefoxitin, ibuprofen, montelukast, albuterol, and acrivastine.

In certain embodiments, a pharmaceutical composition comprises HPPs of parent drugs or related compounds thereof, the parent drugs being acrivastine, cefoxitin, ibuprofen, montelukast, and albuterol.

In certain embodiments, a pharmaceutical composition comprises 3-[[(aminocarbonyl)oxy]methyl]-7-methoxy-8-oxo-7-[(2-thienylacetyl)amino]-5-thia-1-azabicyclo[4.2.0]oct-2-ene-2-carboxylic acid 2-diethylaminoethyl ester hydrochloride, diethylaminoethyl 2-(ρ-isobutylphenyl) propionate hydrochloride, diethylaminoethyl [R-(E)]-1-[[[1-[3-[2-(7-chloro-2-quinolinyl)ethenyl]phenyl]-3-[2-(1-hydroxy-1-methylethyl)phenyl]propyl]thio]methyl]cyclopropaneacetate hydrochloride, (RS)-5-[2-(tert-butylamino)-1-acetyloxyethyl]benzene-1,3-diol diacetate hydrochloride, HPP of terbutaline], and isopropyl (E)-3-{6-[(E)-1-(4-methylphenyl)-3-pyrrolidine-1-yl-prop-1-enyl]pyridin-2-yl}prop-2-enoate.

In certain embodiments, a pharmaceutical composition comprises HPPs of parent drugs or related compounds thereof, the parent drugs being ibuprofen, montelukast, and diethylaminoethyl [R-(E)]-1-[[[1-[3-[2-(7-chloro-2-quinolinyl)ethenyl]phenyl]-3-[2-(1-hydroxy-1-methylethyl)phenyl]propyl]thio]methyl]cyclopropaneacetate hydrochloride, (RS)-5-[2-(tert-butylamino)-1-acetyloxyethyl]benzene-1,3-diol diacetate hydrochloride, HPP of terbutaline], and isopropyl (E)-3-{6-[(E)-1-(4-methylphenyl)-3-pyrrolidine-1-yl-prop-1-enyl]pyridin-2-yl}prop-2-enoate.

In certain embodiments, a pharmaceutical composition comprises HPPs of parent drugs or related compounds thereof, wherein the parent drugs are acrivastine, cefoxitin, ibuprofen, and montelukast. In certain embodiment, the pharmaceutical composition comprises udenafil and HPPs of acrivastine, cefoxitin, ibuprofen, and montelukast.

In certain embodiments, a pharmaceutical composition comprises diethylaminoethyl 2-(ρ-isobutylphenyl) propionate hydrochloride, diethylaminoethyl [R-(E)]-1-[[[1-[3-[2-(7-chloro-2-quinolinyl)ethenyl]phenyl]-3-[2-(1-hydroxy-1-methylethyl)phenyl]propyl]thio]methyl]cyclopropaneacetate hydrochloride, and isopropyl (E)-3-{6-[(E)-1-(4-methylphenyl)-3-pyrrolidine-1-yl-prop-1-enyl]pyridin-2-yl}prop-2-enoate.

In certain embodiments, a pharmaceutical composition comprises HPPs of parent drugs or related compounds thereof, the parent drugs being diclofenac, montelukast, pirbuterol, and acrivastine.

In certain embodiments, a pharmaceutical composition comprises HPPs of parent drugs or related compounds thereof, the parent drugs being acrivastine, diclofenac, montelukast, and pirbuterol.

In certain embodiments, a pharmaceutical composition comprises diethylaminoethyl 2[(2,6-dichlorophenyl)amino]benzene acetate hydrochloride, diethylaminoethyl [R-(E)]-1-[[[1-[3-[2-(7-chloro-2-quinolinyl)ethenyl]phenyl]-3-[2-(1-hydroxy-1-methylethyl)phenyl]propyl]thio]methyl]cyclopropaneacetate, (RS)-6-[2-(tert-butylamino)-1-acetyloxyethyl]-2-(acetyloxymethyl)-3-acetyloxypyridine hydrochloride, and isopropyl (E)-3-{6-[(E)-1-(4-methylphenyl)-3-pyrrolidine-1-yl-prop-1-enyl]pyridin-2-yl}prop-2-enoate.

In certain embodiments, a pharmaceutical composition comprises HPPs of parent drugs or related compounds thereof, the parent drugs being diflunisal, zileuton, terbutaline, and doxylamine.

In certain embodiments, a pharmaceutical composition comprises doxylamine and HPPs of parent drugs or related compounds thereof, the parent drugs being diflunisal, zileuton, and terbutaline.

In certain embodiments, a pharmaceutical composition comprises diethylaminoethyl 5-(2,4-difluorophenyl)salicylate hydrochloride, (RS)—N-[1-(1-benzothien-2-yl)ethyl]-N-(2-diethylaminoacetyloxyl)urea hydrochloride, (±)-α-[(tert-butylamino)methyl]-3,5-diacetyloxybenzyl alcohol hydrochloride, and doxylamine.

In certain embodiments, a pharmaceutical composition comprises HPPs of parent drugs or related compounds thereof, the parent drugs being azlocillin, diflunisal, montelukast, and ephedrine.

In certain embodiments, a pharmaceutical composition comprises ephedrine and HPPs of parent drugs or related compounds thereof, the parent drugs being azlocillin, diflunisal, and montelukast.

In certain embodiments, a pharmaceutical composition comprises (2S,5R,6R)-3,3-dimethyl-7-oxo-6-{[(2R)-2-{[(2-oxoimidazolidin-1-yl)carbonyl]amino}-2-phenylacetyl]amino}-4-thia-1-azabicyclo[3.2.0]heptane-2-carboxylic acid, diethylaminoethyl 5-(2,4-difluorophenyl)salicylate hydrochloride, diethylaminoethyl [R-(E)]-1-[[[1-[3-[2-(7-chloro-2-quinolinyl)ethenyl]phenyl]-3-[2-(1-hydroxy-1-methylethyl)phenyl]propyl]thio]methyl]cyclopropaneacetate hydrochloride, and ephedrine.

In certain embodiments, a pharmaceutical composition comprises HPPs of parent drugs or related compounds thereof, the parent drugs being piperacillin, aspirin, zileuton, metaproterenol, and levomethamphetamine.

In certain embodiments, a pharmaceutical composition comprises levomethamphetamine and HPPs of parent drugs or related compounds thereof, the parent drugs being piperacillin, aspirin, zileuton, and metaproterenol.

In certain embodiments, a pharmaceutical composition comprises 6-D(−)-α-(4-ethyl-2,3-dioxo-1-piperazinylcarbonylamino)-α-phenylacetamidopenicillinic acid 2-diethylaminoethyl ester hydrochloride, 2-diethylaminoethyl 2[(2,6-dichlorophenyl)amino]benzene acetate hydrochloride, diethylaminoethyl acetylsalicylate hydrochloride, (RS)—N-[1-(1-benzothien-2-yl)ethyl]-N-(2-diethylaminoacetyloxyl)urea hydrochloride, (RS)-5-[1-acetyloxy-2-(isopropylamino)ethyl]benzene-1,3-diol diacetate hydrochloride, and levomethamphetamine.

In certain embodiments, a pharmaceutical composition comprises 6-phenoxyacetacetamidopenicillanic acid 2-dimethylaminoethyl ester hydrochloride, diethylaminoethyl acetylsalicylate hydrochloride, (RS)—N-[1-(1-benzothien-2-yl)ethyl]-N-(2-diethylaminoacetyloxyl)urea hydrochloride, sildenafil citrate (structure PDE5-I-1), and isopropyl(±)-4-[1-hydroxy-4-[4-(hydroxydiphenylmethyl)-1-piperidinyl]-butyl]-α, and α-dimethyl benzeneacetate hydrochloride.

In certain embodiments, a pharmaceutical composition comprises 6-phenoxyacetacetamidopenicillanic acid 2-dimethylaminoethyl ester hydrochloride, diethylaminoethyl acetylsalicylate hydrochloride, (RS)—N-[1-(1-benzothien-2-yl)ethyl]-N-(2-diethylaminoacetyloxyl)urea hydrochloride, sildenafil citrate, and isopropyl(±)-4-[1-hydroxy-4-[4-(hydroxydiphenylmethyl)-1-piperidinyl]-butyl]-α, and α-dimethyl benzeneacetate hydrochloride.

In certain embodiments, a pharmaceutical composition comprises diethylaminoethyl 2[(2,6-dichlorophenyl)amino]benzene acetate hydrochloride, diethylaminoethyl [R-(E)]-1-[[[1-[3-[2-(7-chloro-2-quinolinyl)ethenyl]phenyl]-3-[2-(1-hydroxy-1-methylethyl)phenyl]propyl]thio]methyl]cyclopropaneacetate, vardenafil HCl, (R,S)α$^6$-{[(1,1- dimethylethyl)amino]methyl}-3-acetyloxy-2,6-pyridinedimethanol diacetate hydrochloride, and diphenhydramine [2-(diphenylmethoxy)-N,N-dimethylethanamine.

In certain embodiments, a pharmaceutical composition comprises 3-[[(aminocarbonyl)oxy]methyl]-7-methoxy-8-oxo-7-[(2-thienylacetyl)amino]-5-thia-1-azabicyclo[4.2.0]oct-2-ene-2-carboxylic acid 2-diethylaminoethyl ester hydrochloride, diethylaminoethyl acetylsalicylate hydrochloride, diethylaminoethyl [R-(E)]-1-[[[1-[3-[2-(7-chloro-2-quinolinyl)ethenyl]phenyl]-3-[2-(1-hydroxy-1-methylethyl)phenyl]propyl]thio]methyl]cyclopropaneacetate hydrochloride, tadalafil, and clemastine [(2R)-2-{2-[(1R)-1-(4-chlorophenyl)-1-phenylethoxy]ethyl}-1-methylpyrrolidine.

In certain embodiments, a pharmaceutical composition comprises 3-[[(aminocarbonyl)oxy]methyl]-7-methoxy-8-oxo-7-[(2-thienylacetyl)amino]-5-thia-1-azabicyclo[4.2.0]oct-2-ene-2-carboxylic acid 2-diethylaminoethyl ester hydrochloride, diethylaminoethyl 2-(ρ-isobutylphenyl) propionate hydrochloride, diethylaminoethyl [R-(E)]-1-[[[1-[3-[2-(7-chloro-2-quinolinyl)ethenyl]phenyl]-3-[2-(1-hydroxy-1-methylethyl)phenyl]propyl]thio]methyl] cyclopropaneacetate hydrochloride, udenafil, and clemastine.

In certain embodiments, a pharmaceutical composition comprises 6-phenoxyacetacetamidopenicillanic acid 2-dimethylaminoethyl ester hydrochloride, diethylaminoethyl acetylsalicylate hydrochloride, (RS)—N-[1-(1-benzothien-2-yl)ethyl]-N-(2-diethylaminoacetyloxyl)urea hydrochloride, sildenafil citrate, and isopropyl(±)-4-[1-hydroxy-4-[4-(hydroxydiphenylmethyl)-1-piperidinyl]-butyl]-α, and α-dimethyl benzeneacetate hydrochloride. In certain embodiments, a pharmaceutical composition comprises 3-[[(aminocarbonyl)oxy]methyl]-7-methoxy-8-oxo-7-[(2-thienylacetyl)amino]-5-thia-1-azabicyclo[4.2.0]oct-2-ene-2-carboxylic acid 2-diethylaminoethyl ester hydrochloride, diethylaminoethyl acetylsalicylate hydrochloride, diethylaminoethyl [R-(E)]-1-[[[1-[3-[2-(7-chloro-2-quinolinyl)ethenyl]phenyl]-3-[2-(1-hydroxy-1-methylethyl)phenyl]propyl]thio]methyl]cyclopropaneacetate hydrochloride, acetildenafil, and isopropyl (E)-3-{6-[(E)-1-(4-methylphenyl)-3-pyrrolidine-1-yl-prop-1-enyl]pyridin-2-yl}prop-2-enoate.

In certain embodiments, a pharmaceutical composition comprises 6-phenoxyacetacetamidopenicillanic acid 2-dimethylaminoethyl ester hydrochloride, diethylaminoethyl acetylsalicylate hydrochloride, (RS)—N-[1-(1-benzothien-2-yl)ethyl]-N-(2-diethylaminoacetyloxyl)urea hydrochloride, sildenafil citrate, and isopropyl(±)-4-[1-hydroxy-4-[4-(hydroxydiphenylmethyl)-1-piperidinyl]-butyl]-α, and α-dimethyl benzeneacetate hydrochloride.

In certain embodiments, a pharmaceutical composition comprises levomethamphetamine and HPPs of parent drugs or related compounds thereof, the parent drugs being piperacillin, diclofenac, zileuton, and metaproterenol.

In certain embodiments, a pharmaceutical composition comprises 6-D(-)-α-(4-ethyl-2,3-dioxo-1-piperazinylcarbonylamino)-α-phenylacetamidopenicillinic acid 2-diethylaminoethyl ester hydrochloride, 2-diethylaminoethyl 2[(2,6-dichlorophenyl)amino]benzene acetate hydrochloride, [R-(E)]-1-[[[1-[3-[2-(7-chloro-2-quinolinyl)ethenyl]phenyl]-3-[2-(1-hydroxy-1-methylethyl)phenyl]propyl]thio]methyl] cyclopropaneacetate hydrochloride, acetildenafil, and isopropyl (E)-3-{6-[(E)-1-(4-methylphenyl)-3-pyrrolidine-1-yl-prop-1-enyl]pyridin-2-yl}prop-2-enoate.

In certain embodiments, a pharmaceutical composition comprises 6-phenoxyacetacetamidopenicillanic acid 2-dimethylaminoethyl ester hydrochloride, diethylaminoethyl acetylsalicylate hydrochloride, (RS)—N-[1-(1-benzothien-2-yl)ethyl]-N-(2-diethylaminoacetyloxyl)urea hydrochloride, sildenafil citrate, and isopropyl(±)-4-[1-hydroxy-4-[4-(hydroxydiphenylmethyl)-1-piperidinyl]-butyl]-α, and α-dimethyl benzeneacetate hydrochloride.

In certain embodiments, a pharmaceutical composition comprises levomethamphetamine and HPPs of parent drugs or related compounds thereof, the parent drugs being piperacillin, diclofenac, zileuton, and metaproterenol. (RS)—N-[1-(1-benzothien-2-yl)ethyl]-N-(2-diethylaminoacetyloxyl)urea hydrochloride, and (RS)-5-[1-acetyloxy-2-(isopropylamino)ethyl]benzene-1,3-diol diacetate hydrochloride.

In certain embodiments, the pharmaceutical composition comprises HPPs of penicillin V, aspirin, zileuton, metaproterenol, and fexofenadine.

In certain embodiments, the pharmaceutical composition comprises clemastine and HPPs of cefoxitin, aspirin, montelukast, and terbutaline.

In certain embodiments, the pharmaceutical composition comprises clemastine, and HPPs of cefoxitin, ibuprofen, montelukast, and terbutaline.

In certain embodiments, the pharmaceutical composition comprises diphenhydramine, and HPPs of diclofenac, montelukast, and pirbuterol In certain embodiments, the pharmaceutical composition comprises doxylamine, and HPPs of diflunisal, zileuton, and terbutaline.

In certain embodiments, the pharmaceutical composition comprises ephedrine, and HPPs of penicillin V, diflunisal, and montelukast.

In certain embodiments, the pharmaceutical composition comprises levomethamphetamine, and HPPs of piperacillin, diclofenac, zileuton, and metaproterenol.

In certain embodiments, the pharmaceutical composition comprises HPPs of piperacillin, aspirin, zileuton, metaproterenol, and acrivastine In certain embodiments, the pharmaceutical composition comprises sildenafil·citric acid, and HPPs of penicilin V, aspirin, zileuton, and fexofenadine.

In certain embodiments, the pharmaceutical composition comprises vardenafil·HCl, and HPPs of penicilin V, aspirin, zileuton, and fexofenadine.

In certain embodiments, the pharmaceutical composition comprises tadalafil hydrochloride, and HPPs of cefoxitin, aspirin, montelukast, and acrivastine.

In certain embodiments, the pharmaceutical composition comprises udenafil hydrochloride, and HPPs of cefoxitin, ibuprofen, montelukast, and acrivastine.

In certain embodiments, the pharmaceutical composition comprises sildenafil citrate, and HPPs of penicilin V, ibuprofen, zileuton, and fexofenadine.

In certain embodiments, the pharmaceutical composition comprises vardenafil hydrochloride, and HPPs of penicilin V, ibuprofen, zileuton, and fexofenadine.

The term "pharmaceutically acceptable carrier" as used herein means a pharmaceutically-acceptable material, composition or vehicle, such as a liquid or solid filler, diluent, excipient, solvent or encapsulating material, involved in carrying or transporting an HPP from one location, body fluid, tissue, organ (interior or exterior), or portion of the body, to another location, body fluid, tissue, organ, or portion of the body.

Each carrier is "pharmaceutically acceptable" in the sense of being compatible with the other ingredients, e.g., an HPP, of the formulation and suitable for use in contact with the tissue or organ of a biological subject without excessive toxicity, irritation, allergic response, immunogenicity, or other problems or complications, commensurate with a reasonable benefit/risk ratio.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) alcohol, such as ethyl alcohol and propane alcohol; (20) phosphate buffer solutions; and (21) other non-toxic compatible substances employed in pharmaceutical formulations such as acetone.

The pharmaceutical compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

In one embodiment, the pharmaceutically acceptable carrier is an aqueous carrier, e.g. buffered saline and the like. In certain embodiments, the pharmaceutically acceptable carrier is a polar solvent, e.g. acetone and alcohol.

The concentration of HPP in these formulations can vary widely, and will be selected primarily based on fluid volumes, viscosities, body weight and the like in accordance with the particular mode of administration selected and the biological subject's needs. For example, the concentration can be 0.0001% to 100%, 0.001% to 50%, 0.01% to 30%, 0.1% to 20%, 1% to 10% wt.

The compositions of the invention can be administered for prophylactic, therapeutic, and/or hygienic use. Such administration can be topical, mucosal, e.g., oral, nasal, vaginal, rectal, parenteral, transdermal, subcutaneous, intramuscular, intravenous, via inhalation, ophthalmic and other convenient routes. The pharmaceutical compositions can be administered in a variety of unit dosage forms depending upon the method of administration. For example, unit dosage forms suitable for oral administration include powder, tablets, pills, capsules and lozenges and for transdermal administration include solution, suspension and gel.

Thus, a typical pharmaceutical composition for transdermal, oral, and intravenous administrations would be about $10^{-8}$ g to about 100 g, about $10^{-8}$ g to about $10^{-5}$ g, about $10^{-6}$ g to about 1 g, about $10^{-6}$ g to about 100 g, about 0.001 g to about 100 g, about 0.01 g to about 10 g, or about 0.1 g to about 1 g per subject per day. Dosages from about 0.001 mg, up to about 100 g, per subject per day may be used. Actual methods for preparing parenterally administrable compositions will be known or apparent to those skilled in the art and are described in more detail in such publications as Remington: The Science and Practice of Pharmacy 21st ed., Lippincott Williams & Wilkins, (2005).

III. Applications of HPPs i) Methods for Penetrating a Biological Barrier

Another aspect of the invention relates to a method of using a composition of the invention in penetrating one or more biological barriers in a biological subject. The method comprises a step of administering to a biological subject an HPP or a pharmaceutical composition thereof. In certain embodiments, an HPP exhibits more than about 20 times or higher, 50 times or higher, >about 100 times or higher, >about 200 time higher, >about 300 times or higher, >about 500 times or higher, >about 1,000 times or higher penetration rate through one or more biological barriers than its parent drug.

The term "biological barrier" as used herein refers to a biological layer that separates an environment into different spatial areas or compartments, which separation is capable of modulating (e.g. restricting, limiting, enhancing or taking no action in) the passing through, penetrating or translocation of substance or matter from one compartment/area to another. The different spatial areas or compartments as referred to herein may have the same or different chemical or biological environment(s). The biological layer as referred herein includes, but is not limited to, a biological membrane, a cell layer, a biological structure, an inner surface of subjects, organisms, organs or body cavities, an external surface of subjects, organisms, organs or body cavities, or any combination or plurality thereof.

Examples of a biological membrane include a lipid bilayer structure, eukaryotic cell membrane, prokaryotic cell membrane, and intracellular membrane (e.g., nucleus or organelle membrane, such as membrane or envelope of Golgi apparatus, rough and smooth endoplasmic reticulum (ER), ribosomes, vacuoles, vesicles, liposomes, mitochondria, lysosome, nucleus, chloroplasts, plastids, peroxisomes or microbodies).

The lipid bilayer referred to herein is a double layer of lipid-class molecules, including, but not limited to, phospholipids and cholesterol. In a particular embodiment, lipids for bilayer are amphiphilic molecules consisting of polar head groups and non-polar fatty acid tails. The bilayer is composed of two layers of lipids arranged so that their hydrocarbon tails face one another to form an oily core held together by the hydrophobic effect, while their charged heads face the aqueous solutions on either side of the membrane. In another particular embodiment, the lipid bilayer may contain one or more embedded protein and/or sugar molecule(s).

Examples of a cell layer include a lining of eukaryotic cells (e.g., epithelium, lamina propria and smooth muscle or muscularis mucosa (in gastrointestinal tract)), a lining of prokaryotic cells (e.g., surface layer or S-layer which refers to a two dimensional structure monomolecular layer composed of identical proteins or glycoproteins, specifically, an S-layer refers to a part of a cell envelope commonly found in bacteria and archaea), a biofilm (a structured community of microorganisms encapsulated within a self-developed polymeric matrix and adherent to a living or inert surface), and a plant cell layer (e.g., empidermis). The cells may be normal cells or pathological cells (e.g. disease cells, cancer cells).

Examples of biological structures include structures sealed by tight or occluding junctions that provide a barrier to the entry of toxins, bacteria and viruses, e.g. the blood milk barrier and the blood brain barrier (BBB). In particular, BBB is composed of an impermeable class of endothelium, which presents both a physical barrier through tight junctions adjoining neighboring endothelial cells and a transport barrier comprised of efflux transporters. The biological structure may also include a mixture of cells, proteins and sugars (e.g. blood clots).

Examples of the inner surface of subjects, organisms, organs or body cavities include buccal mucosa, esophageal mucosa, gastric mucosa, intestinal mucosa, olfactory mucosa, oral mucosa, bronchial mucosa, uterine mucosa and endometrium (the mucosa of the uterus, inner layer of the wall of a pollen grain or the inner wall layer of a spore), or a combination or plurality thereof.

Examples of the external surface of subjects, organisms, organs or body cavities include capillaries (e.g. capillaries in the heart tissue), mucous membranes that are continuous with skin (e.g. such as at the nostrils, the lips, the ears, the genital area, and the anus), outer surface of an organ (e.g. liver, lung, stomach, brain, kidney, heart, ear, eye, nose, mouth, tongue, colon, pancreas, gallbladder, duodenum, rectum stomach, colonrectum, intestine, vein, respiratory system, vascular, anorectum and pruritus ani), skin, cuticle (e.g. dead layers of epidermal cells or keratinocytes or superficial layer of overlapping cells covering the hair shaft of an animal, a multi-layered structure outside the epidermis of many invertebrates, plant cuticles or polymers cutin and/or cutan), external layer of the wall of a pollen grain or the external wall layer of a spore), and a combination or plurality thereof.

In addition, a biological barrier further includes a sugar layer, a protein layer or any other biological layer, or a combination or plurality thereof. For example, skin is a biological barrier that has a plurality of biological layers. A skin comprises an epidermis layer (outer surface), a demis layer and a subcutaneous layer. The epidermis layer contains several layers including a basal cell layer, a spinous cell layer, a granular cell layer, and a stratum corneum. The cells in the epidermis are called keratinocytes. The stratum corneum ("horny layer") is the outmost layer of the epidermis, wherein cells here are flat and scale-like ("squamous") in shape. These cells contain a lot of keratin and are arranged in overlapping layers that impart a tough and oilproof and waterproof character to the skin's surface.

ii) Methods for Screening a Substance for a Desired Character

Another aspect of the invention relates to a method of screening an HPP for a desired character.

In certain embodiments, the method comprises:
1) covalently linking a test functional unit to a transportational unit through a linker to form a test composition (or covalently linking a functional unit to a test transportational unit through a linker, or covalently linking a functional unit to a transportational unit through a test linker)
2) administrating the test composition to a biological subject; and
3) determining whether the test composition has the desired nature or character.

In one embodiment, a desired character may include, for example, 1) the ability of a test functional unit to form a high penetration composition or convert back to a parent drug, 2) the penetration ability and/or rate of a test composition, 3) the efficiency and/or efficacy of a test composition, 4) the transportational ability of a test transportational unit, and 5) the cleavability of a test linker.

iii) Methods for Treating a Pulmonary Condition in a Biological Subject

Another aspect of the invention relates to a method of using a composition of the invention, or a pharmaceutical composition thereof in treating a condition in a biological subject. The method comprises administrating the pharmaceutical composition to the biological subject.

The term "treating" as used herein means curing, alleviating, inhibiting, or preventing. The term "treat" as used herein means cure, alleviate, inhibit, or prevent. The term "treatment" as used herein means cure, alleviation, inhibition or prevention.

The term "biological subject," or "subject" as used herein means an organ, a group of organs that work together to perform a certain task, an organism, or a group of organisms. The term "organism" as used herein means an assembly of molecules that function as a more or less stable whole and has the properties of life, such as animal, plant, fungus, or micro-organism.

The term "animal" as used herein means a eukaryotic organism characterized by voluntary movement. Examples of animals include, without limitation, vertebrata (e.g. human, mammals, birds, reptiles, amphibians, fishes, marsipobranchiata and leptocardia), tunicata (e.g. thaliacea, appendicularia, sorberacea and ascidioidea), articulata (e.g. insecta, myriapoda, malacapoda, arachnida, pycnogonida, merostomata, crustacea and annelida), gehyrea (anarthropoda), and helminthes (e.g. rotifera).

The term "plant" as used herein means organisms belonging to the kingdom Plantae. Examples of plant include, without limitation, seed plants, bryophytes, ferns and fern allies. Examples of seed plants include, without limitation, cycads, ginkgo, conifers, gnetophytes, angiosperms. Examples of bryophytes include, without limitation, liverworts, hornworts and mosses. Examples of ferns include, without limitation, ophioglossales (e.g. adders-tongues, moonworts, and grape-ferns), marattiaceae and leptosporangiate ferns. Examples of fern allies include, without limitation, lycopsida (e.g. clubmosses, spikemosses and quillworts), psilotaceae (e.g. lycopodiophyta and whisk ferns) and equisetaceae (e.g. horsetails).

The term "fungus" as used herein means a eukaryotic organism that is a member of the kingdom Fungi. Examples of fungus include, without limitation, chytrids, blastocladiomycota, neocallimastigomycota, zygomycota, glomeromycota, ascomycota and basidiomycota.

The term "microorganism" as used herein means an organism that is microscopic (e.g. with length scale of micrometer). Examples of microorganism include, without limitation, bacteria, fungi, archaea, protists and microscopic plants (e.g. green algae) and microscopic animals (e.g. plankton, planarian and amoeba).

Some examples of the conditions the method can treat include conditions that can be treated by the parent drug of the HPP. For example, without limitation, asthma, lower, and upper respiratory tract infections, allergic rhinitis, allergic conjunctivitis, itchiness, and runny nose.

v). Methods of Using HPPs and Pharmaceutical Compositions Thereof in Treatments of Pulmonary Conditions Another aspect of the invention relates to a method of using HPPs or pharmaceutical compositions thereof in treating a pulmonary condition in a biological subject or subject by administrating one or more HPPs or a pharmaceutical composition thereof to the biological subject or subject.

Such pulmonary conditions include, but are not limited to, asthma, lower, and upper respiratory tract infections, chronic bronchitis, chronic obstructive pulmonary disease, emphysema, cystic fibrosis, pneumonia, sarcoidosis, pulmonary fibrosis, allergic rhinitis, allergic conjunctivitis, itchiness, and runny nose.

In certain embodiments, a method of treating a pulmonary condition in a subject comprises administering a therapeutic effective amount of the one or more HPPs, or a pharmaceutical composition thereof to the subject.

In certain embodiments, a pharmacy composition as described supra comprises a first group of HPP(s) and a pharmaceutically acceptable carrier, wherein the parent drug(s) of the first group of HPP(s) are the first group of parent drug(s) comprising at least one parent drug selected from the group consisting of antihistamines, β2-adrenergic receptor agonists, 5-lipoxygenase-activating protein (FLAP) inhibitors, 5-lipoxygenase inhibitors, leukotriene receptor antagonists, anti-inflammatory drugs, cough suppressants, and decongestants. The parent drug(s) of the first group of parent drug(s) can be the same or different, and can be of the same or different type of parent drugs. Said pharmaceutical composition may further comprise a second group of HPP(s), wherein the parent drug(s) of the second group of HPPs are the second group of parent drug(s), and at least one parent drug of the second group of parent drug(s) is selected from the group consisting of antibiotic and anti-inflammatory drugs. The parent drug(s) of the second group of parent drug(s) can be the same or different, and can be of the same or different type of parent drugs. Said pharmaceutical composition may further comprise a third group of drugs selected from the group consisting of sildenafil, vardenafil, tadalafil, acetildenafil, avanafil, lodenafil, mirodenafil, metaproterenol, clemastine, udenafil, and salts thereof, as well as any combination thereof.

In certain embodiments, the first pharmaceutical composition comprises the first group, the second group, and/or the third group of HPP and a pharmaceutically acceptable carrier and the first pharmaceutical composition is applied first to the subject, then after the condition of the subject improves, a second pharmaceutical composition comprising the second group of HPP (e.g. HPP of aspirin) and a pharmaceutically acceptable carrier was administered to the subject to prevent the pulmonary condition from coming back.

The one or more HPPs or a pharmaceutical composition thereof can be administered to a biological subject by any administration route known in the art, including without limitation, oral, enteral, buccal, nasal, topical, rectal, vaginal, aerosol, transmucosal, epidermal, transdermal, dermal, ophthalmic, pulmonary, subcutaneous, and/or parenteral administration. The pharmaceutical compositions can be administered in a variety of unit dosage forms depending upon the method of administration.

A parenteral administration refers to an administration route that typically relates to injection which includes but is not limited to intravenous, intramuscular, intraarterial, intrathecal, intracapsular, intraorbital, intra cardiac, intradermal, intraperitoneal, transtracheal, subcutaneous, subcuticular, intraarticular, subcapsular, subarachnoid, intraspinal, and/or intrasternal injection and/or infusion.

The one or more HPPs or a pharmaceutical composition thereof can be given to a subject in the form of formulations or preparations suitable for each administration route. The formulations useful in the methods of the invention include one or more HPPs, one or more pharmaceutically acceptable carriers therefor, and optionally other therapeutic ingredients. The formulations may conveniently be presented in unit dosage form and may be prepared by any methods well known in the art of pharmacy. The amount of active ingredient which can be combined with a carrier material to produce a single dosage form will vary depending upon the subject being treated and the particular mode of administration. The amount of an HPP which can be combined with a carrier material to produce a pharmaceutically effective dose will generally be that amount of an HPP which produces a therapeutic effect. Generally, out of one hundred percent, this amount will range from about 0.01 percent to about ninety-nine percent of the HPP, preferably from about 0.1 percent to about 20 percent.

Methods of preparing these formulations or compositions include the step of bringing into association an HPP with one or more pharmaceutically acceptable carriers and, optionally, one or more accessory ingredients. In general, the formulations are prepared by uniformly and intimately bringing into association an HPP with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an HPP as an active ingredient. A compound may also be administered as a bolus, electuary, or paste.

In solid dosage forms for oral administration (e.g., capsules, tablets, pills, dragees, powders, granules and the like), the HPP is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate, (5) solution retarding agents, such as paraffin, (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered HPPs or HPP compositions moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of an HPP therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain pacifying agents and may be of a composition that they release the HPP(s) only, or preferentially, in a certain portion of the gastrointestinal tract, optionally, in a delayed manner. Examples of embedding compositions which can be used include polymeric substances and waxes. The HPP can also be in micro-encapsulated form, if appropriate, with one or more of the above-described excipients.

Liquid dosage forms for oral, transdermal or topical administration include pharmaceutically acceptable emulsions, microemulsions, solutions, suspensions, syrups and elixirs. In addition to the HPP, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents.

Suspensions, in addition to the HPP, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more HPPs with one or more suitable non-irritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent. Formulations which are suitable for vaginal administration also include pessaries, tampons, creams, gels, pastes, foams or spray formulations containing such carriers as are known in the art to be appropriate.

Formulations for the topical or transdermal or epidermal or dermal administration of an HPP composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required. The ointments, pastes, creams and gels may contain, in addition to the HPP composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to the HPP composition, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane. The best formulations for the topical or transdermal administration are pure water, solution, aqueous solution, ethanol and water solution, and isopropanol and water solution.

An HPP or a pharmaceutical composition thereof can be alternatively administered by aerosol. This can be accomplished by preparing an aqueous aerosol, liposomal preparation or solid particles containing the HPPs. A nonaqueous (e.g., fluorocarbon propellant) suspension could be used. Sonic nebulizers can also be used. An aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches can also be used to deliver HPP compositions to a target site. Such formulations can be made by dissolving or dispersing the agent in the proper medium. Absorption enhancers can also be used to increase the flux of the HPP compositions across the skin. The rate of such flux can be controlled by either providing a rate controlling membrane or dispersing the HPP compositions in a polymer matrix or gel.

Ophthalmic formulations, eye ointments, powders, solutions and the like, are also contemplated as being within the scope of this invention.

Formulations suitable for parenteral administration comprise an HPP in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacterostats, solutes which render the formulation isotonic with the blood of the intended recipient or suspending or thickening agents.

Examples of suitable aqueous and nonaqueous carriers which may be employed in the formulations suitable for parenteral administration include water, ethanol, polyols (e.g., such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Formulations suitable for parenteral administration may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Injectable depot forms are made by forming microencapsule matrices of an HPP or in biodegradable polymers such as polylactide-polyglycolide. Depending on the ratio of the HPP to polymer, and the nature of the particular polymer employed, the rate of drug release can be controlled. Examples of other biodegradable polymers include poly (orthoesters) and poly (anhydrides). Depot injectable formulations are also prepared by entrapping the HPP in liposomes or microemulsions which are compatible with body tissue.

In certain embodiments, one or more HPPs or a pharmaceutical composition thereof is delivered to an action site in a therapeutically effective dose. As is known in the art of pharmacology, the precise amount of the pharmaceutically effective dose of an HPP that will yield the most effective results in terms of efficacy of treatment in a given patient will depend upon, for example, the activity, the particular nature, pharmacokinetics, pharmacodynamics, and bioavailability of a particular HPP, physiological condition of the subject (including race, age, sex, weight, diet, disease type and stage, general physical condition, responsiveness to a given dosage and type of medication), the nature of pharmaceutically acceptable carriers in a formulation, the route and frequency of administration being used, and the severity or propensity of the condition that is to be treated. However, the above guidelines can be used as the basis for fine-tuning the treatment, e.g., determining the optimum dose of administration, which will require no more than routine experimentation consisting of monitoring the subject and adjusting the dosage. Remington: The Science and Practice of Pharmacy (Gennaro ed. 20.sup.th edition, Williams & Wilkins PA, USA) (2000).

In certain embodiments, a combination of one or more HPPs and/or other drug(s) is applied to the subject for the desired use (e.g. treatment, screening, etc.).

When applying a combination of a plurality of drugs (e.g. one or more HPPs and/or other drug(s)) to a subject, each drug may be applied separately, or one or more of the drugs may be applied at the same time as separate drugs (e.g. spraying two or more drugs at substantially the same time without mixing the drugs before spraying), or one or more drugs can be mixed together before applying to the subject, or any combination of the above application methods. The drugs may be applied in any order possible.

IV. Advantages

In certain embodiments, since an HPP or HPC of the invention is capable of crossing one or more biological barriers, the HPP or HPC can be administered locally (e.g., topically or transdermally) to reach a location where a condition occurs without the necessity of a systematic administration (e.g., oral or parenteral administration). A local administration and penetration of an HPP or HPC allows the HPP or HPC to reach the same level of local concentration of an agent or drug with much less amount or dosage of HPP or HPC in comparison to a systematic administration of a parent agent or drug; alternatively, a higher level of local concentration which may not be afforded in the systematic administration, or if possible, requires significantly higher dosage of an agent in the systematic administration. The high local concentration of the HPP/HPC or its parent agent if being cleaved enables the treatment of a condition more effectively or much faster than a systematically delivered parent agent and the treatment of new conditions that may not be previously possible or observed. The local administration of the HPP or HPC may allow a biological subject to reduce potential suffering from a systemic administration, e.g., adverse reactions associated with the systematic exposure to the agent, gastrointestinal/renal effects. Additionally, the local administration may allow the HPP or HPC to cross a plurality of biological barriers and reach systematically through, for example, general circulation and thus avoid the needs for systematic administration (e.g., injection) and obviate the pain associated with the parenteral injection.

In certain embodiments, an HPP/HPC or a pharmaceutical composition according to the invention can be administered systematically (e.g., orally, transdermally, or parenterally). The HPP/HPC or the active agent (e.g., drug or metabolite) of the HPP/HPC may enter the general circulation with a faster rate than the parent agent and gain faster access to the action site a condition. Additionally, the HPP/HPC can cross a biological barrier (e.g., blood brain barrier and blood milk barrier) which has not been penetrated if a parent agent is administered alone and thus offer novel treatment of conditions that were be previously possible or observed.

V. Examples

The following examples are provided to better illustrate the claimed invention and are not to be interpreted in any way as limiting the scope of the invention. All specific compositions, materials, and methods described below, in whole or in part, fall within the scope of the invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the invention. It is the intention of the inventors that such variations are included within the scope of the invention. Furthermore, all references cited herein are incorporated by reference in their entireties, as if fully set forth herein.

Example 1

Preparation of an HPP from a Parent Drug

In certain embodiments, a parent compound having the following Structure F-C:

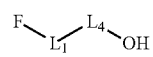

Structure F-C is converted to an HPP having Structure L-1:

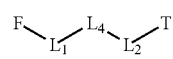

Structure L-1 including stereoisomers and pharmaceutically acceptable salts thereof, wherein:

F, $L_1$, $L_2$, and $L_4$ are defined as supra;

T is a transportational unit of an HPP. For example, T is selected from the group consisting of W and $R_6$ as defined supra.

In certain embodiments of the invention, an HPP having Structure L-1 is prepared according to organic synthesis by reacting the parent compounds or derivatives of the parent compounds having Structure D (e.g. acid halides, mixed anhydrides of the parent compounds, etc.):

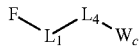

Structure D with compounds of Structure E (Scheme 1):

T-L$_2$-H    Structure E wherein W$_C$ is selected from the group consisting of OH, halogen, alkoxycarbonyl and substituted aryloxycarbonyloxy; and F, L$_1$, L$_2$, L$_4$ and T are defined as supra.

Scheme 1. Preparation of an HPP from a parent compound (I).

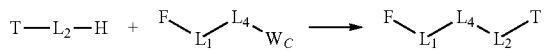

In certain embodiments, an HPP having Structure L-1 is prepared following Scheme 1 as described supra, wherein L$_4$ is C=O.

In certain embodiments, a parent compound having the following Structure F-N:

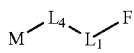

Structure F-N reacts with a compound having the following structure G:

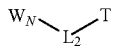

Structure G to obtain an HPP of Structure L-1:

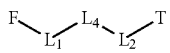

Structure L-1 including stereoisomers and pharmaceutically acceptable salts thereof, wherein:

F, L1, L2, and L4 are defined as supra;

T is a transportational unit of an HPP. For example, T is selected from the group consisting of W and R$_6$ as defined supra; and M is selected from the group consisting of Na, K, or other metal. W$_N$ is selected from the group consisting of OH, halogen, alkoxycarbonyl and substituted aryloxycarbonyloxy. (Scheme 2)

Scheme 2. Preparation of an HPP from a parent compound (II).

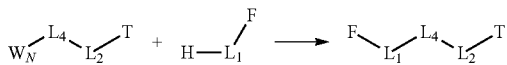

In certain embodiments, an HPP having a structure of Structure L-1 is prepared by organic synthesis wherein the unwanted reactive sites such as —C(=O)OH, —NH$_2$, —OH, or —SH are protected before linking a transportational unit with a functional unit according to one of the synthetic route as described supra. In certain embodiments, the obtained protected HPP may be further partially or completely deprotected to render a partially protected HPP or an unprotected HPP respectively.

Example 2. Treatment of Asthma and/or Other Pulmonary Conditions 30 mg of 6-phenoxyacetacetamidopenicillanic acid 2-diethylaminoethyl ester hydrochloride, 50 mg of diethylaminoethyl acetylsalicylate hydrochloride, 30 mg of (RS)—N-[1-(1-benzothien-2-yl)ethyl]-N-(2-diethylaminoacetyloxyl) urea hydrochloride (an example of a HPP of zileuton), 3 mg of (RS)-5-[1-acetyloxy-2-(isopropylamino)ethyl]benzene-1, 3-diol diacetate hydrochloride (or metaproterenol triacetate hydrochloride, an example of a HPP of metaproterenol), and 30 mg of isopropyl(±)-4-[1-hydroxy-4-[4-(hydroxydiphenylmethyl)-1-piperidinyl]-butyl]-α,α-dimethyl benzeneacetate hydrochloride (an example of a HPP of fexofenadine) in 0.5 mL of water was applied to the skin on the thorax of a subject every morning and evening (twice per day) until the condition was alleviated. Then 50 mg of diethylaminoethyl acetylsalicylate hydrochloride in 0.5 ml of water was applied to the skin on the thorax of the subject every morning and evening (twice per day) to prevent the recurrence of the condition.

Example 3. Treatment of Asthma and/or Other Pulmonary Conditions 30 mg of 6-phenoxyacetacetamidopenicillanic acid 2-diethylaminoethyl ester hydrochloride, 30 mg of diethylaminoethyl acetylsalicylate hydrochloride, 3 mg of diethylaminoethyl [R-(E)]-1-[[[1-[3-[2-(7-chloro-2-quinolinyl) ethenyl]phenyl]-3-[2-(1-hydroxy-1-methylethyl)phenyl] propyl]thio]methyl]cyclopropaneacetate hydrochloride (HPP of montelukast), 3 mg of (RS)-5-[1-acetyloxy-2-(isopropylamino)ethyl]benzene-1,3-diol diacetate hydrochloride (or metaproterenol triacetate hydrochloride, an example of a HPP of metaproterenol), and 30 mg of isopropyl(±)-4-[1-hydroxy-4-[4-(hydroxydiphenylmethyl)-1-piperidinyl]-butyl]-α,α-dimethyl benzeneacetate hydrochloride (an example of a HPP of fexofenadine) in 0.5 ml of water was applied to the skin on the thorax of a subject every morning and evening (twice per day) until the condition was alleviated. Then 30 mg of diethylaminoethyl acetylsalicylate hydrochloride in 0.5 ml of water was applied to the skin on the thorax of the subject every morning and evening (twice per day) to prevent the recurrence of the condition.

Example 4. Treatment of Asthma and/or Other Pulmonary Conditions 6-phenoxyacetacetamidopenicillanic acid 2-diethylaminoethyl ester hydrochloride, 30 mg of diethylaminoethyl acetylsalicylate hydrochloride, 3 mg of diethylaminoethyl [R-(E)]-1-[[[1-[3-[2-(7-chloro-2-quinolinyl)ethenyl]phenyl]-3-[2-(1-hydroxy-1-methylethyl)phenyl]propyl]thio] methyl]cyclopropaneacetate hydrochloride (an example of a HPP of montelukast), 3 mg of (RS)-5-[1-acetyloxy-2-(isopropylamino)ethyl]benzene-1,3-diol diacetate hydrochloride (or metaproterenol triacetate hydrochloride, an example of a HPP of metaproterenol), and 30 mg of isopropyl(±)-4-[1-hydroxy-4-[4-(hydroxydiphenylmethyl)-1-piperidinyl]-butyl]-α,α-dimethyl benzeneacetate hydrochloride (an example of a HPP of fexofenadine) in 0.5 ml of water was applied to the skin on the thorax of a subject every morning and evening (twice per day) until the condition was alleviated. Then 30 mg of diethylaminoethyl acetylsalicylate hydrochloride and 3 mg of clemastine [(2R)-2-{2-[(1R)-1-(4-chlorophenyl)-1-phenylethoxy]ethyl}-1-methylpyrrolidine] in 0.5 ml of water was applied to the skin on the thorax of a subject every morning and evening (twice per day) to prevent the recurrence of the condition.

Example 5. Treatment of Asthma and/or Other Pulmonary Conditions 30 mg of 3-[[(aminocarbonyl)oxy]methyl]-7-methoxy-8-oxo-7-[(2-thienylacetyl)amino]-5-thia-1-azabicyclo[4.2.0]oct-2-ene-2-carboxylic acid 2-diethylaminoethyl ester hydrochloride (HPP of cefoxitin), 15 mg of diethylaminoethyl 2-(ρ-isobutylphenyl) propionate hydrochloride, 3 mg of diethylaminoethyl [R-(E)]-1-[[[1-[3-[2-(7-chloro-2-quinolinyl)ethenyl]phenyl]-3-[2-(1-hydroxy-1-methylethyl) phenyl]propyl]thio]methyl]cyclopropaneacetate hydrochloride (an example of a HPP of montelukast), 2 mg of (RS)-5-[2-(tert-butylamino)-1-acetyloxyethyl]benzene-1,3-diol diacetate hydrochloride, HPP of terbutaline], and 5 mg of isopropyl (E)-3-{6-[(E)-1-(4-methylphenyl)-3-pyrrolidine-1-yl-prop-1-enyl]pyridin-2-yl}prop-2-enoate in 0.5 ml of water was applied to the skin on the thorax of a subject every morning and evening (twice per day) until the condition was alleviated. Then 30 mg of diethylaminoethyl acetylsalicylate hydrochloride and 3 mg of diethylaminoethyl [R-(E)]-1-[[[1-[3-[2-(7-chloro-2-quinolinyl)ethenyl]phenyl]-3-[2-(1-hydroxy-1-methylethyl)phenyl]propyl]thio] methyl]cyclopropaneacetate hydrochloride in 0.5 ml of water was applied to the skin on the thorax of a subject every morning and evening (twice per day) to prevent the recurrence of the condition.

Example 6. Treatment of Allergic Rhinitis, Allergic Conjunctivitis, Itchiness, and Runny Nose 10 mg of diethylaminoethyl 2[(2,6-dichlorophenyl) amino]benzene acetate hydrochloride), 3 mg of diethylaminoethyl [R-(E)-1-[[[1-[3-[2-(7-chloro-2-quinolinyl)ethenyl]phenyl]-3-[2-(1-hydroxy-1-methylethyl)phenyl]propyl] thio]methyl]cyclopropaneacetate, 0.5 mg of (RS)-6-[2-(tert-butylamino)-1-acetyloxyethyl]-2-(acetyloxymethyl)-3-acetyloxypyridine hydrochloride (or pirbuterol triacetate hydrochloride, a HPP of pirbuterol), and 10 mg of diphenhydramine [2-(diphenylmethoxy)-N,N-dimethylethanamine] in 0.5 ml of water was applied to the skin on the thorax of a subject every morning and evening (twice per day) until the condition was alleviated. Then 30 mg of diethylaminoethyl acetylsalicylate hydrochloride and 3 mg of diethylaminoethyl [R-(E)]-1-[[[1-[3-[2-(7-chloro-2-quinolinyl)ethenyl]phenyl]-3-[2-(1-hydroxy-1-methylethyl) phenyl]propyl]thio]methyl]cyclopropaneacetate hydrochloride in 0.5 ml of water was applied to the skin on the thorax of a subject every morning and evening (twice per day) to prevent the recurrence of the condition.

Example 7. Treatment of Allergic Rhinitis, Allergic Conjunctivitis, Itchiness, and Runny Nose 20 mg of diethylaminoethyl 5-(2,4-difluorophenyl)salicylate hydrochloride, 3 mg of diethylaminoethyl [R-(E)]-1-[[[1-[3-[2-(7-chloro-2-quinolinyl)ethenyl]phenyl]-3-[2-(1-hydroxy-1-methylethyl)phenyl]propyl]thio]methyl] cyclopropaneacetate hydrochloride, and 5 mg of isopropyl (E)-3-{6-[(E)-1-(4-methylphenyl)-3-pyrrolidine-1-yl-prop-1-enyl]pyridin-2-yl}prop-2-enoate in 0.5 ml of water was applied to the skin on the thorax of a subject every morning and evening (twice per day) until the condition was alleviated. Then 30 mg of diethylaminoethyl acetylsalicylate hydrochloride in 0.5 ml of water was applied to the skin on the thorax of a subject every morning and evening (twice per day) to prevent the recurrence of the condition.

Example 8. Treatment of Lower Respiratory Tract Infection 30 mg of D-α-[(imidazolidin-2-on-1-yl)carbonylamino] benzylpenicillinic acid 2-pyrrolidinemethyl ester hydrochloride (HPP of azlocillin), 30 mg of diethylaminoethyl 5-(2,4-difluorophenyl)salicylate hydrochloride, 3 mg of diethylaminoethyl [R-(E)]-1-[[[1-[3-[2-(7-chloro-2-quinolinyl)ethenyl]phenyl]-3-[2-(1-hydroxy-1-methylethyl)phenyl]propyl]thio]methyl]cyclopropaneacetate hydrochloride, and 5 mg of isopropyl (E)-3-{6-[(E)-1-(4-methylphenyl)-3-pyrrolidine-1-yl-prop-1-enyl]pyridin-2-yl}prop-2-enoate in 0.5 ml of water was applied to the skin on the thorax of a subject every morning and evening (twice per day) for 2 weeks or until the condition was alleviated. Then 30 mg of diethylaminoethyl acetylsalicylate hydrochloride in 0.5 ml of water was applied to the skin on the thorax of a subject every morning and evening (twice per day) to prevent the recurrence of the condition.

Example 9. Treatment of Upper Respiratory Tract Infection 30 mg of 6-D(−)-α-(4-ethyl-2,3-dioxo-1-piperazinylcarbonylamino)-α-phenylacetamidopenicillinic acid 2-diethylaminoethyl ester hydrochloride (HPP of piperacillin), 10 mg of 2-diethylaminoethyl 2[(2,6-dichlorophenyl)amino]benzene acetate hydrochloride, 30 mg of diethylaminoethyl acetylsalicylate hydrochloride, 30 mg of (RS)—N-[1-(1-benzothien-2-yl)ethyl]-N-(2-diethylaminoacetyloxyl)urea hydrochloride, 3 mg of (RS)-5-[1-acetyloxy-2-(isopropylamino)ethyl]benzene-1,3-diol diacetate hydrochloride, and 5 mg of isopropyl (E)-3-{6-[(E)-1-(4-methylphenyl)-3-pyrrolidine-1-yl-prop-1-enyl]pyridin-2-yl}prop-2-enoate in 0.5 ml of 25% ethanol was applied to the skin on the thorax of a subject every morning and evening (twice per day) for 2 weeks or until the condition was alleviated. Then 30 mg of diethylaminoethyl acetylsalicylate hydrochloride in 0.5 ml of water was applied to the skin on the thorax of a subject every morning and evening (twice per day) to prevent the recurrence of the condition.

Example 10. Treatment of Asthma and/or Other Pulmonary Conditions 30 mg of 6-phenoxyacetacetamidopenicillanic acid 2-dimethylaminoethyl ester hydrochloride, 30 mg of diethylaminoethyl acetylsalicylate hydrochloride, 30 mg of (RS)—N-[1-(1-benzothien-2-yl)ethyl]-N-(2-diethylaminoacetyloxyl)urea hydrochloride (an example of a HPP of zileuton), 15 mg of sildenafil citrate (an example of a compound having structure PDE5-I-1, wherein HA is citric acid), and 30 mg of isopropyl(±)-4-[1-hydroxy-4-[4-(hydroxydiphenylmethyl)-1-piperidinyl]-butyl]-α,α-dimethyl benzeneacetate hydrochloride (an example of a HPP of fexofenadine) in 0.5 ml of 25% ethanol was applied to the skin on the thorax of a subject every morning and evening (twice per day) until the condition was alleviated. Then 30 mg of diethylaminoethyl acetylsalicylate hydrochloride in 0.5 ml of water was applied to the skin on the thorax of a subject every morning and evening (twice per day) to prevent the recurrence of the condition.

Example 11. Treatment of Asthma and/or Other Pulmonary Conditions 30 mg of 6-phenoxyacetacetamidopenicillanic acid 2-diethylaminoethyl ester hydrochloride, 30 mg of diethylaminoethyl acetylsalicylate hydrochloride, 30 mg of (RS)—N-[1-(1-benzothien-2-yl)ethyl]-N-(2-diethylaminoacetyloxyl)urea hydrochloride, 5 mg of vardenafil·HCl (an example of a compound having structure PDE5-I-2, wherein HA is HCl), and 30 mg of isopropyl($\pm$)-4-[1-hydroxy-4-[4-(hydroxydiphenylmethyl)-1-piperidinyl]-butyl]-$\alpha$,$\alpha$-dimethyl benzeneacetate hydrochloride in 0.5 ml of 25% ethanol was applied to the skin on the thorax of a subject every morning and evening (twice per day) for until the condition was alleviated. Then 30 mg of diethylaminoethyl acetylsalicylate hydrochloride in 0.5 ml of water was applied to the skin on the thorax of a subject every morning and evening (twice per day) to prevent the recurrence of the condition.

Example 12. Treatment of Asthma and/or Other Pulmonary Conditions 30 mg of 3-[[(aminocarbonyl)oxy]methyl]-7-methoxy-8-oxo-7-[(2-thienylacetyl)amino]-5-thia-1-azabicyclo[4.2.0]oct-2-ene-2-carboxylic acid 2-diethylaminoethyl ester hydrochloride, 30 mg of diethylaminoethyl acetylsalicylate hydrochloride, 3 mg of diethylaminoethyl [R-(E)]-1-[[[1-[3-[2-(7-chloro-2-quinolinyl)ethenyl]phenyl]-3-[2-(1-hydroxy-1-methylethyl)phenyl]propyl]thio]methyl]cyclopropaneacetate hydrochloride (an example of a HPP of montelukast), 5 mg of tadalafil HCl (an example of a compound having structure PDE5-I-3, wherein HA is HCl), and 5 mg of isopropyl (E)-3-{6-[(E)-1-(4-methylphenyl)-3-pyrrolidine-1-yl-prop-1-enyl]pyridin-2-yl}prop-2-enoate in 0.5 ml of 25% ethanol was applied to the skin on the thorax of a subject every morning and evening (twice per day) for until the condition was alleviated. Then 30 mg of diethylaminoethyl acetylsalicylate hydrochloride in 0.5 ml of water was applied to the skin on the thorax of a subject every morning and evening (twice per day) to prevent the recurrence of the condition.

Example 13. Treatment of Asthma and/or Other Pulmonary Conditions 30 mg of 3-[[(aminocarbonyl)oxy]methyl]-7-methoxy-8-oxo-7-[(2-thienylacetyl)amino]-5-thia-1-azabicyclo[4.2.0]oct-2-ene-2-carboxylic acid 2-diethylaminoethyl ester hydrochloride, 15 mg of diethylaminoethyl 2-(p-isobutylphenyl) propionate hydrochloride, 3 mg of diethylaminoethyl [R-(E)]-1-[[[1-[3-[2-(7-chloro-2-quinolinyl)ethenyl]phenyl]-3-[2-(1-hydroxy-1-methylethyl)phenyl]propyl]thio]methyl]cyclopropaneacetate hydrochloride, 10 mg of udenafil hydrochloride (an example of a compound having structure PDE5-I-8, wherein HA is HCl), and 3 mg of clemastine in 1 ml of water was applied to the skin on the thorax of a subject every morning and evening (twice per day) for 1-2 months; then 30 mg of diethylaminoethyl 2-(p-isobutylphenyl) propionate hydrochloride, 3 mg of diethylaminoethyl [R-(E)]-1-[[[1-[3-[2-(7-chloro-2-quinolinyl)ethenyl]phenyl]-3-[2-(1-hydroxy-1-methylethyl)phenyl]propyl]thio]methyl]cyclopropaneacetate, and 5 mg isopropyl (E)-3-{6-[(E)-1-(4-methylphenyl)-3-pyrrolidine-1-yl-prop-1-enyl]pyridin-2-yl}prop-2-enoate in 0.5 ml of 25% ethanol was applied to the skin on the thorax of a subject every morning and evening (twice per day) for until the condition was alleviated. Then 30 mg of diethylaminoethyl acetylsalicylate hydrochloride in 0.5 ml of water was applied to the skin on the thorax of a subject every morning and evening (twice per day) to prevent the recurrence of the condition.

Example 14. Treatment of Asthma and/or Other Pulmonary Conditions 30 mg of 6-phenoxyacetacetamidopenicillanic acid 2-dimethylaminoethyl ester hydrochloride, 15 mg of diethylaminoethyl 2-(p-isobutylphenyl) propionate hydrochloride, 30 mg of (RS)—N-[1-(1-benzothien-2-yl)ethyl]-N-(2-diethylaminoacetyloxyl)urea hydrochloride (an example of a HPP of zileuton), 10 mg of sildenafil citrate (an example of a compound having structure PDE5-I-1, wherein HA is citric acid), and 30 mg of isopropyl($\pm$)-4-[1-hydroxy-4-[4-(hydroxydiphenylmethyl)-1-piperidinyl]-butyl]-$\alpha$,$\alpha$-dimethyl benzeneacetate hydrochloride (an example of a HPP of fexofenadine) in 0.5 ml of 25% ethanol was applied to the skin on the thorax of a subject every morning and evening (twice per day) for until the condition was alleviated. Then 30 mg of diethylaminoethyl acetylsalicylate hydrochloride in 0.5 ml of water was applied to the skin on the thorax of a subject every morning and evening (twice per day) to prevent the recurrence of the condition.

Example 15. Treatment of Asthma and/or Other Pulmonary Conditions 30 mg of 6-phenoxyacetacetamidopenicillanic acid 2-diethylaminoethyl ester hydrochloride, 15 mg of diethylaminoethyl 2-(p-isobutylphenyl) propionate hydrochloride, 30 mg of (RS)—N-[1-(1-benzothien-2-yl)ethyl]-N-(2-diethylaminoacetyloxyl)urea hydrochloride, 10 mg of vardenafil HCl (an example of a compound of structure PDE5-I-2, wherein HA is HCl), and 30 mg of isopropyl($\pm$)-4-[1-hydroxy-4-[4-(hydroxydiphenylmethyl)-1-piperidinyl]-butyl]-$\alpha$,$\alpha$-dimethyl benzeneacetate hydrochloride in 0.5 ml of 25% ethanol was applied to the skin on the thorax of a subject every morning and evening (twice per day) for until the condition was alleviated. Then 30 mg of diethylaminoethyl acetylsalicylate hydrochloride in 0.5 ml of water was applied to the skin on the thorax of a subject every morning and evening (twice per day) to prevent the recurrence of the condition.

Example 16. Animal Test of Drug Combinations Disclosed Herein 48 female, BALB/c mice between 4 and 6 weeks of age were injected intraperitoneally with 0.4 mL of phosphate-buffered saline containing 50 μg of ovalbumin and 2.0 mg of aluminum hydroxide on day 1 and 8. The immunized mice were exposed to an aerosol of 2.5% ovalbumin in phosphate-buffered saline for 30 minutes/day on day 15 and 22. 12 mice were sham-immunized and challenged with phosphate-buffered saline and assigned as control group (group 1).

The 48 challenged mice were divided randomly into 5 groups: sham-control group (group 1, n=6), negative control group (group 2, n=6), low dose group (group 3, n=12), moderate dose group (group 4, n=12) and high dose group (group 5, n=12). Mice in group 1 (sham-control group) and group 2 (negative control group) were treated with vehicle (25% ethanol/water, the volumes administered were the same as the drug volumes of high dose group) once per day from day 15 to 22.

In group 3 (low dose group), each mouse was applied with a combination of 6-phenoxyacetacetamidopenicillanic acid 3-piperidinemethyl ester hydrochloride (10 mg/kg, 2% solution in 25% ethanol/water, an HPP of penicillin V), dibutylaminoethyl acetylsalicylate hydrochloride (10 mg/kg, 2% solution in 25% ethanol/water, an HPP of aspirin), (RS)—N-[1-(1-benzothien-2-yl)ethyl]-N-(2-diethylaminoacetyloxyl)urea hydrochloride (an HPP of zileuton, structure AS-2) (10 mg/kg, 2% solution in 25% ethanol/water), (RS)-5-[1-acetyloxy-2-(isopropylamino)ethyl]benzene-1,3-diol diacetate hydrochloride (or metaproterenol triacetate hydrochloride, an HPP of metaproterenol, structure AS-4) (1 mg/kg, 0.3% solution in 25% ethanol/water), isopropyl(±)-4-[1-hydroxy-4-[4-(hydroxydiphenylmethyl)-1-piperidinyl]-butyl]-α, and α-dimethyl benzeneacetate hydrochloride (HPP of fexofenadine, structure AS-3) (10 mg/kg, 2% solution in 25% ethanol/water) to the shaved skin on the neck once per day from day 14 to day 22.

In group 4 (moderate dose group), each mouse was applied with a combination of 6-phenoxyacetacetamidopenicillanic acid 3-piperidinemethyl ester hydrochloride (20 mg/kg, 4% solution in 25% ethanol/water), dibutylaminoethyl acetylsalicylate hydrochloride (20 mg/kg, 4% solution in 25% ethanol/water), (RS)—N-[1-(1-benzothien-2-yl)ethyl]-N-(2-diethylaminoacetyloxyl)urea hydrochloride (20 mg/kg, 2% solution in 25% ethanol/water), (RS)-5-[1-acetyloxy-2-(isopropylamino)ethyl]benzene-1,3-diol diacetate hydrochloride (2 mg/kg, 0.6% solution in 25% ethanol/water), and isopropyl(±)-4-[1-hydroxy-4-[4-(hydroxydiphenylmethyl)-1-piperidinyl]-butyl]-α,α-dimethyl benzeneacetate hydrochloride (20 mg/kg, 4% solution in 25% ethanol/water) to the shaved skin on the neck once per day from day 15 to 22.

In group 5 (high dose group), each mouse was applied with a combination of 6-phenoxyacetacetamidopenicillanic acid 3-piperidinemethyl ester hydrochloride (30 mg/kg, 6% solution in 25% ethanol/water), dibutylaminoethyl acetylsalicylate hydrochloride (30 mg/kg, 6% solution in 25% ethanol/water), (RS)—N-[1-(1-benzothien-2-yl)ethyl]-N-(2-diethylaminoacetyloxyl)urea hydrochloride (30 mg/kg, 2% solution in 25% ethanol/water), (RS)-5-[1-acetyloxy-2-(isopropylamino)ethyl]benzene-1,3-diol diacetate hydrochloride (3 mg/kg, 0.9% solution in 25% ethanol/water), and isopropyl(±)-4-[1-hydroxy-4-[4-(hydroxydiphenylmethyl)-1-piperidinyl]-butyl]-α,α-dimethyl benzeneacetate hydrochloride (30 mg/kg, 6% solution in 25% ethanol/water) to the shaved skin on the neck once per day from day 15 to 22.

When applying a combination of a plurality of drugs (e.g. one or more HPPs and/or other drug(s)) to a subject, each drug could be applied separately, or one or more of the drugs could be applied at the same time as separate drugs (e.g. spraying two or more drugs at substantially the same time without mixing the drugs before spraying), or one or more drugs could be mixed together before applying to the subject, or any combination of the above application methods. The drugs could be applied in any order possible.

TABLE 1

Doses of HPPs/Drugs applied to Groups 3, 4, and 5

| | | Drug | | |
| | | Dose (mg/kg) | Dose (mg/kg) | Dose (mg/kg) |
| | | Group No. | | |
| HPP | Parent drug | 3 | 4 | 5 |
| 6-phenoxyacetacetamidopenicillanic acid 3-piperidinemethyl ester hydrochloride | Penicillin V | 10 | 20 | 30 |
| dibutylaminoethyl acetylsalicylate hydrochloride | Aspirin | 10 | 20 | 30 |
| (RS)-N-[1-(1-benzothien-2-yl)ethyl]-N-(2-diethylaminoacetyloxy)urea hydrochloride | Zileuton | 10 | 20 | 30 |
| (RS)-5-[1-acetyloxy-2-(isopropylamino)ethyl]benzene-1,3-diol diacetate hydrochloride, or metaproterenol triacetate hydrochloride | Metaproterenol | 1 | 2 | 3 |
| isopropyl (±)-4-[1-hydroxy-4-[4-(hydroxydiphenylmethyl)-1-piperidinyl]-butyl]-α,α-dimethyl benzeneacetate hydrochloride | Fexofenadine | 10 | 20 | 30 |

Airway responsiveness (transpulmonary resistance (RL) and dynamic compliance (Cdyn)) to inhaled β-methacholine was determined in mice 3 hours after the last treatment with test articles and vehicle (treatment started after the final challenge) at day 21. Animals were anesthetized with ketamine-xylazine, tracheostomized, and mechanically ventilated within a plethysmograph chamber. Volume changes due to thoracic expansion and alterations in tracheal pressure were measured in response to challenge with saline, followed by increasing concentrations of β-methacholine (6.25, 12.5, 25, and 50 mg/mL). Peak values were taken as the maximum response to the concentration of methacholine being tested, and were expressed as the percentage change relative to the saline control. The results are shown in Table 1.1.

TABLE 1.1

| | Airway Hyperresponsiveness | | | | |
|---|---|---|---|---|---|
| | Naïve | Vehicle | Low dose | Moderate dose | High dose |
| Transpulmonary resistance (percent of saline control at 25 mg/ml methacholine) | 149 ± 21* | 316 ± 58 | 187 ± 25* | 156 ± 23* | 148 ± 18* |
| Dynamic compliance (percent of saline control at 25 mg/ml methacholine) | −33.7 ± 3.4* | −62.5 ± 3.7 | −45.2 ± 2.9* | −37.1 ± 3.1* | −34.8 ± 2.7* |

*$P < 0.001$, significant difference compared with vehicle-treated animals

Mice were euthanized with sodium pentobarbitone at day 22. The chest cavity of each animal was carefully opened, after which the trachea was exposed and catheterized. The catheter was secured, and phosphate-buffered saline (PBS) containing 0.5% sodium citrate was infused in three aliquots (0.3, 0.3 and 0.4 mL, respectively) in a total volume of 1 mL. The bronchoalveolar lavage fluid (BALF) was recovered and placed on ice. Total cell counts were immediately performed in a Neubauer chamber. Differential counts were obtained using Rosenfeld-stained cytospin preparations. Following centrifugation (405×g for 5 min at 4° C.), BALF supernatants were collected and stored at −70° C. for subsequent cytokine determinations. The results are shown in Table 1.2.

TABLE 1.2

| | Eosinophil numbers, neutrophil number and mononuclear cell numbers in the Blood and Bronchoalveolar Lavage Fluid (BALF) | | | | |
|---|---|---|---|---|---|
| | Naïve | Vehicle | Low dose | Moderate dose | High dose |
| Eosinophil Numbers in Blood (×10$^6$/mL) | 0.039 ± 0.008* | 0.513 ± 0.105 | 0.180 ± 0.031 | 0.092 ± 0.021* | 0.051 ± 0.018* |
| Neutrophil Number in Blood (×10$^6$/mL) | 0.49 ± 0.16* | 1.01 ± 0.12 | 0.65 ± 0.16* | 0.58 ± 0.14* | 0.46 ± 0.11* |
| Mononuclear cell numbers in Blood (×10$^6$/mL) | 2.49 ± 0.16 | 5.01 ± 0.12 | 2.65 ± 0.56 | 1.47 ± 0.28* | 1.36 ± 0.21* |
| Eosinophil Numbers in BALF (×10$^6$/mL) | 0.29 ± 0.06* | 1.81 ± 0.15 | 0.59 ± 0.17* | 0.38 ± 0.14* | 0.31 ± 0.05* |
| Neutrophil Number in BALF (×10$^6$/mL) | 0.35 ± 0.11 | 0.57 ± 0.13 | 0.41 ± 0.15* | 0.33 ± 0.18* | 0.29 ± 0.11* |
| Mononuclear cell numbers in BALF (×10$^6$/mL) | 0.28 ± 0.05* | 1.07 ± 0.23 | 0.55 ± 0.25* | 0.38 ± 0.20* | 0.31 ± 0.12* |

*$P < 0.001$, significant difference compared with vehicle animals.

Mice lungs were removed, weighed and homogenized in 1.0 mL PBS, centrifuged (405×g for 5 min at 4° C.). The supernatants were collected and stored at −70° C. for subsequent cytokine determinations. Cytokine levels were determined per mg of tissue. Commercially available enzyme-linked immunosorbent assay antibodies were used to measure IL-5 in lung homogenates. Sensitivities were >10 pg/mL. The results are shown in Table 1.3.

TABLE 1.3

| | IL-5 in lung homogenates of animals | | | | |
|---|---|---|---|---|---|
| | Group No. | | | | |
| | 1 | 2 | 3 | 4 | 5 |
| Drug administered | Naïve | Vehicle | Low dose | Moderate dose | High dose |
| IL-5 (pg/mg of tissue) | 0.39 ± 0.12* | 1.11 ± 0.09 | 0.59 ± 0.10* | 0.43 ± 0.08* | 0.37 ± 0.08* |

*$P < 0.001$, significant difference compared with vehicle animals.

The results of this study show that the test drug combinations had strong anti-inflammatory and anti-asthma activities.

Example 17. Animal Test of Drug Combinations Disclosed Herein

Experiments similar to those described in Example 16 were performed. 48 female, BALB/c mice between 4 and 6 weeks of age were prepared and grouped as described in Example 16. Doses and HPPs of the same parent drug but optionally different transportational units were applied as summarized in Table 2.

When applying a combination of a plurality of drugs (e.g. one or more HPPs and/or other drug(s)) to a subject, each drug could be applied separately, or one or more of the drugs could be applied at the same time as separate drugs (e.g. spraying two or more drugs at substantially the same time without mixing the drugs before spraying), or one or more drugs could be mixed together before applying to the subject, or any combination of the above application methods. The drugs could be applied in any order possible.

More specifically, in group 3, each mouse was applied with a combination of 6-phenoxyacetacetamidopenicillanic acid 2-(diethylamino)-1-methylethyl ester hydrochloride (10 mg/kg, 2% solution in 25% ethanol/water), 1-piperidineethyl acetylsalicylate hydrochloride (10 mg/kg, 2% solution in 25% ethanol/water), (RS)—N-[1-(1-benzothien-2-yl)ethyl]-N-(2-diethylaminoacetyloxyl)urea hydrochloride (10 mg/kg, 2% solution in 25% ethanol/water), (RS)-5-[1-acetyloxy-2-(isopropylamino)ethyl]benzene-1,3-diol diacetate hydrochloride (1 mg/kg, 0.3% solution in 25% ethanol/water), and isopropyl(±)-4-[1-hydroxy-4-[4-(hydroxydiphenylmethyl)-1-piperidinyl]-butyl]-α,α-dimethyl benzeneacetate hydrochloride (HPP of fexofenadine, structure AS-3) (10 mg/kg, 2% solution in 25% ethanol/water) to the shaved skin on the neck once per day from day 14 to day 22.

In group 4 (moderate dose group), each mouse was applied with a combination of 6-phenoxyacetacetamidopenicillanic acid 2-diethylaminoethyl ester hydrochloride (20 mg/kg, 4% solution in 25% ethanol/water), 1-piperidineethyl acetylsalicylate hydrochloride (20 mg/kg, 4% solution in 25% ethanol/water), (RS)—N-[1-(1-benzothien-2-yl)ethyl]-N-(2-diethylaminoacetyloxyl)urea hydrochloride (20 mg/kg, 2% solution in 25% ethanol/water), (RS)-5-[1-acetyloxy-2-(isopropylamino)ethyl]benzene-1,3-diol diacetate hydrochloride (2 mg/kg, 0.6% solution in 25% ethanol/water), and isopropyl(±)-4-[1-hydroxy-4-[4-(hydroxydiphenylmethyl)-1-piperidinyl]-butyl]-α,α-dimethyl benzeneacetate hydrochloride (20 mg/kg, 4% solution in 25% ethanol/water) to the shaved skin on the neck once per day from day 15 to 22.

In group 5 (high dose group), each mouse was applied with a combination of 6-phenoxyacetacetamidopenicillanic acid 2-diethylaminoethyl ester hydrochloride (30 mg/kg, 6% solution in 25% ethanol/water), 1-piperidineethyl acetylsalicylate hydrochloride (30 mg/kg, 6% solution in 25% ethanol/water), (RS)—N-[1-(1-benzothien-2-yl)ethyl]-N-(2-diethylaminoacetyloxyl)urea hydrochloride (30 mg/kg, 2% solution in 25% ethanol/water), (RS)-5-[1-acetyloxy-2-(isopropylamino)ethyl]benzene-1,3-diol diacetate hydrochloride (3 mg/kg, 0.9% solution in 25% ethanol/water), and isopropyl(±)-4-[1-hydroxy-4-[4-(hydroxydiphenylmethyl)-1-piperidinyl]-butyl]-α,α-dimethyl benzeneacetate hydrochloride (30 mg/kg, 6% solution in 25% ethanol/water) to the shaved skin on the neck once per day from day 15 to 22.

Airway responsiveness [transpulmonary resistance ($R_L$) and dynamic compliance ($C_{dyn}$)] to inhaled β-methacholine were determined following the same protocol as described in Example 16. The results are shown in Table 2.1.

TABLE 2

Doses of HPPs/Drugs applied to Groups 3, 4, and 5

| HPP | Parent drug | Dose (mg/kg) Group No. 3 | Dose (mg/kg) Group No. 4 | Dose (mg/kg) Group No. 5 |
| --- | --- | --- | --- | --- |
| 6-phenoxyacetacetamidopenicillanic acid 2-(diethylamino)-1-methylethyl ester hydrochloride | Penicillin V | 10 | 20 | 30 |
| 1-piperidineethyl acetylsalicylate hydrochloride | Aspirin | 10 | 20 | 30 |
| (RS)-N-[1-(1-benzothien-2-yl)ethyl]-N-(2-diethylaminoacetyloxy)urea hydrochloride | Zileuton | 10 | 20 | 30 |
| (RS)-5-[1-acetyloxy-2-(isopropylamino)ethyl]benzene-1,3-diol diacetate hydrochloride | Metaproterenol | 1 | 2 | 3 |
| isopropyl (±)-4-[1-hydroxy-4-[4-(hydroxydiphenylmethyl)-1-piperidinyl]-butyl]-α,α-dimethyl benzeneacetate hydrochloride | Fexofenadine | 10 | 20 | 30 |

TABLE 2.1

| | Airway Hyperresponsiveness | | | | |
|---|---|---|---|---|---|
| | Naïve | Vehicle | Low dose | Middle dose | High dose |
| Transpulmonary resistance (percent of saline control at 25 mg/ml methacholine) | 151 ± 23* | 311 ± 68 | 191 ± 21* | 151 ± 20* | 142 ± 17* |
| Dynamic compliance (percent of saline control at 25 mg/ml methacholine) | −32.1 ± 3.0* | −63.5 ± 3.1 | −47.2 ± 2.3* | −39.0 ± 2.8* | −34.1 ± 2.9* |

*$P < 0.001$, significant difference compared with vehicle-treated animals

Eosinophil numbers, neutrophil number and mononuclear cell numbers in BALF were determined following the same protocol as described in Example 16. The results are shown in Table 2.2.

TABLE 2.2

| | Eosinophil numbers, neutrophil number and mononuclear cell numbers in BALF | | | | |
|---|---|---|---|---|---|
| | Naïve | Vehicle | Low dose | Middle dose | High dose |
| Eosinophil Numbers in Blood (×10$^6$/mL) | 0.037 ± 0.010* | 0.529 ± 0.132 | 0.182 ± 0.028 | 0.090 ± 0.014* | 0.047 ± 0.015* |
| Neutrophil Number in Blood (×10$^6$/mL) | 0.51 ± 0.13* | 1.12 ± 0.16 | 0.67 ± 0.18* | 0.62 ± 0.11* | 0.43 ± 0.15* |
| Mononuclear cell numbers in Blood (×10$^6$/mL) | 2.21 ± 0.16 | 5.09 ± 0.17 | 2.69 ± 0.47 | 1.57 ± 0.22* | 1.32 ± 0.25* |
| Eosinophil Numbers in BALF (×10$^6$/mL) | 0.31 ± 0.05* | 1.87 ± 0.16 | 0.57 ± 0.21* | 0.41 ± 0.12* | 0.34 ± 0.08* |
| Neutrophil Number in BALF (×10$^6$/mL) | 0.32 ± 0.13* | 0.59 ± 0.16 | 0.40 ± 0.13* | 0.35 ± 0.14* | 0.28 ± 0.13* |
| Mononuclear cell numbers in BALF (×10$^6$/mL) | 0.29 ± 0.07* | 1.10 ± 0.21 | 0.59 ± 0.27 | 0.42 ± 0.18* | 0.34 ± 0.10* |

*$P < 0.001$, significant difference compared with vehicle animals.

IL-5 in lung homogenates of animals were determined following the same protocol as described in Example 16. The results are shown in Table 2.3.

TABLE 2.3

| | IL-5 in lung homogenates of animals | | | | |
|---|---|---|---|---|---|
| | Naïve | Vehicle | Low dose | Middle dose | High dose |
| IL-5(pg/mg of tissue) | 0.38 ± 0.15* | 1.09 ± 0.12 | 0.62 ± 0.14* | 0.45 ± 0.11* | 0.39 ± 0.07* |

*$P < 0.001$, significant difference compared with vehicle animals.

The results of this study show that the test drug combinations had strong anti-inflammatory and anti-asthma activities.

Example 18. Animal Test of Drug Combinations Disclosed Herein

Experiments similar to those described in Example 16 were performed. 48 female, BALB/c mice between 4 and 6 weeks of age were prepared and grouped as described in Example 16. Groups 1 and 2 were treated the same as described in Example 16.

In group 3, each mouse was applied with a combination of 3-[[(aminocarbonyl)oxy]methyl]-7-methoxy-8-oxo-7-[(2-thienylacetyl)amino]-5-thia-1-azabicyclo[4.2.0]oct-2-ene-2-carboxylic acid 4-piperidinemethyl ester hydrochloride (10 mg/kg, 2% solution in 25% ethanol/water), 3-piperidinemethyl acetylsalicylate hydrochloride (10 mg/kg, 2% solution in 25% ethanol/water), diethylaminoethyl [R-(E)]-1-[[[1-[3-[2-(7-chloro-2-quinolinyl)ethenyl]phenyl]-3-[2-(1-hydroxy-1-methylethyl)phenyl]propyl]thio]methyl]cyclopropaneacetate hydrochloride (1 mg/kg, 2% solution in 25% ethanol/water), (RS)-5-[2-(tert-butylamino)-1-acetyloxyethyl]benzene-1,3-diol diacetate hydrochloride (0.6 mg/kg, 0.2% solution in 25% ethanol/water), and clemastine [(2R)-2-{2-[(1R)-1-(4-chlorophenyl)-1-phenylethoxy]ethyl}-1-methylpyrrolidine (1 mg/kg, 0.3% solution in 25% ethanol/water) to the shaved skin on the neck once per day from day 14 to day 22.

in group 4, each mouse was applied with a combination of 3-[[(aminocarbonyl)oxy]methyl]-7-methoxy-8-oxo-7-[(2-thienylacetyl)amino]-5-thia-1-azabicyclo[4.2.0]oct-2-ene-2-carboxylic acid 4-piperidinemethyl ester hydrochloride (20 mg/kg, 4% solution in 25% ethanol/water), 3-piperidinemethyl acetylsalicylate hydrochloride (20 mg/kg, 4% solution in 25% ethanol/water), diethylaminoethyl [R-(E)]-1-[[[1-[3-[2-(7-chloro-2-quinolinyl)ethenyl]phenyl]-3-[2-(1-hydroxy-1-methylethyl)phenyl]propyl]thio]methyl]cyclopropaneacetate hydrochloride (2 mg/kg, 2% solution in 25% ethanol/water), (RS)-5-[2-(tert-butylamino)-1-acetyloxyethyl]benzene-1,3-diol diacetate hydrochloride (1.2 mg/kg, 0.4% solution in 25% ethanol/water), and clemastine [(2R)-2-{2-[(1R)-1-(4-chlorophenyl)-1-phenylethoxy]ethyl}-1-methylpyrrolidine (2 mg/kg, 0.6% solution in 25% ethanol/water) to the shaved skin on the neck once per day from day 15 to 22.

In group 5, each mouse was applied with a combination of 3-[[(aminocarbonyl)oxy]methyl]-7-methoxy-8-oxo-7-[(2-thienylacetyl)amino]-5-thia-1-azabicyclo[4.2.0]oct-2-ene-2-carboxylic acid 4-piperidinemethyl ester hydrochloride (30 mg/kg, 6% solution in 25% ethanol/water), 3-piperidinemethyl acetylsalicylate hydrochloride (30 mg/kg, 6% solution in 25% ethanol/water), diethylaminoethyl [R-(E)]-1-[[[1-[3-[2-(7-chloro-2-quinolinyl)ethenyl]phenyl]-3-[2-(1-hydroxy-1-methylethyl)phenyl]propyl]thio]methyl]cyclopropaneacetate hydrochloride (3 mg/kg, 2% solution in 25% ethanol/water), (RS)-5-[2-(tert-butylamino)-1-acetyloxyethyl]benzene-1,3-diol diacetate hydrochloride (1.8 mg/kg, 0.6% solution in 25% ethanol/water), and clemastine [(2R)-2-{2-[(1R)-1-(4-chlorophenyl)-1-phenylethoxy]ethyl}-1-methylpyrrolidine (3 mg/kg, 0.9% solution in 25% ethanol/water) to the shaved skin on the neck once per day from day 15 to 22.

The doses of HPPs and drug applied to Groups 3, 4, and 5 are summarized in Table 3.

When applying a combination of a plurality of drugs (e.g. one or more HPPs and/or other drug(s)) to a subject, each drug could be applied separately, or one or more of the drugs could be applied at the same time as separate drugs (e.g. spraying two or more drugs at substantially the same time without mixing the drugs before spraying), or one or more drugs could be mixed together before applying to the subject, or any combination of the above application methods. The drugs could be applied in any order possible.

TABLE 3

Doses of HPPs/Drugs applied to Groups 3, 4, and 5

| HPP | Parent drug | Drug Dose (mg/kg) Group No. 3 | Dose (mg/kg) 4 | Dose (mg/kg) 5 |
|---|---|---|---|---|
| 3-[[(aminocarbonyl)oxy]methyl]-7-methoxy-8-oxo-7-[(2-thienylacetyl)amino]-5-thia-1-azabicyclo[4.2.0]oct-2-ene-2-carboxylic acid 4-piperidinemethyl ester hydrochloride | Cefoxitin | 10 | 20 | 30 |
| 1-piperidineethyl acetylsalicylate hydrochloride | Aspirin | 10 | 20 | 30 |
| 2-(diethylamino)ethyl [R-(E)]-1-[[[1-[3-[2-(7-chloro-2-quinolinyl)ethenyl]phenyl]-3-[2-(1-hydroxy-1-methylethyl)phenyl]propyl]thio]methyl]cyclopropaneacetate hydrochloride | Montelukast | 1 | 2 | 3 |
| (RS)-5-[2-(tert-butylamino)-1-acetyloxyethyl]benzene-1,3-diol diacetate hydrochloride | Terbutaline | 0.6 | 1.2 | 1.8 |
| Clemastine | N/A | 1 | 2 | 3 |

Airway responsiveness [transpulmonary resistance ($R_L$) and dynamic compliance ($C_{dyn}$)] to inhaled β-methacholine were determined following the same protocol as described in Example 16. The results are shown in table 3.1.

TABLE 3.1

Airway Hyperresponsiveness

| | Naïve | Vehicle | Low dose | Middle dose | High dose |
|---|---|---|---|---|---|
| Transpulmonary resistance (percent of saline control at 25 mg/ml methacholine) | 159 ± 21* | 322 ± 60 | 194 ± 18* | 157 ± 18* | 141 ± 19* |
| Dynamic compliance (percent of saline control at 25 mg/ml methacholine) | −34.5 ± 3.1* | −64.1 ± 3.9 | −46.9 ± 2.1* | −39.8 ± 2.6* | −35.3 ± 2.6* |

*P < 0.001, significant difference compared with vehicle-treated animals

Eosinophil numbers, neutrophil number and mononuclear cell numbers in BALF were determined following the same protocol as described in Example 16. The results are shown in Table 3.2.

TABLE 3.2

Eosinophil numbers, neutrophil number and mononuclear cell numbers in BALF

|  | Naïve | Vehicle | Low dose | Middle dose | High dose |
|---|---|---|---|---|---|
| Eosinophil Numbers in Blood ($\times 10^6$/mL) | 0.031 ± 0.011* | 0.572 ± 0.121 | 0.192 ± 0.023 | 0.095 ± 0.021* | 0.047 ± 0.015* |
| Neutrophil Number in Blood ($\times 10^6$/mL) | 0.57 ± 0.16* | 1.17 ± 0.15 | 0.69 ± 0.21* | 0.57 ± 0.14* | 0.53 ± 0.12* |
| Mononuclear cell numbers in Blood ($\times 10^6$/mL) | 2.09 ± 0.19 | 5.17 ± 0.21 | 2.73 ± 0.36 | 1.79 ± 0.23* | 1.65 ± 0.20* |
| Eosinophil Numbers in BALF ($\times 10^6$/mL) | 0.30 ± 0.07* | 1.80 ± 0.15 | 0.59 ± 0.18* | 0.45 ± 0.10* | 0.37 ± 0.10* |
| Neutrophil Number in BALF ($\times 10^6$/mL) | 0.36 ± 0.11* | 0.61 ± 0.09 | 0.45 ± 0.21 | 0.39 ± 0.10* | 0.34 ± 0.10* |
| Mononuclear cell numbers in BALF ($\times 10^6$/mL) | 0.33 ± 0.09* | 1.15 ± 0.23 | 0.61 ± 0.29 | 0.47 ± 0.21* | 0.32 ± 0.15* |

*$P < 0.001$, significant difference compared with vehicle animals.

IL-5 in lung homogenates of animals were determined following the same protocol as described in Example 16. The results are shown in Table 3.3.

TABLE 3.3

IL-5 in lung homogenates of animals

|  | Naïve | Vehicle | Low dose | Middle dose | High dose |
|---|---|---|---|---|---|
| IL-5(pg/mg of tissue) | 0.33 ± 0.11* | 1.13 ± 0.15 | 0.58 ± 0.17* | 0.41 ± 0.16* | 0.36 ± 0.09* |

*$P < 0.001$, significant difference compared with vehicle animals.

The results of this study show that the test drug combinations had strong anti-inflammatory and anti-asthma activities.

Example 19. Animal Test of Drug Combinations Disclosed Herein

Experiments similar to those described in Example 16 were performed. 48 female, BALB/c mice between 4 and 6 weeks of age were prepared and grouped as described in Example 16. Groups 1 and 2 were treated the same as described in Example 16.

In group 3, each mouse was applied with a combination of 3-[[(aminocarbonyl)oxy]methyl]-7-methoxy-8-oxo-7-[(2-thienylacetyl)amino]-5-thia-1-azabicyclo[4.2.0]oct-2-ene-2-carboxylic acid 4-piperidinemethyl ester hydrochloride (10 mg/kg, 2% solution in 25% ethanol/water), 3-piperidinemethyl 2-(p-isobutylphenyl) propionate hydrochloride (5 mg/kg, 1% solution in 25% ethanol/water), 2-pyrrolidinemethyl 2-[1-[[(1R)-1-[3-[2-(7-chloroquinolin-2-yl)ethenyl]phenyl]-3-[2-(2-hydroxypropan-2-yl)phenyl]propyl]sulfanylmethyl]cyclopropyl]acetate hydrochloride (1 mg/kg, 0.3% solution in 25% ethanol/water), (RS)-5-[2-(tert-butylamino)-1-acetyloxyethyl]benzene-1,3-diol diacetate hydrochloride (0.6 mg/kg, 0.2% solution in 25% ethanol/water), and clemastine (1 mg/kg, 0.3% solution in 25% ethanol/water) to the shaved skin on the neck once per day from day 14 to day 22.

In group 4, each mouse was applied with a combination of 3-[[(aminocarbonyl)oxy]methyl]-7-methoxy-8-oxo-7-[(2-thienylacetyl)amino]-5-thia-1-azabicyclo[4.2.0]oct-2-ene-2-carboxylic acid 4-piperidinemethyl ester hydrochloride (20 mg/kg, 4% solution in 25% ethanol/water), 3-piperidinemethyl 2-(p-isobutylphenyl) propionate hydrochloride (10 mg/kg, 2% solution in 25% ethanol/water), 2-pyrrolidinemethyl 2-[1-[[(1R)-1-[3-[2-(7-chloroquinolin-2-yl)ethenyl]phenyl]-3-[2-(2-hydroxypropan-2-yl)phenyl]propyl]sulfanylmethyl]cyclopropyl]acetate hydrochloride (2 mg/kg, 0.6% solution in 25% ethanol/water), (RS)-5-[2-(tert-butylamino)-1-acetyloxyethyl]benzene-1,3-diol diacetate hydrochloride (1.2 mg/kg, 0.4% solution in 25% ethanol/water), and clemastine (2 mg/kg, 0.6% solution in 25% ethanol/water) to the shaved skin on the neck once per day from day 15 to 22.

In group 5, each mouse was applied with a combination of 3-[[(aminocarbonyl)oxy]methyl]-7-methoxy-8-oxo-7-[(2-thienylacetyl)amino]-5-thia-1-azabicyclo[4.2.0]oct-2-ene-2-carboxylic acid 4-piperidinemethyl ester hydrochloride (30 mg/kg, 6% solution in 25% ethanol/water), 3-piperidinemethyl 2-(p-isobutylphenyl) propionate hydrochloride (15 mg/kg, 3% solution in 25% ethanol/water), 2-pyrrolidinemethyl 2-[1-[[(1R)-1-[3-[2-(7-chloroquinolin-2-yl)ethenyl]phenyl]-3-[2-(2-hydroxypropan-2-yl)phenyl]propyl]sulfanylmethyl]cyclopropyl]acetate hydrochloride (3 mg/kg, 0.9% solution in 25% ethanol/water), (RS)-5-[2-(tert-butylamino)-1-acetyloxyethyl]benzene-1,3-diol diacetate hydrochloride (1.8 mg/kg, 0.6% solution in 25% ethanol/water), and clemastine (3 mg/kg, 0.9% solution in 25% ethanol/water) to the shaved skin on the neck once per day from day 15 to 22.

The doses of HPPs and drug applied to Groups 3, 4, and 5 are summarized in Table 4.

When applying a combination of a plurality of drugs (e.g. one or more HPPs and/or other drug(s)) to a subject, each drug could be applied separately, or one or more of the drugs could be applied at the same time as separate drugs (e.g. spraying two or more drugs at substantially the same time without mixing the drugs before spraying), or one or more drugs could be mixed together before applying to the subject, or any combination of the above application methods. The drugs could be applied in any order possible.

TABLE 4

Doses of HPPs/Drugs applied to Groups 3, 4, and 5

| HPP | Parent drug | Drug Dose (mg/kg) Group No. 3 | Dose (mg/kg) Group No. 4 | Dose (mg/kg) Group No. 5 |
|---|---|---|---|---|
| 3-[[(Aminocarbonyl)oxy]methyl]-7-methoxy-8-oxo-7-[(2-thienylacetyl)amino]-5-thia-1-azabicyclo[4.2.0]oct-2-ene-2-carboxylic acid 4-piperidinemethyl ester hydrochloride | Cefoxitin | 10 | 20 | 30 |
| 3-Piperidinemethyl 2-(ρ-isobutylphenyl) propionate hydrochloride | Ibuprofen | 5 | 10 | 15 |
| 2-Pyrrolidinemethyl 2-[1-[[(1R)-1-[3-[2-(7-chloroquinolin-2-yl)ethenyl]phenyl]-3-[2-(2-hydroxypropan-2-yl)phenyl]propyl]sulfanylmethyl]cyclopropyl]acetate hydrochloride | Montelukast | 1 | 2 | 3 |
| (RS)-5-[2-(Tert-butylamino)-1-acetyloxyethyl]benzene-1,3-diol diacetate hydrochloride | Terbutaline | 0.6 | 1.2 | 1.8 |
| Clemastine | N/A | 1 | 2 | 3 |

Airway responsiveness [transpulmonary resistance ($R_L$) and dynamic compliance ($C_{dyn}$)] to inhaled β-methacholine were determined following the same protocol as described in Example 16. The results are shown in Table 4.1.

TABLE 4.1

| Airway Hyperresponsiveness | | | | | |
|---|---|---|---|---|---|
| | Naïve | Vehicle | Low dose | Middle dose | High dose |
| Transpulmonary resistance (percent of saline control at 25 mg/ml methacholine) | 166 ± 20* | 326 ± 52 | 196 ± 13* | 157 ± 19* | 149 ± 12* |
| Dynamic compliance (percent of saline control at 25 mg/ml methacholine) | −34.7 ± 3.3* | −63.1 ± 2.9 | −47.3 ± 2.3* | −41.2 ± 2.3* | −34.3 ± 2.7* |

*$P < 0.001$, significant difference compared with vehicle-treated animals

Eosinophil numbers, neutrophil number and mononuclear cell numbers in BALF were determined following the same protocol as described in Example 16. The results are shown in Table 4.2.

TABLE 4.2

| Eosinophil numbers, neutrophil number and mononuclear cell numbers in BALF | | | | | |
|---|---|---|---|---|---|
| | Naïve | Vehicle | Low dose | Middle dose | High dose |
| Eosinophil Numbers in Blood (×10$^6$/mL) | 0.033 ± 0.014* | 0.590 ± 0.131 | 0.197 ± 0.023 | 0.097 ± 0.022* | 0.041 ± 0.013* |
| Neutrophil Number in Blood (×10$^6$/mL) | 0.58 ± 0.14* | 1.15 ± 0.17 | 0.71 ± 0.18* | 0.58 ± 0.15* | 0.51 ± 0.14* |

TABLE 4.2-continued

Eosinophil numbers, neutrophil number and mononuclear cell numbers in BALF

|  | Naïve | Vehicle | Low dose | Middle dose | High dose |
|---|---|---|---|---|---|
| Mononuclear cell numbers in Blood ($\times 10^6$/mL) | 2.25 ± 0.17 | 5.17 ± 0.23 | 2.75 ± 0.38 | 1.82 ± 0.21* | 1.60 ± 0.23* |
| Eosinophil Numbers in BALF ($\times 10^6$/mL) | 0.31 ± 0.08* | 1.80 ± 0.14 | 0.56 ± 0.16* | 0.47 ± 0.12* | 0.39 ± 0.11* |
| Neutrophil Number in BALF ($\times 10^6$/mL) | 0.38 ± 0.10* | 0.62 ± 0.08 | 0.48 ± 0.28 | 0.41 ± 0.09* | 0.38 ± 0.12* |
| Mononuclear cell numbers in BALF ($\times 10^6$/mL) | 0.31 ± 0.06* | 1.09 ± 0.22 | 0.67 ± 0.32 | 0.45 ± 0.20* | 0.33 ± 0.12* |

*$P < 0.001$, significant difference compared with vehicle animals.

IL-5 in lung homogenates of animals were determined following the same protocol as described in Example 16. The results are shown in Table 4.3.

TABLE 4.3

IL-5 in lung homogenates of animals

|  | Naïve | Vehicle | Low dose | Middle dose | High dose |
|---|---|---|---|---|---|
| IL-5(pg/mg of tissue) | 0.31 ± 0.13* | 1.15 ± 0.19 | 0.59 ± 0.18* | 0.43 ± 0.15* | 0.37 ± 0.08* |

*$P < 0.001$, significant difference compared with vehicle animals.

The results of this study show that the test drug combinations had strong anti-inflammatory and anti-asthma activities.

Example 20. Animal Test of Drug Combinations Disclosed Herein

Experiments similar to those described in Example 16 were performed. 48 female, BALB/c mice between 4 and 6 weeks of age were prepared and grouped as described in Example 16. Groups 1 and 2 were treated the same as described in Example 16.

In group 3, each mouse was applied with a combination of 2-pyrrolidinemethyl 2-[(2,6-dichlorophenyl)amino]benzene acetate hydrochloride (3 mg/kg, 1% solution in 25% ethanol/water), diethylaminoethyl 2-[1-[[(1R)-1-[3-[2-(7-chloroquinolin-2-yl)ethenyl]phenyl]-3-[2-(2-hydroxypropan-2-yl)phenyl]propyl]sulfanylmethyl]cyclopropyl]acetate (HPP of montelukast, 1 mg/kg, 0.3% solution in 25% ethanol/water), (R,S)α$^6$-{[(1,1-dimethylethyl)amino]methyl}-3-acetyloxy-2,6-pyridinedimethanol diacetate hydrochloride (0.2 mg/kg, 0.1% solution in 25% ethanol/water) and diphenhydramine (3 mg/kg, 1% solution in 25% ethanol/water) to the shaved skin on the neck once per day from day 14 to day 22.

In group 4, each mouse was applied with a combination of 2-pyrrolidinemethyl 2-[(2,6-dichlorophenyl)amino]benzene acetate hydrochloride (6 mg/kg, 2% solution in 25% ethanol/water), diethylaminoethyl 2-[1-[[(1R)-1-[3-[2-(7-chloroquinolin-2-yl)ethenyl]phenyl]-3-[2-(2-hydroxypropan-2-yl)phenyl]propyl]sulfanylmethyl]cyclopropyl]acetate (2 mg/kg, 0.6% solution in 25% ethanol/water), (R,S)α$^6$-{[(1,1-dimethylethyl)amino]methyl}-3-acetyloxy-2,6-pyridinedimethanol diacetate hydrochloride (0.4 mg/kg, 0.2% solution in 25% ethanol/water) and diphenhydramine (6 mg/kg, 2% solution in 25% ethanol/water) to the shaved skin on the neck once per day from day 15 to 22.

In group 5, each mouse was applied with a combination of 2-pyrrolidinemethyl 2-[(2,6-dichlorophenyl)amino]benzene acetate hydrochloride (9 mg/kg, 3% solution in 25% ethanol/water), diethylaminoethyl 2-[1-[[(1R)-1-[3-[2-(7-chloroquinolin-2-yl)ethenyl]phenyl]-3-[2-(2-hydroxypropan-2-yl)phenyl]propyl]sulfanylmethyl]cyclopropyl]acetate (3 mg/kg, 0.9% solution in 25% ethanol/water), (R,S)α$^6$-{[(1,1-dimethylethyl)amino]methyl}-3-acetyloxy-2,6-pyridinedimethanol diacetate hydrochloride (0.5 mg/kg, 0.3% solution in 25% ethanol/water) and diphenhydramine (9 mg/kg, 3% solution in 25% ethanol/water) to the shaved skin on the neck once per day from day 15 to 22.

The doses of HPPs and drug applied to Groups 3, 4, and 5 are summarized in Table 5.

When applying a combination of a plurality of drugs (e.g. one or more HPPs and/or other drug(s)) to a subject, each drug could be applied separately, or one or more of the drugs could be applied at the same time as separate drugs (e.g. spraying two or more drugs at substantially the same time without mixing the drugs before spraying), or one or more drugs could be mixed together before applying to the subject, or any combination of the above application methods. The drugs could be applied in any order possible.

TABLE 5

Doses of HPPs/Drugs applied to Groups 3, 4, and 5

| HPP | Parent drug | Drug Dose (mg/kg) Group No. 3 | Dose (mg/kg) 4 | Dose (mg/kg) 5 |
|---|---|---|---|---|
| 2-pyrrolidinemethyl 2-[(2,6-dichlorophenyl)amino]benzene acetate hydrochloride | Diclofenac | 3 | 6 | 9 |
| diethylaminoethyl 2-[1-[[(1R)-1-[3-[2-(7-chloroquinolin-2-yl)ethenyl]phenyl]-3-[2-(2-hydroxypropan-2-yl)phenyl]propyl]sulfanylmethyl]cyclopropyl]acetate | Montelukast | 1 | 2 | 3 |
| (R,S)α$^6$-{[(1,1-dimethylethyl) amino]methyl}-3-acetyloxy-2,6-pyridinedimethanol diacetate hydrochloride | Pirbuterol | 0.2 | 0.4 | 0.5 |
| Diphenhydramine | N/A | 3 | 6 | 9 |

Airway responsiveness [transpulmonary resistance ($R_L$) and dynamic compliance ($C_{dyn}$)] to inhaled β-methacholine were determined following the same protocol as described in Example 16. The results are shown in Table 5.1.

TABLE 5.1

Airway Hyperresponsiveness

| | Naïve | Vehicle | Low dose | Middle dose | High dose |
|---|---|---|---|---|---|
| Transpulmonary resistance (percent of saline control at 25 mg/ml methacholine) | 161 ± 18* | 331 ± 46 | 211 ± 19 | 168 ± 18* | 157 ± 15* |
| Dynamic compliance (percent of saline control at 25 mg/ml methacholine) | −34.2 ± 3.0* | −62.1 ± 2.7 | −47.6 ± 2.1* | −45.2 ± 2.0* | −37.3 ± 2.1* |

*$P < 0.001$, significant difference compared with vehicle-treated animals

Eosinophil numbers, neutrophil number and mononuclear cell numbers in BALF were determined following the same protocol as described in Example 16. The results were shown in Table 5.2.

TABLE 5.2

Eosinophil numbers, neutrophil number and mononuclear cell numbers in BALF

| | Naïve | Vehicle | Low dose | Middle dose | High dose |
|---|---|---|---|---|---|
| Eosinophil Numbers in Blood (×10$^6$/mL) | 0.039 ± 0.015* | 0.599 ± 0.115 | 0.190 ± 0.025 | 0.098 ± 0.021* | 0.045 ± 0.015* |
| Neutrophil Number in Blood (×10$^6$/mL) | 0.57 ± 0.15* | 1.18 ± 0.22 | 0.76 ± 0.17* | 0.62 ± 0.14* | 0.57 ± 0.18* |
| Mononuclear cell numbers in Blood (×10$^6$/mL) | 2.01 ± 0.18 | 5.07 ± 0.26 | 2.78 ± 0.42 | 1.86 ± 0.20* | 1.69 ± 0.26* |
| Eosinophil Numbers in BALF (×10$^6$/mL) | 0.30 ± 0.11* | 1.82 ± 0.17 | 0.58 ± 0.19* | 0.49 ± 0.17* | 0.42 ± 0.15* |
| Neutrophil Number in BALF (×10$^6$/mL) | 0.36 ± 0.13* | 0.69 ± 0.12 | 0.51 ± 0.29 | 0.44 ± 0.07* | 0.39 ± 0.13* |
| Mononuclear cell numbers in BALF (×10$^6$/mL) | 0.30 ± 0.08* | 1.07 ± 0.25 | 0.69 ± 0.31 | 0.48 ± 0.22* | 0.41 ± 0.14* |

*$P < 0.001$, significant difference compared with vehicle animals.

IL-5 in lung homogenates of animals were determined following the same protocol as described in Example 16. The results are shown in Table 5.3.

TABLE 5.3

IL-5 in lung homogenates of animals

| | Naïve | Vehicle | Low dose | Middle dose | High dose |
|---|---|---|---|---|---|
| IL-5(pg/mg of tissue) | 0.31 ± 0.13* | 1.15 ± 0.19 | 0.59 ± 0.18* | 0.43 ± 0.15* | 0.37 ± 0.08* |

*$P < 0.001$, significant difference compared with vehicle animals.

The results of this study show that the test drug combinations had strong anti-inflammatory and anti-asthma activities.

Example 21. Animal Test of Drug Combinations Disclosed Herein

Experiments similar to those described in Example 16 were performed. 48 female, BALB/c mice between 4 and 6 weeks of age were prepared and grouped as described in Example 16. Groups 1 and 2 were treated the same as described in Example 16.

In group 3, each mouse was applied with a combination of diethylaminoethyl 5-(2,4-difluorophenyl)salicylate hydrochloride (7 mg/kg, 1.5% solution in 25% ethanol/water), (RS)—N-[1-(1-benzothien-2-yl)ethyl]-N-(2-diethylaminoacetyloxyl)urea hydrochloride, (10 mg/kg, 2% solution in 25% ethanol/water), (±)-α-[(tert-butylamino)methyl]-3,5-diacetyloxybenzyl alcohol acetate hydrochloride (0.07 mg/kg, 0.05% solution in 25% ethanol/water), and doxylamine [(RS)—N,N-dimethyl-2-(1-phenyl-1-pyridine-2-yl-ethoxy)-ethanamine](3 mg/kg, 0.6% solution in 25% ethanol/water) to the shaved skin on the neck once per day from day 14 to day 22.

In group 4, each mouse was applied with a combination of diethylaminoethyl 5-(2,4-difluorophenyl)salicylate hydrochloride (14 mg/kg, 3% solution in 25% ethanol/water), (RS)—N-[1-(1-benzothien-2-yl)ethyl]-N-(2-diethylaminoacetyloxyl)urea hydrochloride, (20 mg/kg, 4% solution in 25% ethanol/water), (±)-α-[(tert-butylamino)methyl]-3,5-diacetyloxybenzyl alcohol acetate hydrochloride (0.14 mg/kg, 0.1% solution in 25% ethanol/water), and doxylamine (6 mg/kg, 1.2% solution in 25% ethanol/water) to the shaved skin on the neck once per day from day 15 to 22.

In group 5, each mouse was applied with a combination of diethylaminoethyl 5-(2,4-difluorophenyl)salicylate hydrochloride (20 mg/kg, 4.5% solution in 25% ethanol/water), (RS)—N-[1-(1-benzothien-2-yl)ethyl]-N-(2-diethylaminoacetyloxyl)urea hydrochloride, (30 mg/kg, 6% solution in 25% ethanol/water), (±)-α-[(tert-butylamino)methyl]-3,5-diacetyloxybenzyl alcohol acetate hydrochloride (0.2 mg/kg, 0.15% solution in 25% ethanol/water), and doxylamine (9 mg/kg, 2% solution in 25% ethanol/water) to the shaved skin on the neck once per day from day 15 to 22.

The doses of HPPs and drug applied to Groups 3, 4, and 5 are summarized in Table 6.

When applying a combination of a plurality of drugs (e.g. one or more HPPs and/or other drug(s)) to a subject, each drug could be applied separately, or one or more of the drugs could be applied at the same time as separate drugs (e.g. spraying two or more drugs at substantially the same time without mixing the drugs before spraying), or one or more drugs could be mixed together before applying to the subject, or any combination of the above application methods. The drugs could be applied in any order possible.

TABLE 6

Doses of HPPs/Drugs applied to Groups 3, 4, and 5

| | | Drug | | |
|---|---|---|---|---|
| | | Dose (mg/kg) | Dose (mg/kg) | Dose (mg/kg) |
| | | Group No. | | |
| HPP | Parent drug | 3 | 4 | 5 |
| Diethylaminoethyl 5-(2,4-difluorophenyl)salicylate hydrochloride | Diflunisal | 7 | 14 | 20 |
| (RS)-N-[1-(1-Benzothien-2-yl)ethyl]-N-(2-diethylaminoacetyloxy)urea hydrochloride | Zileuton | 10 | 20 | 30 |
| (±)-α-[(Tert-butylamino)methyl]-3,5-diacetyloxybenzyl alcohol acetate hydrochloride | Terbutaline | 0.04 | 0.14 | 0.2 |
| Doxylamine | N/A | 3 | 6 | 9 |

Airway responsiveness [transpulmonary resistance ($R_L$) and dynamic compliance ($C_{dyn}$)] to inhaled β-methacholine were determined following the same protocol as described in Example 16. The results are shown in Table 6.1.

TABLE 6.1

Airway Hyperresponsiveness

| | Naïve | Vehicle | Low dose | Middle dose | High dose |
|---|---|---|---|---|---|
| Transpulmonary resistance (percent of saline control at 25 mg/ml methacholine) | 149 ± 20* | 320 ± 57 | 198 ± 25 | 162 ± 17* | 155 ± 22* |
| Dynamic compliance (percent of saline control at 25 mg/ml methacholine) | −34.1 ± 2.8* | −64.5 ± 3.2 | −48.9 ± 3.5 | −41.8 ± 2.0* | −37.9 ± 3.6* |

*$P < 0.001$, significant difference compared with vehicle-treated animals

Eosinophil numbers, neutrophil number and mononuclear cell numbers in BALF were determined following the same protocol as described in Example 16. The results were shown in Table 6.2.

TABLE 6.2

Eosinophil numbers, neutrophil number and mononuclear cell numbers in BALF

|  | Naïve | Vehicle | Low dose | Middle dose | High dose |
|---|---|---|---|---|---|
| Eosinophil Numbers in Blood ($\times 10^6$/mL) | 0.041 ± 0.010* | 0.592 ± 0.134 | 0.232 ± 0.028 | 0.097 ± 0.025* | 0.056 ± 0.019* |
| Neutrophil Number in Blood ($\times 10^6$/mL) | 0.58 ± 0.18* | 1.19 ± 0.18 | 0.75 ± 0.30 | 0.56 ± 0.15* | 0.54 ± 0.17* |
| Mononuclear cell numbers in Blood ($\times 10^6$/mL) | 2.01 ± 0.17* | 5.19 ± 0.25 | 2.69 ± 0.39 | 1.84 ± 0.20* | 1.61 ± 0.25* |
| Eosinophil Numbers in BALF ($\times 10^6$/mL) | 0.33 ± 0.08* | 1.83 ± 0.17 | 0.58 ± 0.20* | 0.49 ± 0.12* | 0.39 ± 0.15* |
| Neutrophil Number in BALF ($\times 10^6$/mL) | 0.35 ± 0.14* | 0.62 ± 0.12 | 0.47 ± 0.26 | 0.42 ± 0.12* | 0.38 ± 0.15* |
| Mononuclear cell numbers in BALF ($\times 10^6$/mL) | 0.32 ± 0.08* | 1.17 ± 0.27 | 0.72 ± 0.33 | 0.58 ± 0.15* | 0.37 ± 0.18* |

*$P < 0.001$, significant difference compared with vehicle animals.

IL-5 in lung homogenates of animals were determined following the same protocol as described in Example 16. The results are shown in Table 6.3.

TABLE 6.3

IL-5 in lung homogenates of animals

|  | Naïve | Vehicle | Low dose | Middle dose | High dose |
|---|---|---|---|---|---|
| IL-5(pg/mg of tissue) | 0.37 ± 0.13* | 1.16 ± 0.25 | 0.68 ± 0.19* | 0.48 ± 0.22* | 0.41 ± 0.11* |

*$P < 0.001$, significant difference compared with vehicle animals.

The results of this study show that the test Combinations have strong anti-inflammatory and anti-asthma activities.

Example 22. Animal Test of Drug Combinations Disclosed Herein

Experiments similar to those described in Example 16 were performed. 48 female, BALB/c mice between 4 and 6 weeks of age were prepared and grouped as described in Example 16. Groups 1 and 2 were treated the same as described in Example 16.

In group 3, each mouse was applied with a combination of D-α-[(imidazolidin-2-on-1-yl)carbonylamino]benzyl-penicillin 2-pyrrolidinemethyl ester hydrochloride (10 mg/kg, 2% solution in 25% ethanol/water), diethylaminoethyl 5-(2,4-difluorophenyl)salicylate hydrochloride (10 mg/kg, 2% solution in 25% ethanol/water), diethylaminoethyl [R-(E)]-1-[[[1-[3-[2-(7-chloro-2-quinolinyl)ethenyl]phenyl]-3-[2-(1-hydroxy-1-methylethyl)phenyl]propyl]thio]methyl]cyclopropaneacetate hydrochloride (1 mg/kg, 0.3% solution in 25% ethanol/water), and ephedrine (3 mg/kg, 1% solution in 25% ethanol/water) to the shaved skin on the neck once per day from day 14 to day 22.

In group 4, each mouse was applied with a combination of D-α-[(imidazolidin-2-on-1-yl)carbonylamino]benzyl-penicillin 2-pyrrolidinemethyl ester hydrochloride (20 mg/kg, 4% solution in 25% ethanol/water), diethylaminoethyl 5-(2,4-difluorophenyl)salicylate hydrochloride (20 mg/kg, 4% solution in 25% ethanol/water), diethylaminoethyl [R-(E)]-1-[[[1-[3-[2-(7-chloro-2-quinolinyl)ethenyl]phenyl]-3-[2-(1-hydroxy-1-methylethyl)phenyl]propyl]thio]methyl]cyclopropaneacetate hydrochloride (2 mg/kg, 0.6% solution in 25% ethanol/water), and ephedrine (6 mg/kg, 2% solution in 25% ethanol/water) to the shaved skin on the neck of mice once per day from day 15 to 22.

In group 5, each mouse was applied with a combination of D-α-[(imidazolidin-2-on-1-yl)carbonylamino]benzyl-penicillin 2-pyrrolidinemethyl ester hydrochloride (30 mg/kg, 6% solution in 25% ethanol/water), diethylaminoethyl 5-(2,4-difluorophenyl)salicylate hydrochloride (30 mg/kg, 6% solution in 25% ethanol/water), diethylaminoethyl [R-(E)]-1-[[[1-[3-[2-(7-chloro-2-quinolinyl)ethenyl]phenyl]-3-[2-(1-hydroxy-1-methylethyl)phenyl]propyl]thio]methyl]cyclopropaneacetate hydrochloride (3 mg/kg, 0.9% solution in 25% ethanol/water), and ephedrine (9 mg/kg, 3% solution in 25% ethanol/water) to the shaved skin on the neck once per day from day 15 to 22.

The doses of HPPs and drug applied to Groups 3, 4, and 5 are summarized in Table 7.

When applying a combination of a plurality of drugs (e.g. one or more HPPs and/or other drug(s)) to a subject, each drug could be applied separately, or one or more of the drugs could be applied at the same time as separate drugs (e.g. spraying two or more drugs at substantially the same time without mixing the drugs before spraying), or one or more drugs could be mixed together before applying to the subject, or any combination of the above application methods. The drugs could be applied in any order possible.

TABLE 7

Doses of HPPs/Drugs applied to Groups 3, 4, and 5

| HPP | Parent drug | Drug Dose (mg/kg) Group No. 3 | Dose (mg/kg) 4 | Dose (mg/kg) 5 |
|---|---|---|---|---|
| D-α-[(Imidazolidin-2-on-1-yl)carbonylamino]benzylpenicillin 2-pyrrolidinemethyl ester hydrochloride | Penicillin V | 10 | 20 | 30 |
| Diethylaminoethyl 5-(2,4-difluorophenyl)salicylate hydrochloride | Diflunisal | 10 | 20 | 30 |
| Diethylaminoethyl [R-(E)]-1-[[[1-[3-[2-(7-chloro-2-quinolinyl)ethenyl]phenyl]-3-[2-(1-hydroxy-1-methylethyl)phenyl]propyl]thio]methyl]cyclopropaneacetate hydrochloride | Montelukast | 1 | 2 | 3 |
| Ephedrine | N/A | 3 | 6 | 9 |

Airway responsiveness [transpulmonary resistance ($R_L$) and dynamic compliance ($C_{dyn}$)] to inhaled β-methacholine were determined following the same protocol as described in Example 16. The results are shown in Table 7.1.

TABLE 7.1

Airway Hyperresponsiveness

| | Naïve | Vehicle | Low dose | Middle dose | High dose |
|---|---|---|---|---|---|
| Transpulmonary resistance (percent of saline control at 25 mg/ml methacholine) | 149 ± 21* | 307 ± 65 | 195 ± 17* | 162 ± 23* | 152 ± 18* |
| Dynamic compliance (percent of saline control at 25 mg/ml methacholine) | −31.1 ± 3.1* | −62.5 ± 3.5 | −48.2 ± 3.1* | −43.0 ± 2.5* | −34.9 ± 3.0* |

*P < 0.001, significant difference compared with vehicle-treated animals

Eosinophil numbers, neutrophil number and mononuclear cell numbers in BALF were determined following the same protocol as described in Example 16. The results are shown in Table 7.2.

TABLE 7.2

Eosinophil numbers, neutrophil number and mononuclear cell numbers in BALF

| | Naïve | Vehicle | Low dose | Middle dose | High dose |
|---|---|---|---|---|---|
| Eosinophil Numbers in Blood (×10$^6$/mL) | 0.041 ± 0.011* | 0.592 ± 0.132 | 0.189 ± 0.048 | 0.099 ± 0.017* | 0.046 ± 0.018* |
| Neutrophil Number in Blood (×10$^6$/mL) | 0.50 ± 0.15* | 1.17 ± 0.18 | 0.72 ± 0.15* | 0.65 ± 0.13* | 0.49 ± 0.19* |
| Mononuclear cell numbers in Blood (×10$^6$/mL) | 2.80 ± 0.16* | 5.21 ± 0.18 | 2.61 ± 0.48 | 1.56 ± 0.25* | 1.30 ± 0.29* |
| Eosinophil Numbers in BALF (×10$^6$/mL) | 0.34 ± 0.06* | 1.86 ± 0.18 | 0.69 ± 0.18* | 0.48 ± 0.15* | 0.39 ± 0.18* |
| Neutrophil Number in BALF (×10$^6$/mL) | 0.30 ± 0.13* | 0.58 ± 0.17 | 0.42 ± 0.11* | 0.38 ± 0.16* | 0.36 ± 0.15* |
| Mononuclear cell numbers in BALF (×10$^6$/mL) | 0.27 ± 0.11* | 1.11 ± 0.23 | 0.67 ± 0.33 | 0.48 ± 0.17* | 0.38 ± 0.15* |

*P < 0.001, significant difference compared with vehicle animals.

IL-5 in lung homogenates of animals were determined following the same protocol as described in Example 16. The results are shown in Table 7.3.

TABLE 7.3

| | IL-5 in lung homogenates of animals | | | | |
|---|---|---|---|---|---|
| | Naïve | Vehicle | Low dose | Middle dose | High dose |
| IL-5(pg/mg of tissue) | 0.35 ± 0.13* | 1.12 ± 0.15 | 0.65 ± 0.12* | 0.48 ± 0.13* | 0.38 ± 0.12* |

*$P < 0.001$, significant difference compared with vehicle animals.

The results of this study show that the test drug combinations had strong anti-inflammatory and anti-asthma activities.

Example 23. Animal Test of Drug Combinations Disclosed Herein

Experiments similar to those described in Example 16 were performed. 48 female, BALB/c mice between 4 and 6 weeks of age were prepared and grouped as described in Example 16. Groups 1 and 2 were treated the same as described in Example 16.

In group 3, each mouse was applied with a combination of 6-D(−)-α-(4-ethyl-2,3-dioxo-1-piperazinylcarbonylamino)-α-phenylacetamidopenicillinic acid 2-diethylaminoethyl ester hydrochloride (10 mg/kg, 2% solution in 25% ethanol/water), 2-diethylaminoethyl 2[(2,6-dichlorophenyl)amino]benzene acetate hydrochloride (3 mg/kg, 0.6% solution in 25% ethanol/water), (RS)—N-[1-(1-benzothien-2-yl)ethyl]-N-(2-diethylaminoacetyloxyl)urea hydrochloride (HPP of zileuton, 10 mg/kg, 2% solution in 25% ethanol/water), (RS)-5-[1-acetyloxy-2-(isopropylamino)ethyl]benzene-1,3-diol diacetate hydrochloride (1 mg/kg, 0.2% solution in 25% ethanol/water), and levomethamphetamine (3 mg/kg, 0.6% solution in 25% ethanol/water) to the shaved skin on the neck once per day from day 14 to day 22.

In group 4, each mouse was applied with a combination of 6-D(−)-α-(4-ethyl-2,3-dioxo-1-piperazinylcarbonylamino)-α-phenylacetamidopenicillinic acid 2-diethylaminoethyl ester hydrochloride (20 mg/kg, 4% solution in 25% ethanol/water), 2-diethylaminoethyl 2[(2,6-dichlorophenyl)amino]benzene acetate hydrochloride (6 mg/kg, 1.2% solution in 25% ethanol/water), (RS)—N-[1-(1-benzothien-2-yl)ethyl]-N-(2-ethylaminoacetyloxyl)urea hydrochloride (10 mg/kg, 2% solution in 25% ethanol/water), (RS)-5-[1-acetyloxy-2-(isopropylamino)ethyl]benzene-1,3-diol diacetate hydrochloride (2 mg/kg, 0.4% solution in 25% ethanol/water), and levomethamphetamine (6 mg/kg, 1.2% solution in 25% ethanol/water) to the shaved skin on the neck once per day from day 15 to 22.

In group 5, each mouse was applied with a combination of 6-D(−)-α-(4-ethyl-2,3-dioxo-1-piperazinylcarbonylamino)-α-phenylacetamidopenicillinic acid 2-diethylaminoethyl ester hydrochloride (30 mg/kg, 6% solution in 25% ethanol/water), 2-diethylaminoethyl 2[(2,6-dichlorophenyl)amino]benzene acetate hydrochloride (9 mg/kg, 2% solution in 25% ethanol/water), (RS)—N-[1-(1-benzothien-2-yl)ethyl]-N-(2-diethylaminoacetyloxyl)urea hydrochloride (30 mg/kg, 6% solution in 25% ethanol/water), (RS)-5-[1-acetyloxy-2-(isopropylamino)ethyl]benzene-1,3-diol diacetate hydrochloride (3 mg/kg, 0.6% solution in 25% ethanol/water), and levomethamphetamine (9 mg/kg, 1.8% solution in 25% ethanol/water) (6 mg/kg, 2% solution in 25% ethanol/water) to the shaved skin on the neck once per day from day 15 to 22.

The doses of HPPs and drug applied to Groups 3, 4, and 5 are summarized in Table 8.

When applying a combination of a plurality of drugs (e.g. one or more HPPs and/or other drug(s)) to a subject, each drug could be applied separately, or one or more of the drugs could be applied at the same time as separate drugs (e.g. spraying two or more drugs at substantially the same time without mixing the drugs before spraying), or one or more drugs could be mixed together before applying to the subject, or any combination of the above application methods. The drugs could be applied in any order possible.

TABLE 8

| Doses of HPPs/Drugs applied to Groups 3, 4, and 5 | | | | |
|---|---|---|---|---|
| | | Drug | | |
| | | Dose (mg/kg) | Dose (mg/kg) | Dose (mg/kg) |
| | | | Group No. | |
| HPP | Parent drug | 3 | 4 | 5 |
| 6-D(−)-α-(4-ethyl-2,3-dioxo-1-piperazinylcarbonylamino)-α-phenylacetamidopenicillinic acid 2-diethylaminoethyl ester hydrochloride | Piperacillin | 10 | 20 | 30 |
| 2-diethylaminoethyl 2[(2,6-dichlorophenyl)amino]benzene acetate hydrochloride | Diclofenac | 3 | 6 | 9 |
| (RS)-N-[1-(1-benzothien-2-yl)ethyl]-N-(2-diethylaminoacetyloxy)urea hydrochloride | Zileuton | 10 | 20 | 30 |

TABLE 8-continued

| | Doses of HPPs/Drugs applied to Groups 3, 4, and 5 | | | |
|---|---|---|---|---|
| | | Drug | | |
| | | Dose (mg/kg) | Dose (mg/kg) | Dose (mg/kg) |
| | | | Group No. | |
| HPP | Parent drug | 3 | 4 | 5 |
| (RS)-5-[1-acetyloxy-2-(isopropylamino)ethyl]benzene-1,3-diol diacetate hydrochloride | Metaproterenol | 1 | 2 | 3 |
| Levomethamphetamine | N/A | 3 | 6 | 9 |

Airway responsiveness [transpulmonary resistance ($R_L$) and dynamic compliance ($C_{dyn}$)] to inhaled β-methacholine were determined following the same protocol as described in Example 16. The results are shown in Table 8.1.

TABLE 8.1

| | Airway Hyperresponsiveness | | | | |
|---|---|---|---|---|---|
| | Naïve | Vehicle | Low dose | Middle dose | High dose |
| Transpulmonary resistance (percent of saline control at 25 mg/ml methacholine) | 153 ± 21* | 313 ± 61 | 196 ± 17* | 163 ± 18* | 152 ± 19* |
| Dynamic compliance (percent of saline control at 25 mg/ml methacholine) | −33.1 ± 2.8* | −63.1 ± 3.2 | −48.2 ± 2.5* | −39.5 ± 2.9* | −36.1 ± 2.8* |

*P < 0.001, significant difference compared with vehicle-treated animals

Eosinophil numbers, neutrophil number and mononuclear cell numbers in BALF were determined following the same protocol as described in Example 16. The results are shown in Table 8.2.

TABLE 8.2

| | Eosinophil numbers, neutrophil number and mononuclear cell numbers in BALF | | | | |
|---|---|---|---|---|---|
| | Naïve | Vehicle | Low dose | Middle dose | High dose |
| Eosinophil Numbers in Blood (×10$^6$/mL) | 0.038 ± 0.012* | 0.519 ± 0.102 | 0.189 ± 0.033 | 0.096 ± 0.017* | 0.049 ± 0.019* |
| Neutrophil Number in Blood (×10$^6$/mL) | 0.50 ± 0.14* | 1.15 ± 0.19 | 0.69 ± 0.21* | 0.61 ± 0.17* | 0.55 ± 0.18* |
| Mononuclear cell numbers in Blood (×10$^6$/mL) | 2.27 ± 0.18* | 5.12 ± 0.29 | 2.79 ± 0.53 | 1.68 ± 0.21* | 1.55 ± 0.27* |
| Eosinophil Numbers in BALF (×10$^6$/mL) | 0.30 ± 0.07* | 1.82 ± 0.18 | 0.65 ± 0.24* | 0.52 ± 0.17* | 0.41 ± 0.16* |
| Neutrophil Number in BALF (×10$^6$/mL) | 0.35 ± 0.16* | 0.61 ± 0.21 | 0.42 ± 0.15* | 0.39 ± 0.16* | 0.36 ± 0.17* |
| Mononuclear cell numbers in BALF (×10$^6$/mL) | 0.31 ± 0.10* | 1.11 ± 0.16 | 0.63 ± 0.29 | 0.47 ± 0.15* | 0.42 ± 0.11* |

*P < 0.001, significant difference compared with vehicle animals.

IL-5 in lung homogenates of animals were determined following the same protocol as described in Example 16. The results are shown in Table 8.3.

TABLE 8.3

| | IL-5 in lung homogenates of animals | | | | |
|---|---|---|---|---|---|
| | Naïve | Vehicle | Low dose | Middle dose | High dose |
| IL-5(pg/mg of tissue) | 0.37 ± 0.14* | 1.14 ± 0.19 | 0.65 ± 0.15* | 0.53 ± 0.14* | 0.41 ± 0.11* |

*$P < 0.001$, significant difference compared with vehicle animals.

The results of this study show that the test drug combinations had strong anti-inflammatory and anti-asthma activities.

Example 23. Animal Test of Drug Combinations Disclosed Herein

Experiments similar to those described in Example 16 were performed. 48 female, BALB/c mice between 4 and 6 weeks of age were prepared and grouped as described in Example 16. Groups 1 and 2 were treated the same as described in Example 16.

In group 3, each mouse was applied with a combination of 6-D(−)-α-(4-ethyl-2,3-dioxo-1-piperazinylcarbonylamino)-α-phenylacetamidopenicillinic acid 2-(diethylamino)ethyl ester hydrochloride (10 mg/kg, 2% solution in 25% ethanol/water), diethylaminoethyl acetylsalicylate hydrochloride (10 mg/kg, 2% solution in 25% ethanol/water), (RS)—N-[1-(1-benzothien-2-yl)ethyl]-N-(2-diethylaminoacetyloxyl)urea hydrochloride (HPP of zileuton, 10 mg/kg, 2% solution in 25% ethanol/water), (RS)-5-[1-acetyloxy-2-(isopropylamino)ethyl]benzene-1,3-diol diacetate hydrochloride (1 mg/kg, 0.2% solution in 25% ethanol/water) and (isopropyl (E)-3-{6-[(E)-1-(4-methylphenyl)-3-pyrrolidine-1-yl-prop-1-enyl]pyridin-2-yl}prop-2-enoate) (1.5 mg/kg, 0.1% solution in 25% ethanol/water) to the shaved skin on the neck once per day from day 14 to day 22.

In group 4, each mouse was applied with a combination of 6-D(−)-α-(4-ethyl-2,3-dioxo-1-piperazinylcarbonylamino)-α-phenylacetamidopenicillinic acid 2-(diethylamino)ethyl ester hydrochloride (20 mg/kg, 4% solution in 25% ethanol/water), diethylaminoethyl acetylsalicylate hydrochloride (20 mg/kg, 4% solution in 25% ethanol/water), (RS)—N-[1-(1-benzothien-2-yl)ethyl]-N-(2-diethylaminoacetyloxyl)urea hydrochloride (20 mg/kg, 4% solution in 25% ethanol/water), (RS)-5-[1-acetyloxy-2-(isopropylamino)ethyl]benzene-1,3-diol diacetate hydrochloride (2 mg/kg, 0.4% solution in 25% ethanol/water) and (isopropyl (E)-3-{6-[(E)-1-(4-methylphenyl)-3-pyrrolidine-1-yl-prop-1-enyl]pyridin-2-yl}prop-2-enoate) (3 mg/kg, 0.2% solution in 25% ethanol/water) to the shaved skin on the neck once per day from day 15 to 22.

In group 5, each mouse was applied with a combination of 6-D(−)-α-(4-ethyl-2,3-dioxo-1-piperazinylcarbonylamino)-α-phenylacetamidopenicillinic acid 2-(diethylamino)ethyl ester hydrochloride (30 mg/kg, 6% solution in 25% ethanol/water), diethylaminoethyl acetylsalicylate hydrochloride (30 mg/kg, 6% solution in 25% ethanol/water), (RS)—N-[1-(1-benzothien-2-yl)ethyl]-N-(2-diethylaminoacetyloxyl)urea hydrochloride (30 mg/kg, 6% solution in 25% ethanol/water), (RS)-5-[1-acetyloxy-2-(isopropylamino)ethyl]benzene-1,3-diol diacetate hydrochloride (3 mg/kg, 0.6% solution in 25% ethanol/water) and (isopropyl (E)-3-{6-[(E)-1-(4-methylphenyl)-3-pyrrolidine-1-yl-prop-1-enyl]pyridin-2-yl}prop-2-enoate) (4.5 mg/kg, 0.3% solution in 25% ethanol/water) to the shaved skin on the neck once per day from day 15 to 22.

The doses of HPPs and drug applied to Groups 3, 4, and 5 are summarized in Table 9.

When applying a combination of a plurality of drugs (e.g. one or more HPPs and/or other drug(s)) to a subject, each drug could be applied separately, or one or more of the drugs could be applied at the same time as separate drugs (e.g. spraying two or more drugs at substantially the same time without mixing the drugs before spraying), or one or more drugs could be mixed together before applying to the subject, or any combination of the above application methods. The drugs could be applied in any order possible.

TABLE 9

| | | Drug | | |
|---|---|---|---|---|
| | | Dose (mg/kg) | Dose (mg/kg) | Dose (mg/kg) |
| | | Group No. | | |
| HPP | Parent drug | 3 | 4 | 5 |
| 6-D(−)-α-(4-ethyl-2,3-dioxo-1-piperazinylcarbonylamino)-α-phenylacetamidopenicillinic acid 2-(diethylamino)ethyl ester hydrochloride | Piperacillin | 10 | 20 | 30 |
| diethylaminoethyl acetylsalicylate hydrochloride | Aspirin | 10 | 20 | 30 |

TABLE 9-continued

| Doses of HPPs/Drugs applied to Groups 3, 4, and 5 | | | | |
|---|---|---|---|---|
| | | Drug | | |
| | | Dose (mg/kg) | Dose (mg/kg) | Dose (mg/kg) |
| | | | Group No. | |
| HPP | Parent drug | 3 | 4 | 5 |
| (RS)-N-[1-(1-benzothien-2-yl)ethyl]-N-(2-diethylaminoacetyloxy)urea hydrochloride | Zileuton | 10 | 20 | 30 |
| (RS)-5-[1-acetyloxy-2-(isopropylamino)ethyl]benzene-1,3-diol diacetate hydrochloride | Metaproterenol | 1 | 2 | 3 |
| (isopropyl (E)-3-{6-[(E)-1-(4-methylphenyl)-3-pyrrolidine-1-yl-prop-1-enyl]pyridin-2-yl}prop-2-enoate) | Acrivastine | 1.5 | 3 | 4.5 |

Airway responsiveness [transpulmonary resistance ($R_L$) and dynamic compliance ($C_{dyn}$)] to inhaled β-methacholine were determined following the same protocol as described in Example 16. The results are shown in Table 9.1.

TABLE 9.1

| Airway Hyperresponsiveness | | | | | |
|---|---|---|---|---|---|
| | Naïve | Vehicle | Low dose | Middle dose | High dose |
| Transpulmonary resistance (percent of saline control at 25 mg/ml methacholine) | 151 ± 23* | 311 ± 68 | 191 ± 21* | 151 ± 20* | 142 ± 17* |
| Dynamic compliance (percent of saline control at 25 mg/ml methacholine) | −32.1 ± 3.0* | −63.5 ± 3.1 | −47.2 ± 2.3* | −39.0 ± 2.8* | −34.1 ± 2.9* |

*$P < 0.001$, significant difference compared with vehicle-treated animals

Eosinophil numbers, neutrophil number and mononuclear cell numbers in BALF were determined following the same protocol as described in Example 16. The results are shown in Table 9.2.

TABLE 9.2

| Eosinophil numbers, neutrophil number and mononuclearcell numbers in BALF | | | | | |
|---|---|---|---|---|---|
| | Naïve | Vehicle | Low dose | Middle dose | High dose |
| Eosinophil Numbers in Blood (×10$^6$/mL) | 0.037 ± 0.010* | 0.529 ± 0.132 | 0.182 ± 0.028 | 0.090 ± 0.014* | 0.047 ± 0.015* |
| Neutrophil Number in Blood (×10$^6$/mL) | 0.51 ± 0.13* | 1.12 ± 0.16 | 0.67 ± 0.18* | 0.62 ± 0.11* | 0.43 ± 0.15* |
| Mononuclear cell numbers in Blood (×10$^6$/mL) | 2.21 ± 0.16 | 5.09 ± 0.17 | 2.69 ± 0.47 | 1.57 ± 0.22* | 1.32 ± 0.25* |
| Eosinophil Numbers in BALF (×10$^6$/mL) | 0.31 ± 0.05* | 1.87 ± 0.16 | 0.57 ± 0.21* | 0.41 ± 0.12* | 0.34 ± 0.08* |
| Neutrophil Number in BALF (×10$^6$/mL) | 0.32 ± 0.13* | 0.59 ± 0.16 | 0.40 ± 0.13* | 0.35 ± 0.14* | 0.28 ± 0.13* |
| Mononuclear cell numbers in BALF (×10$^6$/mL) | 0.29 ± 0.07* | 1.10 ± 0.21 | 0.59 ± 0.27 | 0.42 ± 0.18* | 0.34 ± 0.10* |

*$P < 0.001$, significant difference compared with vehicle animals.

IL-5 in lung homogenates of animals were determined following the same protocol as described in Example 16. The results are shown in Table 9.3.

TABLE 9.3

| IL-5 in lung homogenates of animals | | | | | |
|---|---|---|---|---|---|
| | Naïve | Vehicle | Low dose | Middle dose | High dose |
| IL-5(pg/mg of tissue) | 0.38 ± 0.15* | 1.09 ± 0.12 | 0.62 ± 0.14* | 0.45 ± 0.11* | 0.39 ± 0.07* |

*$P < 0.001$, significant difference compared with vehicle animals.

The results of this study show that the test drug combinations had strong anti-inflammatory and anti-asthma activities.

Example 25. Animal Test of Drug Combinations Disclosed Herein

Experiments similar to those described in Example 16 were performed. 48 female, BALB/c mice between 4 and 6 weeks of age were prepared and grouped as described in Example 16. Groups 1 and 2 were treated the same as described in Example 16.

In group 3, each mouse was applied with a combination of 6-phenoxyacetacetamidopenicillanic acid 2-(diethylamino)ethyl ester hydrochloride (10 mg/kg, 2% solution in 25% ethanol/water), 2-(diethylamino)ethyl acetylsalicylate hydrochloride (10 mg/kg, 2% solution in 25% ethanol/water), (RS)—N-[1-(1-benzothien-2-yl)ethyl]-N-(2-diethylaminoacetyloxyl)urea hydrochloride (HPP of zileuton, 10 mg/kg, 2% solution in 25% ethanol/water), sildenafil·citric acid (5 mg/kg, 2% in 25% ethanol/water), and (isopropyl(±)-4-[1-hydroxy-4-[4-(hydroxydiphenylmethyl)-1-piperidinyl]-butyl]-α,α-dimethyl benzeneacetate hydrochloride (10 mg/kg, 2% solution in 25% ethanol/water) to the shaved skin on the neck once per day from day 14 to day 22.

In group 4, each mouse was applied with a combination of 6-phenoxyacetacetamidopenicillanic acid 2-(diethylamino)ethyl ester hydrochloride (20 mg/kg, 4% solution in 25% ethanol/water), 2-(diethylamino)ethyl acetylsalicylate hydrochloride (20 mg/kg, 4% solution in 25% ethanol/water), (RS)—N-[1-(1-benzothien-2-yl)ethyl]-N-(2-diethylaminoacetyloxyl)urea hydrochloride (20 mg/kg, 4% solution in 25% ethanol/water), sildenafil·citric acid (10 mg/kg, 4% in 25% ethanol/water), and (isopropyl(±)-4-[1-hydroxy-4-[4-(hydroxydiphenylmethyl)-1-piperidinyl]-butyl]-α,α-dimethyl benzeneacetate hydrochloride (20 mg/kg, 4% solution in 25% ethanol/water) to the shaved skin on the neck once per day from day 15 to 22.

In group 5, each mouse was applied with a combination of 6-phenoxyacetacetamidopenicillanic acid 2-(diethylamino)ethyl ester hydrochloride (30 mg/kg, 6% solution in 25% ethanol/water), 2-(diethylamino)ethyl acetylsalicylate hydrochloride (30 mg/kg, 6% solution in 25% ethanol/water), (RS)—N-[1-(1-benzothien-2-yl)ethyl]-N-(2-diethylaminoacetyloxyl)urea hydrochloride (30 mg/kg, 6% solution in 25% ethanol/water), sildenafil·citric acid (15 mg/kg, 6% in 25% ethanol/water), and (isopropyl(±)-4-[1-hydroxy-4-[4-(hydroxydiphenylmethyl)-1-piperidinyl]-butyl]-α,α-dimethyl benzeneacetate hydrochloride (30 mg/kg, 6% solution in 25% ethanol/water) to the shaved skin on the neck once per day from day 15 to 22.

The doses of HPPs and drug applied to Groups 3, 4, and 5 are summarized in Table 10.

When applying a combination of a plurality of drugs (e.g. one or more HPPs and/or other drug(s)) to a subject, each drug could be applied separately, or one or more of the drugs could be applied at the same time as separate drugs (e.g. spraying two or more drugs at substantially the same time without mixing the drugs before spraying), or one or more drugs could be mixed together before applying to the subject, or any combination of the above application methods. The drugs could be applied in any order possible.

TABLE 10

| Doses of HPPs/Drugs applied to Groups 3, 4, and 5 | | | | |
|---|---|---|---|---|
| | | Drug | | |
| | | Dose (mg/kg) | Dose (mg/kg) | Dose (mg/kg) |
| | | Group No. | | |
| HPP | Parent drug | 3 | 4 | 5 |
| 6-phenoxyacetacetamidopenicillanic acid 2-(diethylamino)ethyl ester hydrochloride | Penicilin V | 10 | 20 | 30 |
| 2-(diethylamino)ethyl acetylsalicylate hydrochloride | Aspirin | 10 | 20 | 30 |
| (RS)-N-[1-(1-benzothien-2-yl)ethyl]-N-(2-diethylaminoacetyloxy)urea hydrochloride | Zileuton | 10 | 20 | 30 |
| sildenafil·citric acid | N/A | 5 | 10 | 15 |
| (isopropyl (±)-4-[1-hydroxy-4-[4-(hydroxydiphenylmethyl)-1-piperidinyl]-butyl]-α,α-dimethyl benzeneacetate hydrochloride | Fexofenadine | 10 | 20 | 30 |

Airway responsiveness [transpulmonary resistance ($R_L$) and dynamic compliance ($C_{dyn}$)] to inhaled β-methacholine were determined following the same protocol as described in Example 16. The results are shown in Table 10.1.

TABLE 10.1

| | Airway Hyperresponsiveness | | | | |
|---|---|---|---|---|---|
| | Naïve | Vehicle | Low dose | Middle dose | High dose |
| Transpulmonary resistance (percent of saline control at 25 mg/ml methacholine) | 149 ± 24* | 317 ± 61 | 193 ± 20* | 157 ± 21* | 143 ± 18* |
| Dynamic compliance (percent of saline control at 25 mg/ml methacholine) | −33.1 ± 3.1* | −63.9 ± 3.2 | −47.9 ± 2.1* | −39.9 ± 3.1* | −35.1 ± 2.6* |

*$P < 0.001$, significant difference compared with vehicle-treated animals

Eosinophil numbers, neutrophil number and mononuclear cell numbers in BALF were determined following the same protocol as described in Example 16. The results are shown in Table 10.2.

TABLE 10.2

| | Eosinophil numbers, neutrophil number and mononuclear cell numbers in BALF | | | | |
|---|---|---|---|---|---|
| | Naïve | Vehicle | Low dose | Middle dose | High dose |
| Eosinophil Numbers in Blood (×10$^6$/mL) | 0.035 ± 0.011* | 0.539 ± 0.135 | 0.199 ± 0.025 | 0.098 ± 0.015* | 0.052 ± 0.018* |
| Neutrophil Number in Blood (×10$^6$/mL) | 0.52 ± 0.15* | 1.15 ± 0.18 | 0.69 ± 0.21* | 0.61 ± 0.15* | 0.48 ± 0.18* |
| Mononuclear cell numbers in Blood (×10$^6$/mL) | 2.27 ± 0.17 | 5.12 ± 0.19 | 2.77 ± 0.48 | 1.54 ± 0.23* | 1.36 ± 0.27* |
| Eosinophil Numbers in BALF (×10$^6$/mL) | 0.35 ± 0.05* | 1.89 ± 0.17 | 0.63 ± 0.22* | 0.48 ± 0.15* | 0.36 ± 0.11* |
| Neutrophil Number in BALF (×10$^6$/mL) | 0.31 ± 0.15* | 0.61 ± 0.18 | 0.42 ± 0.15* | 0.38 ± 0.16* | 0.33 ± 0.15* |
| Mononuclear cell numbers in BALF (×10$^6$/mL) | 0.31 ± 0.08* | 1.12 ± 0.23 | 0.61 ± 0.29 | 0.43 ± 0.19* | 0.35 ± 0.12* |

*$P < 0.001$, significant difference compared with vehicle animals.

IL-5 in lung homogenates of animals were determined following the same protocol as described in Example 16. The results are shown in Table 10.3.

TABLE 10.3

| | IL-5 in lung homogenates of animals | | | | |
|---|---|---|---|---|---|
| | Naïve | Vehicle | Low dose | Middle dose | High dose |
| IL-5(pg/mg of tissue) | 0.39 ± 0.15* | 1.10 ± 0.13 | 0.65 ± 0.15* | 0.47 ± 0.12* | 0.42 ± 0.09* |

*$P < 0.001$, significant difference compared with vehicle animals.

The results of this study show that the test drug combinations had strong anti-inflammatory and anti-asthma activities.

Example 26. Animal Test of Drug Combinations Disclosed Herein

Experiments similar to those described in Example 16 were performed. 48 female, BALB/c mice between 4 and 6 weeks of age were prepared and grouped as described in Example 16. Groups 1 and 2 were treated the same as described in Example 16.

In group 3, each mouse was applied with a combination of 6-phenoxyacetacetamidopenicillanic acid 2-(diethylamino)ethyl ester hydrochloride (10 mg/kg, 2% solution in 25% ethanol/water), 2-(diethylamino)ethyl acetylsalicylate hydrochloride (10 mg/kg, 2% solution in 25% ethanol/water), (RS)—N-[1-(1-benzothien-2-yl)ethyl]-N-(2-diethylaminoacetyloxyl)urea hydrochloride (10 mg/kg, 2% solution in 25% ethanol/water), vardenafil·HCl (1.5 mg/kg, 0.5% in 25% ethanol/water), and (isopropyl(±)-4-[1-hydroxy-4-[4-(hydroxydiphenylmethyl)-1-piperidinyl]-butyl]-α,α-dimethyl benzeneacetate hydrochloride (10 mg/kg, 2% solution in 25% ethanol/water) to the shaved skin on the neck once per day from day 14 to day 22.

In group 4, each mouse was applied with a combination of 6-phenoxyacetacetamidopenicillanic acid 2-(diethylamino)ethyl ester hydrochloride (20 mg/kg, 4% solution in 25% ethanol/water), 2-(diethylamino)ethyl acetylsalicylate hydrochloride (20 mg/kg, 4% solution in 25% ethanol/water), (RS)—N-[1-(1-benzothien-2-yl)ethyl]-N-(2-diethylaminoacetyloxyl)urea hydrochloride (20 mg/kg, 4% solution in 25% ethanol/water), vardenafil·HCl (3 mg/kg, 1% in 25% ethanol/water), and (isopropyl(±)-4-[1-hydroxy-4-[4-(hydroxydiphenylmethyl)-1-piperidinyl]-butyl]-α,α-dimethyl benzeneacetate hydrochloride (20 mg/kg, 4% solution in 25% ethanol/water) to the shaved skin on the neck once per day from day 15 to 22.

In group 5, each mouse was applied with a combination of 6-phenoxyacetacetamidopenicillanic acid 2-(diethylamino)ethyl ester hydrochloride (30 mg/kg, 6% solution in 25% ethanol/water), 2-(diethylamino)ethyl acetylsalicylate hydrochloride (30 mg/kg, 6% solution in 25% ethanol/water), (RS)—N-[1-(1-benzothien-2-yl)ethyl]-N-(2-diethylaminoacetyloxyl)urea hydrochloride (30 mg/kg, 6% solution in 25% ethanol/water), vardenafil·HCl (4.5 mg/kg, 1.5% in 25% ethanol/water), and (isopropyl(±)-4-[1-hydroxy-4-[4-(hydroxydiphenylmethyl)-1-piperidinyl]-butyl]-α,α-dimethyl benzeneacetate hydrochloride (30 mg/kg, 6% solution in 25% ethanol/water) to the shaved skin on the neck once per day from day 15 to 22.

The doses of HPPs and drug applied to Groups 3, 4, and 5 are summarized in Table 11.

When applying a combination of a plurality of drugs (e.g. one or more HPPs and/or other drug(s)) to a subject, each drug could be applied separately, or one or more of the drugs could be applied at the same time as separate drugs (e.g. spraying two or more drugs at substantially the same time without mixing the drugs before spraying), or one or more drugs could be mixed together before applying to the subject, or any combination of the above application methods. The drugs could be applied in any order possible.

TABLE 11

Doses of HPPs/Drugs applied to Groups 3, 4, and 5

| | | Drug Dose (mg/kg) Group No. | | |
|---|---|---|---|---|
| HPP | Parent drug | 3 | 4 | 5 |
| 6-Phenoxyacetacetamidopenicillanic acid 2-(diethylamino)ethyl ester hydrochloride | Penicilin V | 10 | 20 | 30 |
| 2-(Diethylamino)ethyl acetylsalicylate hydrochloride | Aspirin | 10 | 20 | 30 |
| (RS)-N-[1-(1-Benzothien-2-yl)ethyl]-N-(2-diethylaminoacetyloxy)urea hydrochloride | Zileuton | 10 | 20 | 30 |
| Vardenafil•HCl | N/A | 1.5 | 3 | 4.5 |
| (Isopropyl (±)-4-[1-hydroxy-4-[4-(hydroxydiphenylmethyl)-1-piperidinyl]-butyl]-α,α-dimethyl benzeneacetate hydrochloride | Fexofenadine | 10 | 20 | 30 |

Airway responsiveness [transpulmonary resistance ($R_L$) and dynamic compliance ($C_{dyn}$)] to inhaled β-methacholine were determined following the same protocol as described in Example 16. The results are shown in Table 11.1.

TABLE 11.1

| Airway Hyperresponsiveness | | | | | |
|---|---|---|---|---|---|
| | Naïve | Vehicle | Low dose | Middle dose | High dose |
| Transpulmonary resistance (percent of saline control at 25 mg/ml methacholine) | 148 ± 24* | 312 ± 61 | 189 ± 23* | 155 ± 22* | 149 ± 21* |
| Dynamic compliance (percent of saline control at 25 mg/ml methacholine) | −34.1 ± 3.1* | −64.5 ± 2.8 | −49.2 ± 2.5* | −41.0 ± 2.9* | −34.7 ± 2.7* |

*$P < 0.001$, significant difference compared with vehicle-treated animals

Eosinophil numbers, neutrophil number and mononuclear cell numbers in BALF were determined following the same protocol as described in Example 16. The results are shown in Table 11.2.

TABLE 11.2

| Eosinophil numbers, neutrophil number and mononuclear cell numbers in BALF | | | | | |
|---|---|---|---|---|---|
| | Naïve | Vehicle | Low dose | Middle dose | High dose |
| Eosinophil Numbers in Blood (×10$^6$/mL) | 0.041 ± 0.011* | 0.551 ± 0.123 | 0.198 ± 0.035 | 0.111 ± 0.015* | 0.057 ± 0.017* |
| Neutrophil Number in Blood (×10$^6$/mL) | 0.55 ± 0.14* | 1.17 ± 0.17 | 0.76 ± 0.17* | 0.63 ± 0.15* | 0.53 ± 0.18* |
| Mononuclear cell numbers in Blood (×10$^6$/mL) | 2.25 ± 0.16 | 5.29 ± 0.19 | 2.88 ± 0.55 | 1.87 ± 0.23* | 1.48 ± 0.26* |
| Eosinophil Numbers in BALF (×10$^6$/mL) | 0.35 ± 0.06* | 1.81 ± 0.18 | 0.87 ± 0.24* | 0.53 ± 0.15* | 0.41 ± 0.11* |
| Neutrophil Number in BALF (×10$^6$/mL) | 0.31 ± 0.15* | 0.58 ± 0.19 | 0.43 ± 0.12* | 0.39 ± 0.13* | 0.33 ± 0.13* |
| Mononuclear cell numbers in BALF (×10$^6$/mL) | 0.28 ± 0.08* | 1.12 ± 0.20 | 0.67 ± 0.25 | 0.46 ± 0.16* | 0.38 ± 0.11* |

*$P < 0.001$, significant difference compared with vehicle animals.

IL-5 in lung homogenates of animals were determined following the same protocol as described in Example 16. The results are shown in Table 11.3.

TABLE 11.3

| IL-5 in lung homogenates of animals | | | | | |
|---|---|---|---|---|---|
| | Naïve | Vehicle | Low dose | Middle dose | High dose |
| IL-5(pg/mg of tissue) | 0.34 ± 0.16* | 1.03 ± 0.15 | 0.67 ± 0.18* | 0.51 ± 0.17* | 0.43 ± 0.11* |

*$P < 0.001$, significant difference compared with vehicle animals.

The results of this study show that the test drug combinations had strong anti-inflammatory and anti-asthma activities.

Example 27. Animal Test of Drug Combinations Disclosed Herein

Experiments similar to those described in Example 16 were performed. 48 female, BALB/c mice between 4 and 6 weeks of age were prepared and grouped as described in Example 16. Groups 1 and 2 were treated the same as described in Example 16.

In group 3, each mouse was applied with a combination of 3-[[(aminocarbonyl)oxy]methyl]-7-methoxy-8-oxo-7-[(2-thienylacetyl)amino]-5-thia-1-azabicyclo[4.2.0]oct-2-ene-2-carboxylic acid 2-(diethylamino)ethyl ester hydrochloride (10 mg/kg, 2% solution in 25% ethanol/water), 2-(diethylamino)ethyl acetylsalicylate hydrochloride (10 mg/kg, 2% solution in 25% ethanol/water), tadalafil hydrochloride (1.5 mg/kg, 0.5% solution in 25% ethanol/water), 2-(diethylamino)ethyl 2-[R-(E)]-1-[[[1-[3-[2-(7-chloro-2-quinolinyl)ethenyl]phenyl]-3-[2-(1-hydroxy-1-methylethyl)phenyl]propyl]thio]methyl]cyclopropaneacetate hydrochloride (1.5 mg/kg, 0.5% solution in 25% ethanol/water) and (isopropyl (E)-3-{6-[(E)-1-(4-methylphenyl)-3-pyrrolidine-1-yl-prop-1-enyl]pyridin-2-yl}prop-2-enoate) (1.5 mg/kg, 0.3% solution in 25% ethanol/water) to the shaved skin on the neck once per day from day 14 to day 22.

In group 4, each mouse was applied with a combination of 3-[[(aminocarbonyl)oxy]methyl]-7-methoxy-8-oxo-7-[(2-thienylacetyl)amino]-5-thia-1-azabicyclo[4.2.0]oct-2-ene-2-carboxylic acid 2-(diethylamino)ethyl ester hydrochloride (20 mg/kg, 4% solution in 25% ethanol/water), 2-(diethylamino)ethyl acetylsalicylate hydrochloride (20 mg/kg, 4% solution in 25% ethanol/water), tadalafil hydrochloride (3 mg/kg, 1% solution in 25% ethanol/water), 2-(diethylamino)ethyl 2-[R-(E)]-1-[[[1-[3-[2-(7-chloro-2-quinolinyl)ethenyl]phenyl]-3-[2-(1-hydroxy-1-methylethyl)phenyl]propyl]thio]methyl]cyclopropaneacetate hydrochloride (3 mg/kg, 1% solution in 25% ethanol/water) and (isopropyl (E)-3-{6-[(E)-1-(4-methylphenyl)-3-pyrrolidine-1-yl-prop-1-enyl]pyridin-2-yl}prop-2-enoate) (3 mg/kg, 0.6% solution in 25% ethanol/water) to the shaved skin on the neck once per day from day 15 to 22.

In group 5, each mouse was applied with a combination of 3-[[(aminocarbonyl)oxy]methyl]-7-methoxy-8-oxo-7-[(2-thienylacetyl)amino]-5-thia-1-azabicyclo[4.2.0]oct-2-ene-2-carboxylic acid 2-(diethylamino)ethyl ester hydrochloride (30 mg/kg, 6% solution in 25% ethanol/water), 2-(diethylamino)ethyl acetylsalicylate hydrochloride (30 mg/kg, 6% solution in 25% ethanol/water), tadalafil hydrochloride (145 mg/kg, 1.5% solution in 25% ethanol/water), 2-(diethylamino)ethyl 2-[R-(E)]-1-[[[1-[3-[2-(7-chloro-2-quinolinyl)ethenyl]phenyl]-3-[2-(1-hydroxy-1-methylethyl)phenyl]propyl]thio]methyl]cyclopropaneacetate hydrochloride (4.5 mg/kg, 1.5% solution in 25% ethanol/water) and (isopropyl (E)-3-{6-[(E)-1-(4-methylphenyl)-3-pyrrolidine-1-yl-prop-1-enyl]pyridin-2-yl}prop-2-enoate) (4.5 mg/kg, 0.9% solution in 25% ethanol/water) to the shaved skin on the neck once per day from day 15 to 22.

The doses of HPPs and drug applied to Groups 3, 4, and 5 are summarized in Table 12.

When applying a combination of a plurality of drugs (e.g. one or more HPPs and/or other drug(s)) to a subject, each drug could be applied separately, or one or more of the drugs could be applied at the same time as separate drugs (e.g. spraying two or more drugs at substantially the same time without mixing the drugs before spraying), or one or more drugs could be mixed together before applying to the subject, or any combination of the above application methods. The drugs could be applied in any order possible.

TABLE 12

Doses of HPPs/Drugs applied to Groups 3, 4, and 5

| HPP | Parent drug | Drug Dose (mg/kg) Group No. 3 | Dose (mg/kg) 4 | Dose (mg/kg) 5 |
| --- | --- | --- | --- | --- |
| 3-[[(aminocarbonyl)oxy]methyl]-7-methoxy-8-oxo-7-[(2-thienylacetyl)amino]-5-thia-1-azabicyclo[4.2.0]oct-2-ene-2-carboxylic acid 2-(diethylamino)ethyl ester hydrochloride | Cefoxitin | 10 | 20 | 30 |
| 2-(diethylamino)ethyl acetylsalicylate hydrochloride | Aspirin | 10 | 20 | 30 |
| tadalafil hydrochloride | N/A | 1.5 | 3 | 4.5 |
| 2-(diethylamino)ethyl 2-[R-(E)]-1-[[[1-[3-[2-(7-chloro-2-quinolinyl)ethenyl]phenyl]-3-[2-(1-hydroxy-1-methylethyl)phenyl]propyl]thio]methyl]cyclopropaneacetate hydrochloride | Montelukast | 1.5 | 3 | 4.5 |
| (isopropyl (E)-3-{6-[(E)-1-(4-methylphenyl)-3-pyrrolidine-1-yl-prop-1-enyl]pyridin-2-yl}prop-2-enoate) | Acrivastine | 1.5 | 3 | 4.5 |

Airway responsiveness [transpulmonary resistance ($R_L$) and dynamic compliance ($C_{dyn}$)] to inhaled β-methacholine were determined following the same protocol as described in Example 16. The results are shown in Table 12.1.

TABLE 12.1

| Airway Hyperresponsiveness | | | | | |
|---|---|---|---|---|---|
| | Naïve | Vehicle | Low dose | Middle dose | High dose |
| Transpulmonary resistance (percent of saline control at 25 mg/ml methacholine) | 153 ± 21* | 319 ± 62 | 212 ± 20* | 167 ± 23* | 159 ± 18* |
| Dynamic compliance (percent of saline control at 25 mg/ml methacholine) | −32.6 ± 3.1* | −62.5 ± 2.9 | −49.2 ± 2.1* | −41.0 ± 2.4* | −33.9 ± 2.8* |

*$P < 0.001$, significant difference compared with vehicle-treated animals

Eosinophil numbers, neutrophil number and mononuclear cell numbers in BALF were determined following the same protocol as described in Example 16. The results are shown in Table 12.2.

TABLE 12.2

| Eosinophil numbers, neutrophil number and mononuclear cell numbers in BALF | | | | | |
|---|---|---|---|---|---|
| | Naïve | Vehicle | Low dose | Middle dose | High dose |
| Eosinophil Numbers in Blood (×10$^6$/mL) | 0.043 ± 0.015* | 0.556 ± 0.127 | 0.199 ± 0.025 | 0.120 ± 0.017* | 0.053 ± 0.016* |
| Neutrophil Number in Blood (×10$^6$/mL) | 0.52 ± 0.15* | 1.09 ± 0.18 | 0.72 ± 0.19* | 0.65 ± 0.13* | 0.53 ± 0.17* |
| Mononuclear cell numbers in Blood (×10$^6$/mL) | 2.17 ± 0.19 | 5.01 ± 0.19 | 2.99 ± 0.51 | 1.66 ± 0.24* | 1.53 ± 0.28* |
| Eosinophil Numbers in BALF (×10$^6$/mL) | 0.32 ± 0.06* | 1.89 ± 0.17 | 0.71 ± 0.23* | 0.62 ± 0.13* | 0.44 ± 0.11* |
| Neutrophil Number in BALF (×10$^6$/mL) | 0.30 ± 0.15* | 0.61 ± 0.17 | 0.42 ± 0.14* | 0.39 ± 0.17* | 0.34 ± 0.15* |
| Mononuclear cell numbers in BALF (×10$^6$/mL) | 0.28 ± 0.08* | 1.11 ± 0.18 | 0.61 ± 0.21 | 0.44 ± 0.15* | 0.39 ± 0.11* |

*$P < 0.001$, significant difference compared with vehicle animals.

IL-5 in lung homogenates of animals were determined following the same protocol as described in Example 16. The results are shown in Table 12.3.

TABLE 12.3

| IL-5 in lung homogenates of animals | | | | | |
|---|---|---|---|---|---|
| | Naïve | Vehicle | Low dose | Middle dose | High dose |
| IL-5 (pg/mg of tissue) | 0.37 ± 0.13* | 1.07 ± 0.15 | 0.69 ± 0.17* | 0.52 ± 0.13* | 0.41 ± 0.09* |

*$P < 0.001$, significant difference compared with vehicle animals.

The results of this study show that the test drug combinations had strong anti-inflammatory and anti-asthma activities.

Example 28. Animal Test of Drug Combinations Disclosed Herein

Experiments similar to those described in Example 16 were performed. 48 female, BALB/c mice between 4 and 6 weeks of age were prepared and grouped as described in Example 16. Groups 1 and 2 were treated the same as described in Example 16.

In group 3, each mouse was applied with a combination of 3-[[(aminocarbonyl)oxy]methyl]-7-methoxy-8-oxo-7-[(2-thienylacetyl)amino]-5-thia-1-azabicyclo[4.2.0]oct-2-ene-2-carboxylic acid 2-(diethylamino)ethyl ester hydrochloride (10 mg/kg, 2% solution in 25% ethanol/water), 2-(diethylamino)ethyl 2-(ρ-isobutylphenyl) propionate hydrochloride (5 mg/kg, 1% solution in 25% ethanol/water), diethylaminoethyl [R-(E)]-1-[[[1-[3-[2-(7-chloro-2-quinolinyl)ethenyl]phenyl]-3-[2-(1-hydroxy-1-methylethyl)phenyl]propyl]thio]methyl]cyclopropaneacetate hydrochloride (1 mg/kg, 0.3% solution in 25% ethanol/water), udenafil hydrochloride (3 mg/kg, 1% solution in 25% ethanol/water), and (isopropyl (E)-3-{6-[(E)-1-(4-methylphenyl)-3-pyrrolidine-1-yl-prop-1-enyl]pyridin-2-yl}prop-2-enoate) (1.5 mg/kg, 0.3% solution in 25% ethanol/water) to the shaved skin on the neck once per day from day 14 to day 22.

In group 4, each mouse was applied with a combination of 3-[[(aminocarbonyl)oxy]methyl]-7-methoxy-8-oxo-7-[(2-thienylacetyl)amino]-5-thia-1-azabicyclo[4.2.0]oct-2-ene-2-carboxylic acid 2-(diethylamino)ethyl ester hydrochloride (20 mg/kg, 4% solution in 25% ethanol/water), 2-(diethylamino)ethyl 2-(ρ-isobutylphenyl) propionate hydrochloride (10 mg/kg, 2% solution in 25% ethanol/water), diethylaminoethyl [R-(E)]-1-[[[1-[3-[2-(7-chloro-2-quinolinyl)ethenyl]phenyl]-3-[2-(1-hydroxy-1-methylethyl)phenyl]propyl]thio]methyl]cyclopropaneacetate hydrochloride (2 mg/kg, 0.6% solution in 25% ethanol/water), udenafil hydrochloride (6 mg/kg, 2% solution in 25% ethanol/water), and (isopropyl (E)-3-{6-[(E)-1-(4-methylphenyl)-3-pyrrolidine-1-yl-prop-1-enyl]pyridin-2-yl}prop-2-enoate) (3 mg/kg, 0.6% solution in 25% ethanol/water) to the shaved skin on the neck once per day from day 15 to 22.

In group 5, each mouse was applied with a combination of 3-[[(aminocarbonyl)oxy]methyl]-7-methoxy-8-oxo-7-[(2-thienylacetyl)amino]-5-thia-1-azabicyclo[4.2.0]oct-2-ene-2-carboxylic acid 2-(diethylamino)ethyl ester hydrochloride (30 mg/kg, 6% solution in 25% ethanol/water), 2-(diethylamino)ethyl 2-(ρ-isobutylphenyl) propionate hydrochloride (15 mg/kg, 3% solution in 25% ethanol/water), diethylaminoethyl [R-(E)]-1-[[[1-[3-[2-(7-chloro-2-quinolinyl)ethenyl]phenyl]-3-[2-(1-hydroxy-1-methylethyl)phenyl]propyl]thio]methyl]cyclopropaneacetate hydrochloride (3 mg/kg, 0.9% solution in 25% ethanol/water), udenafil hydrochloride (9 mg/kg, 3% solution in 25% ethanol/water), and (isopropyl (E)-3-{6-[(E)-1-(4-methylphenyl)-3-pyrrolidine-1-yl-prop-1-enyl]pyridin-2-yl}prop-2-enoate) (4.5 mg/kg, 0.9% solution in 25% ethanol/water) to the shaved skin on the neck once per day from day 15 to 22.

The doses of HPPs and drug applied to Groups 3, 4, and 5 are summarized in Table 13.

When applying a combination of a plurality of drugs (e.g. one or more HPPs and/or other drug(s)) to a subject, each drug could be applied separately, or one or more of the drugs could be applied at the same time as separate drugs (e.g. spraying two or more drugs at substantially the same time without mixing the drugs before spraying), or one or more drugs could be mixed together before applying to the subject, or any combination of the above application methods. The drugs could be applied in any order possible.

TABLE 13

Doses of HPPs/Drugs applied to Groups 3, 4, and 5

| HPP/Drug | Parent drug | Dose (mg/kg) | Dose (mg/kg) | Dose (mg/kg) |
|---|---|---|---|---|
| Group No. | | 3 | 4 | 5 |
| 3-[[(Aminocarbonyl)oxy]methyl]-7-methoxy-8-oxo-7-[(2-thienylacetyl)amino]-5-thia-1-azabicyclo[4.2.0]oct-2-ene-2-carboxylic acid 2-(diethylamino)ethyl ester hydrochloride | Cefoxitin | 10 | 20 | 30 |
| 2-(Diethylamino)ethyl 2-(ρ-isobutylphenyl) propionate hydrochloride | Ibuprofen | 5 | 10 | 15 |
| Diethylaminoethyl [R-(E)]-1-[[[1-[3-[2-(7-chloro-2-quinolinyl)ethenyl]phenyl]-3-[2-(1-hydroxy-1-methylethyl)phenyl]propyl]thio]methyl]cyclopropaneacetate hydrochloride | Montelukast | 1 | 2 | 3 |
| udenafil hydrochloride | N/A | 3 | 6 | 9 |
| (Isopropyl (E)-3-{6-[(E)-1-(4-methylphenyl)-3-pyrrolidine-1-yl-prop-1-enyl]pyridin-2-yl}prop-2-enoate) | Acrivastine | 1.5 | 3 | 4.5 |

Airway responsiveness [transpulmonary resistance ($R_L$) and dynamic compliance ($C_{dyn}$)] to inhaled β-methacholine were determined following the same protocol as described in Example 16. The results are shown in Table 13.1.

TABLE 13.1

Airway Hyperresponsiveness

| | Naïve | Vehicle | Low dose | Middle dose | High dose |
|---|---|---|---|---|---|
| Transpulmonary resistance (percent of saline control at 25 mg/ml methacholine) | 149 ± 21* | 307 ± 63 | 211 ± 23* | 187 ± 21* | 152 ± 19* |
| Dynamic compliance (percent of saline control at 25 mg/ml methacholine) | −32.7 ± 3.0* | −65.1 ± 3.4 | −49.2 ± 2.1* | −41.6 ± 2.7* | −35.1 ± 2.6* |

*$P < 0.001$, significant difference compared with vehicle-treated animals

Eosinophil numbers, neutrophil number and mononuclear cell numbers in BALF were determined following the same protocol as described in Example 16. The results are shown in Table 13.2.

TABLE 13.2

Eosinophil numbers, neutrophil number and mononuclear cell numbers in BALF

|  | Naïve | Vehicle | Low dose | Middle dose | High dose |
| --- | --- | --- | --- | --- | --- |
| Eosinophil Numbers in Blood ($\times 10^6$/mL) | 0.039 ± 0.011* | 0.527 ± 0.127 | 0.191 ± 0.031 | 0.123 ± 0.016* | 0.056 ± 0.016* |
| Neutrophil Number in Blood ($\times 10^6$/mL) | 0.52 ± 0.14* | 1.11 ± 0.18 | 0.71 ± 0.17* | 0.64 ± 0.13* | 0.45 ± 0.16* |
| Mononuclear cell numbers in Blood ($\times 10^6$/mL) | 1.92 ± 0.17 | 5.11 ± 0.18 | 2.73 ± 0.49 | 1.97 ± 0.21* | 1.62 ± 0.24* |
| Eosinophil Numbers in BALF ($\times 10^6$/mL) | 0.30 ± 0.06* | 1.81 ± 0.14 | 0.62 ± 0.23* | 0.51 ± 0.16* | 0.39 ± 0.09* |
| Neutrophil Number in BALF ($\times 10^6$/mL) | 0.34 ± 0.14* | 0.63 ± 0.18 | 0.49 ± 0.16* | 0.41 ± 0.17* | 0.35 ± 0.16* |
| Mononuclear cell numbers in BALF ($\times 10^6$/mL) | 0.31 ± 0.09* | 1.11 ± 0.24 | 0.64 ± 0.21 | 0.51 ± 0.15* | 0.39 ± 0.13* |

*$P < 0.001$, significant difference compared with vehicle animals.

IL-5 in lung homogenates of animals were determined following the same protocol as described in Example 16. The results are shown in Table 13.3.

TABLE 13.3

IL-5 in lung homogenates of animals

|  | Naïve | Vehicle | Low dose | Middle dose | High dose |
| --- | --- | --- | --- | --- | --- |
| IL-5 (pg/mg of tissue) | 0.39 ± 0.16* | 1.11 ± 0.14 | 0.65 ± 0.16* | 0.49 ± 0.12* | 0.42 ± 0.10* |

*$P < 0.001$, significant difference compared with vehicle animals.

The results of this study show that the test drug combinations had strong anti-inflammatory and anti-asthma activities.

Example 29. Animal Test of Drug Combinations Disclosed Herein

Experiments similar to those described in Example 16 were performed. 48 female, BALB/c mice between 4 and 6 weeks of age were prepared and grouped as described in Example 16. Groups 1 and 2 were treated the same as described in Example 16.

In group 3, each mouse was applied with a combination of 6-phenoxyacetacetamidopenicillanic acid 2-diethylaminoethyl ester hydrochloride (10 mg/kg, 2% solution in 25% ethanol/water), 2-(diethylamino)ethyl 2-(p-isobutylphenyl) propionate hydrochloride (5 mg/kg, 1% solution in 25% ethanol/water), (RS)—N-[1-(1-benzothien-2-yl)ethyl]-N-(2-diethylaminoacetyloxyl)urea hydrochloride (10 mg/kg, 2% solution in 25% ethanol/water), sildenafil citrate (3 mg/kg, 0.6% solution in 25% ethanol/water) and isopropyl (±)-4-[1-hydroxy-4-[4-(hydroxydiphenylmethyl)-1-piperidinyl]-butyl]-α,α-dimethyl benzeneacetate hydrochloride (10 mg/kg, 2% solution in 25% ethanol/water) to the shaved skin on the neck once per day from day 14 to day 22.

In group 4, each mouse was applied with a combination of 6-phenoxyacetacetamidopenicillanic acid 2-diethylaminoethyl ester hydrochloride (20 mg/kg, 4% solution in 25% ethanol/water), 2-(diethylamino)ethyl 2-(p-isobutylphenyl) propionate hydrochloride (10 mg/kg, 2% solution in 25% ethanol/water), RS)—N-[1-(1-benzothien-2-yl)ethyl]-N-(2-diethylaminoacetyloxyl)urea hydrochloride (20 mg/kg, 4% solution in 25% ethanol/water), sildenafil citrate (6 mg/kg, 1.2% solution in 25% ethanol/water) and isopropyl(±)-4-[1-hydroxy-4-[4-(hydroxydiphenylmethyl)-1-piperidinyl]-butyl]-α,α-dimethyl benzeneacetate hydrochloride (20 mg/kg, 4% solution in 25% ethanol/water) to the shaved skin on the neck once per day from day 15 to 22.

In group 5, each mouse was applied with a combination of 6-phenoxyacetacetamidopenicillanic acid 2-diethylaminoethyl ester hydrochloride (30 mg/kg, 6% solution in 25% ethanol/water), 2-(diethylamino)ethyl 2-(p-isobutylphenyl) propionate hydrochloride (15 mg/kg, 3% solution in 25% ethanol/water), (RS)—N-[1-(1-benzothien-2-yl)ethyl]-N-(2-diethylaminoacetyloxyl)urea hydrochloride (30 mg/kg, 6% solution in 25% ethanol/water), sildenafil citrate (9 mg/kg, 1.8% solution in 25% ethanol/water) and isopropyl (±)-4-[1-hydroxy-4-[4-(hydroxydiphenylmethyl)-1-piperidinyl]-butyl]-α,α-dimethyl benzeneacetate hydrochloride (30 mg/kg, 6% solution in 25% ethanol/water) to the shaved skin on the neck once per day from day 15 to 22.

The doses of HPPs and drug applied to Groups 3, 4, and 5 are summarized in Table 14.

When applying a combination of a plurality of drugs (e.g. one or more HPPs and/or other drug(s)) to a subject, each drug could be applied separately, or one or more of the drugs could be applied at the same time as separate drugs (e.g. spraying two or more drugs at substantially the same time without mixing the drugs before spraying), or one or more drugs could be mixed together before applying to the subject, or any combination of the above application methods. The drugs could be applied in any order possible.

TABLE 14

Doses of HPPs/Drugs applied to Groups 3, 4, and 5

| HPP | Parent drug | Drug Dose (mg/kg) | Dose (mg/kg) | Dose (mg/kg) |
|---|---|---|---|---|
| Group No. | | 3 | 4 | 5 |
| 6-Phenoxyacetacetamidopenicillanic acid 2-diethylaminoethyl ester hydrochloride | Penicilin V | 10 | 20 | 30 |
| 2-(Diethylamino)ethyl 2-(p-isobutylphenyl) propionate hydrochloride | Ibuprofen | 5 | 10 | 15 |
| (RS) - N-[1-(1-Benzothien-2-yl)ethyl]-N-(2-diethylaminoacetyloxy)urea hydrochloride | Zileuton | 10 | 20 | 30 |
| Sildenafil citrate | N/A | 3 | 6 | 9 |
| Isopropyl (±)-4-[1-hydroxy-4-[4-(hydroxydiphenylmethyl)-1-piperidinyl]-butyl]-α,α-dimethyl benzeneacetate hydrochloride | Fexofenadine | 10 | 20 | 30 |

Airway responsiveness [transpulmonary resistance ($R_L$) and dynamic compliance ($C_{dyn}$)] to inhaled β-methacholine were determined following the same protocol as described in Example 16. The results are shown in Table 14.1.

TABLE 14.1

Airway Hyperresponsiveness

| | Naïve | Vehicle | Low dose | Middle dose | High dose |
|---|---|---|---|---|---|
| Transpulmonary resistance (percent of saline control at 25 mg/ml methacholine) | 147 ± 24* | 301 ± 60 | 197 ± 23* | 171 ± 18* | 152 ± 19* |
| Dynamic compliance (percent of saline control at 25 mg/ml methacholine) | −32.4 ± 3.0* | −64.1 ± 3.0 | 49.1 ± 2.1* | −41.0 ± 2.7* | −37.1 ± 2.1* |

*P < 0.001, significant difference compared with vehicle-treated animals

Eosinophil numbers, neutrophil number and mononuclear cell numbers in BALF were determined following the same protocol as described in Example 16. The results are shown in Table 14.2.

TABLE 14.2

Eosinophil numbers, neutrophil number and mononuclear cell numbers in BALF

| | Naïve | Vehicle | Low dose | Middle dose | High dose |
|---|---|---|---|---|---|
| Eosinophil Numbers in Blood (×10$^6$/mL) | 0.042 ± 0.011* | 0.511 ± 0.117 | 0.193 ± 0.031 | 0.115 ± 0.016* | 0.057 ± 0.016* |
| Neutrophil Number in Blood (×10$^6$/mL) | 0.53 ± 0.14* | 1.11 ± 0.19 | 0.73 ± 0.19* | 0.61 ± 0.13* | 0.49 ± 0.11* |
| Mononuclear cell numbers in Blood (×10$^6$/mL) | 2.01 ± 0.17 | 5.11 ± 0.14 | 2.89 ± 0.45 | 1.77 ± 0.25* | 1.52 ± 0.29* |
| Eosinophil Numbers in BALF (×10$^6$/mL) | 0.33 ± 0.07* | 1.81 ± 0.17 | 0.79 ± 0.27* | 0.49 ± 0.17* | 0.39 ± 0.14* |
| Neutrophil Number in BALF (×10$^6$/mL) | 0.31 ± 0.18* | 0.61 ± 0.17 | 0.49 ± 0.18* | 0.46 ± 0.17* | 0.38 ± 0.17* |
| Mononuclear cell numbers in BALF (×10$^6$/mL) | 0.32 ± 0.09* | 1.11 ± 0.20 | 0.64 ± 0.22 | 0.49 ± 0.11* | 0.41 ± 0.14* |

*P < 0.001, significant difference compared with vehicle animals.

IL-5 in lung homogenates of animals were determined following the same protocol as described in Example 16. The results are shown in Table

TABLE 14.3

| IL-5 in lung homogenates of animals | | | | | |
|---|---|---|---|---|---|
| | Naïve | Vehicle | Low dose | Middle dose | High dose |
| IL-5 pg/mg of tissue) | 0.41 ± 0.16* | 1.01 ± 0.11 | 0.65 ± 0.17* | 0.55 ± 0.16* | 0.45 ± 0.15* |

*P < 0.001, significant difference compared with vehicle animals.

The results of this study show that the test drug combinations had strong anti-inflammatory and anti-asthma activities.

Example 30. Animal Test of Drug Combinations Disclosed Herein

Experiments similar to those described in Example 16 were performed. 48 female, BALB/c mice between 4 and 6 weeks of age were prepared and grouped as described in Example 16. Groups 1 and 2 were treated the same as described in Example 16.

In group 3, each mouse was applied with a combination of 6-phenoxyacetacetamidopenicillanic acid 2-diethylaminoethyl ester hydrochloride (10 mg/kg, 2% solution in 25% ethanol/water), 2-(diethylamino)ethyl 2-(p-isobutylphenyl) propionate hydrochloride (5 mg/kg, 1% solution in 25% ethanol/water), (RS)—N-[1-(1-benzothien-2-yl)ethyl]-N-(2-diethylaminoacetyloxyl)urea hydrochloride (10 mg/kg, 2% solution in 25% ethanol/water), vardenafil hydrochloride (3 mg/kg, 0.6% solution in 25% ethanol/water) and isopropyl(±)-4-[1-hydroxy-4-[4-(hydroxydiphenylmethyl)-1-piperidinyl]-butyl]-α,α-dimethyl benzeneacetate hydrochloride (10 mg/kg, 2% solution in 25% ethanol/water) to the shaved skin on the neck once per day from day 14 to day 22.

In group 4, each mouse was applied with a combination of 6-phenoxyacetacetamidopenicillanic acid 2-diethylaminoethyl ester hydrochloride (20 mg/kg, 4% solution in 25% ethanol/water), 2-(diethylamino)ethyl 2-(p-isobutylphenyl) propionate hydrochloride (10 mg/kg, 2% solution in 25% ethanol/water), (RS)—N-[1-(1-benzothien-2-yl)ethyl]-N-(2-diethylaminoacetyloxyl)urea hydrochloride (20 mg/kg, 4% solution in 25% ethanol/water), vardenafil hydrochloride (6 mg/kg, 1.2% solution in 25% ethanol/water) and isopropyl(±)-4-[1-hydroxy-4-[4-(hydroxydiphenylmethyl)-1-piperidinyl]-butyl]-α,α-dimethyl benzeneacetate hydrochloride (20 mg/kg, 4% solution in 25% ethanol/water) to the shaved skin on the neck once per day from day 15 to 22.

In group 5, each mouse was applied with a combination of 6-phenoxyacetacetamidopenicillanic acid 2-diethylaminoethyl ester hydrochloride (30 mg/kg, 6% solution in 25% ethanol/water), 2-(diethylamino)ethyl 2-(p-isobutylphenyl) propionate hydrochloride (15 mg/kg, 3% solution in 25% ethanol/water), (RS)—N-[1-(1-benzothien-2-yl)ethyl]-N-(2-diethylaminoacetyloxyl)urea hydrochloride (30 mg/kg, 6% solution in 25% ethanol/water), vardenafil hydrochloride (9 mg/kg, 2% solution in 25% ethanol/water) and isopropyl (±)-4-[1-hydroxy-4-[4-(hydroxydiphenylmethyl)-1-piperidinyl]-butyl]-α,α-dimethyl benzeneacetate hydrochloride (30 mg/kg, 6% solution in 25% ethanol/water) to the shaved skin on the neck once per day from day 15 to 22.

The doses of HPPs and drug applied to Groups 3, 4, and 5 are summarized in Table 15.

When applying a combination of a plurality of drugs (e.g. one or more HPPs and/or other drug(s)) to a subject, each drug could be applied separately, or one or more of the drugs could be applied at the same time as separate drugs (e.g. spraying two or more drugs at substantially the same time without mixing the drugs before spraying), or one or more drugs could be mixed together before applying to the subject, or any combination of the above application methods. The drugs could be applied in any order possible.

TABLE 15

Doses of HPPs/Drugs applied to Groups 3, 4, and 5

| | | Drug | | |
|---|---|---|---|---|
| HPP | Parent drug | Dose (mg/kg) | Dose (mg/kg) | Dose (mg/kg) |
| Group No. | | 3 | 4 | 5 |
| 6-Phenoxyacetacetamidopenicillanic acid 2-diethylaminoethyl ester hydrochloride | Penicilin V | 10 | 20 | 30 |
| 2-(Diethylamino)ethyl 2-(p-isobutylphenyl) propionate hydrochloride | Ibuprofen | 5 | 10 | 15 |
| (RS) - N-[1-(1-benzothien-2-yl)ethyl]-N-(2-diethylaminoacetyloxy)urea hydrochloride | Zileuton | 10 | 20 | 30 |
| Vardenafil hydrochloride | N/A | 3 | 6 | 9 |
| Isopropyl (±)-4-[1-hydroxy-4-[4-(hydroxydiphenylmethyl)-1-piperidinyl]-butyl]-α,α-dimethyl benzeneacetate hydrochloride | Fexofenadine | 10 | 20 | 30 |

Airway responsiveness [transpulmonary resistance ($R_L$) and dynamic compliance ($C_{dyn}$)] to inhaled β-methacholine were determined following the same protocol as described in Example 16. The results are shown in Table 15.1.

TABLE 15.1

| Airway Hyperresponsiveness | | | | | |
| --- | --- | --- | --- | --- | --- |
|  | Naïve | Vehicle | Low dose | Middle dose | High dose |
| Transpulmonary resistance (percent of saline control at 25 mg/ml methacholine) | 149 ± 26* | 301 ± 62 | 215 ± 19* | 181 ± 21* | 148 ± 19* |
| Dynamic compliance (percent of saline control at 25 mg/ml methacholine) | −33.5 ± 3.1* | −64.5 ± 3.0 | −48.9 ± 2.1* | −39.9 ± 2.2* | −35.9 ± 2.5* |

*P < 0.001, significant difference compared with vehicle-treated animals

Eosinophil numbers, neutrophil number and mononuclear cell numbers in BALF were determined following the same protocol as described in Example 16. The results are shown in Table 15.2.

TABLE 15.2

| Eosinophil numbers, neutrophil number and mononuclear cell numbers in BALF | | | | | |
| --- | --- | --- | --- | --- | --- |
|  | Naïve | Vehicle | Low dose | Middle dose | High dose |
| Eosinophil Numbers in Blood (×10$^6$/mL) | 0.050 ± 0.011* | 0.517 ± 0.141 | 0.196 ± 0.026 | 0.115 ± 0.017* | 0.053 ± 0.017* |
| Neutrophil Number in Blood (×10$^6$/mL) | 0.49 ± 0.14* | 1.11 ± 0.17 | 0.75 ± 0.19* | 0.63 ± 0.13* | 0.47 ± 0.17* |
| Mononuclear cell numbers in Blood (×10$^6$/mL) | 2.26 ± 0.17 | 5.01 ± 0.18 | 2.71 ± 0.42 | 1.55 ± 0.21* | 1.34 ± 0.21* |
| Eosinophil Numbers in BALF (×10$^6$/mL) | 0.30 ± 0.07* | 1.89 ± 0.18 | 0.71 ± 0.25* | 0.49 ± 0.18* | 0.38 ± 0.13* |
| Neutrophil Number in BALF (×10$^6$/mL) | 0.30 ± 0.15* | 0.56 ± 0.17 | 0.41 ± 0.15* | 0.38 ± 0.17* | 0.32 ± 0.15* |
| Mononuclear cell numbers in BALF (×10$^6$/mL) | 0.28 ± 0.07* | 1.17 ± 0.20 | 0.71 ± 0.25 | 0.51 ± 0.17* | 0.37 ± 0.13* |

*P < 0.001, significant difference compared with vehicle animals.

IL-5 in lung homogenates of animals were determined following the same protocol as described in Example 16. The results are shown in Table 15.3.

TABLE 15.3

| IL-5 in lung homogenates of animals | | | | | |
| --- | --- | --- | --- | --- | --- |
|  | Naïve | Vehicle | Low dose | Middle dose | High dose |
| IL-5 (pg/mg of tissue) | 0.34 ± 0.13* | 1.01 ± 0.15 | 0.66 ± 0.16* | 0.47 ± 0.15* | 0.37 ± 0.13* |

*P < 0.001, significant difference compared with vehicle animals.

The results of this study show that the test drug combinations had strong anti-inflammatory and anti-asthma activities.

What is claimed is:

1. A topical pharmaceutical formulation comprising a pharmaceutically acceptable carrier and a compound of Structure LRA-1:

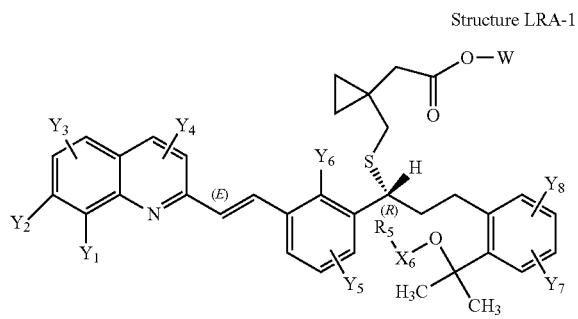

Structure LRA-1 wherein
- $X_5$ is selected from nothing, $C(=O)$, $OC(=O)$, $CH_2$, O, and $NR_5$;
- $Y_1$, $Y_2$, $Y_3$, $Y_4$, $Y_5$, $Y_6$, $Y_7$, and $Y_8$ are each independently selected from H, OH, OW, $OC(=O)W$, $OC(=O)CH_3$, $CH_2OR_6$, $CH_2C(=O)OR_5$, $OR_6$, $CF_3$, $OCF_3$, $CH_2(CH_2)_nOR_6$, F, Br, I, Cl, $C(=O)R_5$, $(CH_3)_2C(OR_6)—$, $CH_3CH(OH)—$, $(CH_3)_2CH—$, $CH_3CH_2—$, substituted and unsubstituted $C_1$-$C_{30}$ alkyl, substituted and unsubstituted $C_1$-$C_{30}$ alkoxyl, and substituted and unsubstituted $C_1$-$C_{30}$ alkylamino, wherein n is an integer selected from 1 to 10;
- $R_5$ is selected from H, $OR_6$, $CH_2CH_2OR_6$, $CH_2CH_2N(CH_3)_2$, $CH_2CH_2N(CH_2CH_3)_2$, Cl, F, Br, I, substituted and unsubstituted $C_1$-$C_{30}$ alkyl, substituted and unsubstituted $C_3$-$C_{30}$ cycloalkyl, substituted and unsubstituted $C_3$-$C_{30}$ heterocycloalkyl, substituted and unsubstituted $C_1$-$C_{30}$ alkyloxyl, substituted and unsubstituted $C_3$-$C_{30}$ cycloalkyloxyl, substituted and unsubstituted aryl, substituted and unsubstituted heteroaryl, substituted and unsubstituted $C_1$-$C_{30}$ alkylcarbonyl, substituted and unsubstituted $C_1$-$C_{30}$ alkylamino, $L_1$-$L_4$-$L_2$-W, and $C—(=O)$-W;
- $R_6$ is selected from H, F, Cl, Br, I, $C(=O)R_5$, substituted and unsubstituted $C_1$-$C_{30}$ alkyl, substituted and unsubstituted $C_3$-$C_{30}$ cycloalkyl, substituted and unsubstituted $C_3$-$C_{30}$ heterocycloalkyl, substituted and unsubstituted $C_2$-$C_{30}$ alkenyl, substituted and unsubstituted $C_2$-$C_{30}$ alkynyl, substituted and unsubstituted $C_1$-$C_{30}$ alkyloxyl, substituted and unsubstituted $C_3$-$C_{30}$ cycloalkyloxyl, substituted and unsubstituted aryl, substituted and unsubstituted heteroaryl, $L_1$-$L_4$-$L_2$-W, and $C—(=O)$-W;
- R is selected from nothing, $CH_2C(=O)OR_6$, substituted and unsubstituted $C_1$-$C_{30}$ alkylene, substituted and unsubstituted $C_3$-$C_{30}$ cycloalkylene, substituted and unsubstituted $C_3$-$C_{30}$ heterocycloalkylene, substituted and unsubstituted $C_1$-$C_{30}$ alkoxylene, substituted and unsubstituted $C_2$-$C_{30}$ alkenylene, substituted and unsubstituted $C_2$-$C_{30}$ alkynylene, substituted and unsubstituted aryl, and substituted and unsubstituted heteroaryl, wherein any $CH_2$ in R may be further replaced with O, S, or $NR_6$;
- $R_1$ and $R_2$ are each independently selected from H, substituted and unsubstituted $C_1$-$C_{30}$ alkyl, substituted and unsubstituted $C_3$-$C_{30}$ cycloalkyl, substituted and unsubstituted $C_3$-$C_{30}$ heterocycloalkyl, substituted and unsubstituted $C_1$-$C_{30}$ alkyloxyl, substituted and unsubstituted $C_2$-$C_{30}$ alkenyl, substituted and unsubstituted $C_2$-$C_{30}$ alkynyl, substituted and unsubstituted aryl and substituted and unsubstituted heteroaryl residues, wherein any $CH_2$ group(s) may be replaced with O, S, or NH;
- $R_{11}$ and $R_{12}$ are each independently selected from nothing, H, $CH_2C(=O)OR_{11}$, substituted and unsubstituted $C_1$-$C_{30}$ alkylene, substituted and unsubstituted $C_3$-$C_{30}$ cycloalkylene, substituted and unsubstituted $C_3$-$C_{30}$ heterocycloalkylene, substituted and unsubstituted $C_1$-$C_{30}$ alkoxylene, substituted and unsubstituted $C_2$-$C_{30}$ alkenylene, substituted and unsubstituted $C_2$-$C_{30}$ alkynylene, substituted and unsubstituted aryl, and substituted and unsubstituted heteroaryl, wherein any $CH_2$ group(s) may be replaced with O, S, or NH;
- $L_1$ and $L_2$ are each independently selected from nothing, O, $—O$-$L_3$-, $—N(L_3)$-, $—N(L_3)$-$CH_2—O$, $—N(L_3)$-$CH_2—N(L_5)$-, $—O—CH_2—O—$, and $—O—CH(L_3)$-O, wherein for each of $L_1$ and $L_2$, each of $L_3$ and $L_5$ is independently selected from nothing, H, substituted and unsubstituted $C_1$-$C_{30}$ alkyl, substituted and unsubstituted $C_3$-$C_{30}$ cycloalkyl, substituted and unsubstituted $C_3$-$C_{30}$ heterocycloalkyl, substituted and unsubstituted aryl, substituted and unsubstituted heteroaryl, substituted and unsubstituted $C_1$-$C_{30}$ alkoxyl, substituted and unsubstituted $C_1$-$C_{30}$ alkylamino, wherein any carbon or hydrogen may be further independently replaced with O, S, or $NL_3$;
- $L_4$ is selected from nothing and $C=O$;
- W is selected from Structure W-1 and Structure W-2:

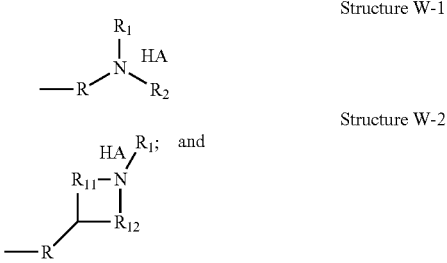

HA is selected from nothing, hydrochloride, hydrobromide, hydroiodide, nitric acid, sulfic acid, bisulfic acid, phosphoric acid, phosphorous acid, phosphonic acid, isonicotinic acid, acetic acid, lactic acid, salicylic acid, citric acid, tartaric acid, pantothenic acid, bitartaric acid, ascorbic acid, succinic acid, maleic acid, or any other pharmaceutically acceptable acid.

2. The topical pharmaceutical formulation of claim 1, wherein W is Structure W-1.

3. The topical pharmaceutical formulation of claim 1, wherein the compound of Structure LRA-1 is selected from
diethylaminoethyl [R-(E)]-1-[[[1-[3-[2-(7-chloro-2-quinolinyl)ethenyl]phenyl]-3-[2-(1-hydroxy-1-methylethyl)phenyl]propyl]thio]methyl]cyclopropaneacetate;
diethylaminoethyl 2-[1-[[(1R)-1-[3-[2-(7-chloroquinolin-2-yl)ethenyl]phenyl]-3-[2-(2-hydroxypropan-2-yl)phenyl]propyl]sulfanylmethyl]cyclopropyl]acetate;

2-pyrrolidinemethyl 2-[1-[[(1R)-1-[3-[2-(7-chloroquinolin-2-yl)ethenyl]phenyl]-3-[2-(2-hydroxypropan-2-yl)phenyl]propyl]sulfanylmethyl]cyclopropyl]acetate;
and pharmaceutically acceptable salts thereof.

4. The topical pharmaceutical formulation of claim 3, wherein the compound of Structure LRA-1 is selected from
diethylaminoethyl [R-(E)]-1-[[[1-[3-[2-(7-chloro-2-quinolinyl)ethenyl]phenyl]-3-[2-(1-hydroxy-1-methylethyl)phenyl]propyl]thio]methyl]cyclopropaneacetate hydrochloride;
diethylaminoethyl 2-[1-[[(1R)-1-[3-[2-(7-chloroquinolin-2-yl)ethenyl]phenyl]-3-[2-(2-hydroxypropan-2-yl)phenyl]propyl]sulfanylmethyl]cyclopropyl]acetate hydrochloride; and
2-pyrrolidinemethyl 2-[1-[[(1R)-1-[3-[2-(7-chloroquinolin-2-yl)ethenyl]phenyl]-3-[2-(2-hydroxypropan-2-yl)phenyl]propyl]sulfanylmethyl]cyclopropyl]acetate hydrochloride.

5. The topical pharmaceutical formulation of claim 1, which is a solution that can be sprayed onto skin of a patient.

6. The topical pharmaceutical formulation of claim 5, wherein the compound of Structure LRA-1 is diethylaminoethyl [R-(E)]-1-[[[1-[3-[2-(7-chloro-2-quinolinyl)ethenyl]phenyl]-3-[2-(1-hydroxy-1-methylethyl)phenyl]propyl]thio]methyl]cyclopropaneacetate hydrochloride.

7. The topical pharmaceutical formulation of claim 5, wherein the compound of Structure LRA-1 is 2-pyrrolidinemethyl 2-[1-[[(1R)-1-[3-[2-(7-chloroquinolin-2-yl)ethenyl]phenyl]-3-[2-(2-hydroxypropan-2-yl)phenyl]propyl]sulfanylmethyl]cyclopropyl]acetate hydrochloride.

8. The topical pharmaceutical formulation of claim 5, which is an aqueous solution optionally comprising an alcohol.

* * * * *